US012734283B2

(12) United States Patent
Matovina et al.

(10) Patent No.: US 12,734,283 B2
(45) Date of Patent: Sep. 15, 2026

(54) PERFUSION MONITORING AND CONTROL SYSTEM

(71) Applicant: Terumo Cardiovascular Systems Corporation, Ann Arbor, MI (US)

(72) Inventors: Richard M. Matovina, Ann Arbor, MI (US); Suzanne Osborne, Ann Arbor, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 902 days.

(21) Appl. No.: 17/325,397

(22) Filed: May 20, 2021

(65) Prior Publication Data

US 2022/0370702 A1 Nov. 24, 2022

(51) Int. Cl.

| | |
|---|---|
| ***A61M 1/36*** | (2006.01) |
| ***G16H 20/17*** | (2018.01) |
| ***G16H 40/63*** | (2018.01) |

(52) U.S. Cl.

CPC ........ *A61M 1/3666* (2013.01); *A61M 1/3607* (2014.02); *G16H 20/17* (2018.01); *G16H 40/63* (2018.01)

(58) Field of Classification Search

CPC .......................... A61M 1/3666; A61M 1/3607

See application file for complete search history.

(56) References Cited

U.S. PATENT DOCUMENTS

| | | | |
|---|---|---|---|
| 5,817,007 | A | 10/1998 | Fodgaard et al. |
| 6,423,022 | B1 | 7/2002 | Roeher et al. |

(Continued)

FOREIGN PATENT DOCUMENTS

| | | |
|---|---|---|
| CN | 209916851 | 1/2020 |
| EP | 1900384 | 3/2008 |

(Continued)

OTHER PUBLICATIONS

Extended European Search Report in European Appln No. 22174416.2 dated Oct. 4, 2022, 9 pages.

(Continued)

*Primary Examiner* — Catharine L Anderson
*Assistant Examiner* — Kate Elizabeth Strachan
(74) *Attorney, Agent, or Firm* — Fish & Richardson P.C.

(57) ABSTRACT

This document describes medical systems for monitoring parameters of a patient during a medical procedure. A user, such as a practitioner, can provide input of parameter settings for ranges of patient parameters and semi-autonomous adjustments to the parameters. The semi-autonomous adjustments can be executed at a later time during the procedure, based on sensed real-time changes to the patient parameters. A computer system can monitor, in real-time, the patient parameters and generate GUI displays to be presented at the user's device. The GUI displays can output sensed real-time changes in the patient parameters, controls to adjust ranges for each of the parameters, and controls to perform semi-autonomous adjustments. The computer system can also generate projected trends for the real-time parameters, which can be used by the user to adjust patient parameters during the procedure. User selection of semi-autonomous adjustments can be executed by the computer system at a heart/lung machine.

13 Claims, 17 Drawing Sheets

(56) References Cited

U.S. PATENT DOCUMENTS

| | | | | |
|---|---|---|---|---|
| 6,691,047 | B1 | 2/2004 | Fredericks | |
| 6,692,518 | B2 | 2/2004 | Carson | |
| 6,775,577 | B2 | 8/2004 | Crnkovich et al. | |
| 7,038,588 | B2 | 5/2006 | Boone et al. | |
| 7,336,997 | B2 | 2/2008 | Fukui | |
| 7,364,563 | B2 | 4/2008 | Lucke et al. | |
| 7,611,478 | B2 | 11/2009 | Lucke et al. | |
| 7,674,235 | B2 | 3/2010 | Nier et al. | |
| 7,787,946 | B2 | 8/2010 | Stahmann et al. | |
| 7,788,038 | B2 | 8/2010 | Oshita et al. | |
| 7,981,281 | B2 | 7/2011 | Yu et al. | |
| 8,062,513 | B2 | 11/2011 | Yu et al. | |
| 8,862,196 | B2 | 10/2014 | Lynn | |
| 8,868,350 | B2 | 10/2014 | Akonur et al. | |
| 8,961,461 | B2 | 2/2015 | Stewart et al. | |
| 9,002,655 | B2 | 4/2015 | Bernard | |
| 9,399,091 | B2 | 7/2016 | Sigg et al. | |
| 9,400,199 | B2 | 7/2016 | Wolff | |
| 9,486,568 | B2 | 11/2016 | Atallah et al. | |
| 9,717,840 | B2 | 8/2017 | Burbank et al. | |
| 10,179,199 | B2 | 1/2019 | Bene | |
| 10,342,910 | B2 | 7/2019 | Atallah et al. | |
| 2002/0068015 | A1 | 6/2002 | Polaschegg et al. | |
| 2002/0169386 | A1 | 11/2002 | Johnson, Jr. | |
| 2005/0126961 | A1 | 6/2005 | Bissler et al. | |
| 2005/0230314 | A1 | 10/2005 | Kim et al. | |
| 2005/0256444 | A1* | 11/2005 | O'Mahony | A61M 1/3609 604/4.01 |
| 2008/0027368 | A1* | 1/2008 | Kollar | A61M 1/3621 604/6.14 |
| 2010/0137693 | A1 | 6/2010 | Porras et al. | |
| 2014/0271356 | A1* | 9/2014 | Samolyk | A61M 1/3621 422/44 |
| 2016/0256090 | A1 | 9/2016 | Barrett et al. | |
| 2016/0346452 | A1* | 12/2016 | Gilbert | A61M 1/369 |
| 2017/0092227 | A1* | 3/2017 | Yik | A61M 1/159 |
| 2018/0154061 | A1 | 6/2018 | Turner | |
| 2018/0361051 | A1 | 12/2018 | Kopperschmidt | |
| 2019/0365976 | A1 | 12/2019 | Tatonetti | |
| 2020/0054816 | A1 | 2/2020 | Frugier | |
| 2020/0179045 | A1 | 6/2020 | Levin et al. | |
| 2020/0206405 | A1 | 7/2020 | Wyeth et al. | |
| 2021/0134451 | A1* | 5/2021 | Fallen | G16H 40/40 |
| 2021/0228794 | A1 | 7/2021 | Lecamwasam et al. | |

FOREIGN PATENT DOCUMENTS

| | | |
|---|---|---|
| EP | 1955723 | 4/2017 |
| EP | 3524290 | 8/2019 |
| EP | 3145392 | 10/2019 |
| EP | 3806108 | 4/2021 |
| WO | WO 2002/049500 | 6/2002 |
| WO | WO 2002/058536 | 8/2002 |
| WO | WO 2010/066405 | 6/2010 |
| WO | WO 2016/066405 | 5/2016 |
| WO | WO 2019/152699 | 8/2019 |
| WO | WO-2019152699 A1 * | 8/2019 |
| WO | WO 2019/193604 | 10/2019 |

OTHER PUBLICATIONS

Amc.nl, [online], "Who is Who in Research," available No. later than Dec. 1, 2019, retrieved on Oct. 26, 2020, retrieved from URL<https://www.amc.nl/web/research-75/department/intensive-care-medicine.htm>, 5 pages.

Arvind et al., "Predicting Surgical Complications in Adult Patients Undergoing Anterior Cervical Discectomy and Fusion Using Machine Learning, " Neurospine, 2018, 15(4):329-337.

Baumgartner et al., "A Comprehensive Approach towards Extra-Corporal Circulation Control using Fuzzy Logic," Presented at International Conference on Fuzzy Systems, Barcelona, Spain, Jul. 18-23, 2010, IEEE, Sep. 2010, 5 pages.

Bidmc.org, [online], "Beth Israel Deaconess Medical Center," 2020, retrieved on Oct. 22, 2020, retrieved from URL<https://www.bidmc.org/>, 5 pages.

Busch et al., "Noninvasive optical measurement of microvascular cerebral hemodynamics and autoregulation in the neonatal ECMO patient," Pediatric Research, 2020, 9 pages.

Campus.uva.nl, [online], "Academic Medical Center," 2020, retrieved on Oct. 23, 2020, retrieved from URL<https://campus.uva.nl/en/amc/academic-medical-center.html?cb>, 3 pages.

Cs.washington.edu, [online], "Investing in the future," 2019, retrieved on Oct. 26, 2020, retrieved from URL<https://www.cs.washington.edu/>, 2 pages.

Dascena.com, [online], "Dascena develops algorithms as predictive biomarkers for complex conditions," 2020, retrieved on Oct. 26, 2020, retrieved from URL<https://www.dascena.com/>, 8 pages.

Dhzb.de, [online], "Welcome to the Department of Cardiothoracic and Vascular Surgery," available no later than Dec. 1, 2019, retrieved on Oct. 26, 2020, retrieved from URL<https://www.dhzb.de/en/departments/cardiothoracic-and-vascular-surgery>, 2 pages.

En.rnhospital.com, [online], "Renmin Hospital of Wuhan University Hubei General Hospital," 2015, retrieved on Oct. 23, 2020, retrieved from URL<http://en.rmhospital.com/contact.html>, 2 pages.

En.umed.wroc.pl, [online], "Department of Anesthesiology and Intensive Therapy," 2019, retrieved on Oct. 22, 2020, retrieved from URL<https://www.en.umed.wroc.pl/en-anestezjologia>, 1 page.

Fernandes et al., "Machine Learning Models with Preoperative Risk Factors and Intraoperative Hypotension Parameters Predict Mortality After Cardiac Surgery," Journal of Cardiothoracic and Vascular Anesthesia, 2020, 30 pages.

Hatib et al., "Machine-learning Algorithm to Predict Hypotension Based on High-fidelity Arterial Pressure Waveform Analysis," Anesthesiology, 2018, 12 pages.

Health.utah.edu, [online], "Department of Nutrition & Integrative Physiology (NUIP)," 2020, retrieved on Oct. 26, 2020, retrieved from URL<https://health.utah.edu/nutrition-integrative-physiology>, 14 pages.

Icahn.mssm.edu, [online], "Department of Orthopaedics," 2020, retrieved on Oct. 23, 2020, retrieved from URL<https://icahn.mssm.edu/about/departments/orthopaedics>, 2 pages.

Kim et al., "Predicting Cardiac Arrest and Respiratory Failure Using Feasible Artificial Intelligence with Simple Trajectories of Patient Data," J Clin Med, 2019, 8(9):1336, 14 pages.

Lee et al., "Derivation and Validation of Machine Learning Approaches to Predict Acute Kidney Injury after Cardiac Surgery," J Clin Med, 2018, 7(10):322, 13 pages.

Lukaszewski et al., "The use of data science to analyse physiology of oxygen delivery in the extracorporeal circulation, " BMC Cardiovascular Disorders, 2019, 19:292, 6 pages.

Lundberg et al., "Explainable machine-learning predictions for the prevention of hypoxaemia during surgery," Nat Biomed Eng., 2018, 2(10):749-760.

Medicine.yonsei.ac.kr, [online], "Dean's Message," 2009, retrieved on Oct. 26, 2020, retrieved from URL<https://medicine.yonsei.ac.kr/en/About_YUCM/message/index.asp>, 1 page.

Meyer et al., "Machine learning for real-time prediction of complications in critical care: a retrospective study," Lancet Respir Med., 2018, 6(12):905-914.

Mohamadlou et al., "Prediction of Acute Kidney Injury With a Machine Learning Algorithm Using Electronic Health Record Data," Can J Kidney Health Dis, 2018, 5:1-9.

Mottchildren.org, [online], "Congenital Heart Center at Mott Children's Hospital," 2020, retrieved on Oct. 23, 2020, retrieved from URL<https://www.mottchildren.org/our-locations/congenital-heart-center-mott-childrens-hospital>, 1 page.

Nymu-e.ym.edu.tw, [online], "School of Medicine," 2014, retrieved on Oct. 22, 2020, retrieved from URL<https://nymu-e.ym.edu.tw/files/11-1134-18.php>, 2 pages.

Olive et al., "Current monitoring and innovative predictive modeling to improve care in the pediatric cardiac intensive care unit," Translational Pediatrics, 2018, 7(2):120-128.

PCT International Search Report and Written Opinion in International Appln. No. PCT/US2020/058154, dated Dec. 29, 2020, 13 pages.

(56) References Cited

OTHER PUBLICATIONS

Peds.us.edu, [online], "Critical Care Medicine," 2020, retrieved on Oct. 23, 2020, retrieved from URL<https://www.peds.uw.edu/specialties/critical-care-medicine>, 2 pages.
Poss et al., "Machine learning reveals serum sphingolipids as cholesterol-independent biomarkers of coronary artery disease," The Journal of Clinical Investigation, 2019, 130(3):1363-1376.
Shah et al., "Neural Networks to Predict Radiographic Brain Injury in Pediatric Patients Treated with Extracorporeal Membrane Oxygenation," Journal of Clinical Medicine, 2020, 9(2718):14 pages.
Shirazu.ac.ir, [online], "Shiraz University," available no later than Dec. 1, 2019, retrieved on Oct. 26, 2020, retrieved from URL<http://www2.shirazu.ac.ir/en>, 1 page.
Tomašev et al., "A clinically applicable approach to continuous prediction of future acute kidney injury," Nature, 2019, 572(7767):116-119.
Tseng et al., "Prediction of the development of acute kidney injury following cardiac surgery by machine learning, " Critical Care, 2020, 24:478, 13 pages.
Ucl.ac.uk, [online], "UCL Computer Science," 2020, retrieved on Oct. 26, 2020, retrieved from URL<https://www.ucl.ac.uk/computer-science>, 5 pages.
Uclahealthy.org, [online], "UCLA Anesthesiology & Perioperative Medicine," 2020, retrieved on Oct. 26, 2020, retrieved from URL<https://www.uclahealth.org/anes/>, 3 pages.
Utsouthwestern.edu, [online], "UTSouthwestern Medical Center," 2020, retrieved on Oct. 23, 2020, retrieved from URL<https://www.utsouthwestern.edu/>, 4 pages.
Wijnberge et al., "Effect of a Machine Learning-Derived Early Warning System for Intraoperative Hypotension vs Standard Care on Depth and Duration of Intraoperative Hypotension During Elective Noncardiac Surgery: The HYPE Randomized Clinical Trial," JAMA, 2020, 323(11):1052-1060, E1-E9.
Wijnberge et al., "The use of a machine-learning algorithm that predicts hypotension during surgery in combination with personalized treatment guidance: study protocol for a randomized clinical trial," Trials, 2019, 20:582, 9 pages.
Xsensor.com, [online], "New Wave of Innovation: AI/ML in Medtech," 2020, retrieved on Oct. 26, 2020, retrieved from URL<https://www.xsensor.com/post/new-wave-of-innovation-ai-ml-in-medtech>, 4 pages.
Xsensor.com, [online], "Optimize Human Performance," 2020, retrieved on Oct. 26, 2020, retrieved from URL<https://www.xsensor.com/>, 3 pages.
Zhang et al., "Continuous perfusion of donor hearts with oxygenated blood cardioplegia improves graft function," Transplant International: Official Journal of the European Society for Organ Transplantation, 2010, 23(11):1164-1170.

* cited by examiner

Computer System
202

Receive user-defined parameter settings 402

Generate UI display 404

Receive real-time parameters 406

Generate parameter trends based on user-defined settings and real-time parameters 408

Transmit parameter trends for display at user device 410

Receive parameter adjustment(s) 412

Transmit adjustment(s) to HLM 414
- Manual adjustment(s)
- Semi-autonomous adjustment(s)

Store user-defined settings and procedure results 416

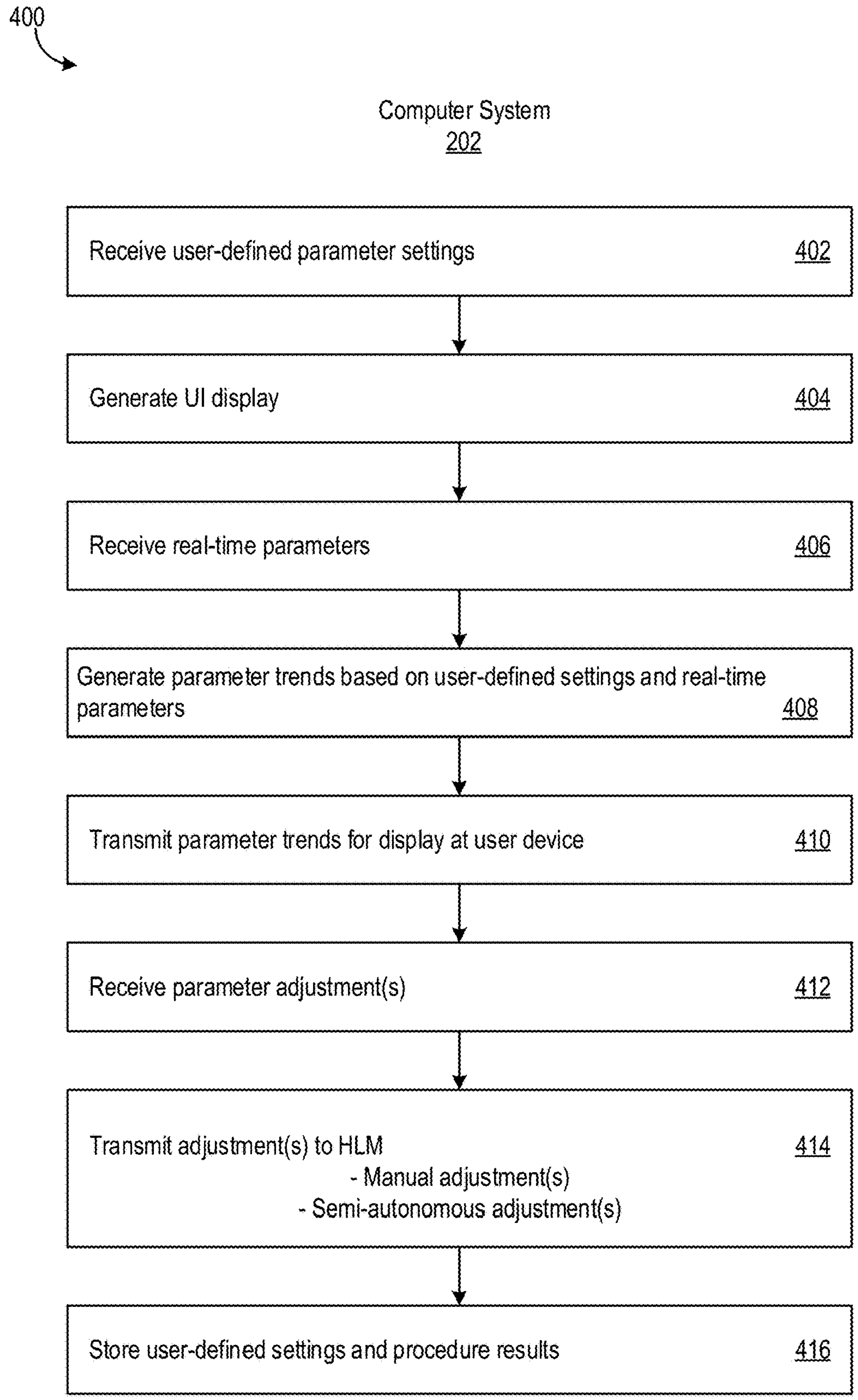

FIG. 4

600
Arterial
618
pH
pO2
O2 Sat
pCO2
DO2
Temp
Line Press
BSA
CI
622
ABD
Clamp
624
Arterial
Capiox
4.00
2900
Coast
1250
Delta Q (ART – VEN)
0.50
Status/fault info
626
628
630
632
634
Venous
620
pH
pO2
O2 Sat
pCO2
VO2
Temp
BE
Bicarb
K+
Hb
HCT
Occluder
3/8"
% Open
100
Venous Level
095
-50
VEN Flow
3.50
636
Parameter Trending: PaCO2
602
604A-N
603A
603B
603C
601
608
603D
603E
603N
610
612
606
614A-N
PaCO2 Alarm (70 mmHg):
PaCO2 Alert (65 mmHg):
PaCO2 UCL (50 mmHg):
PaCO2 (41 mmHg)
PaCO2 LCL (35 mmHg):
PaCO2 Alert (30 mmHg):
PaCO2 Alarm (25 mmHg):
Sweep (1.0 L/min)
FiCO2 (0.04)
Time
Gas Delivery
616
Meas Flow
2.00
Set Flow
2.00
Gas/Blood Flow Ratio
0.5:1
Air / O2 / CO2
Meas O2
90%
Set FiO2
0.90
Low FiO2 limit
Meas CO2
4%
Set FiCO2
0.04
High FiCO2 limit
Status/fault info
Arterial Flow
Venous Occlusion
Gas Flow
FiO2
FiCO2
0
Max
0
100%
Open
0.0
10.0
0.21
1.0
0.0
0.1
620A-N
620A-N

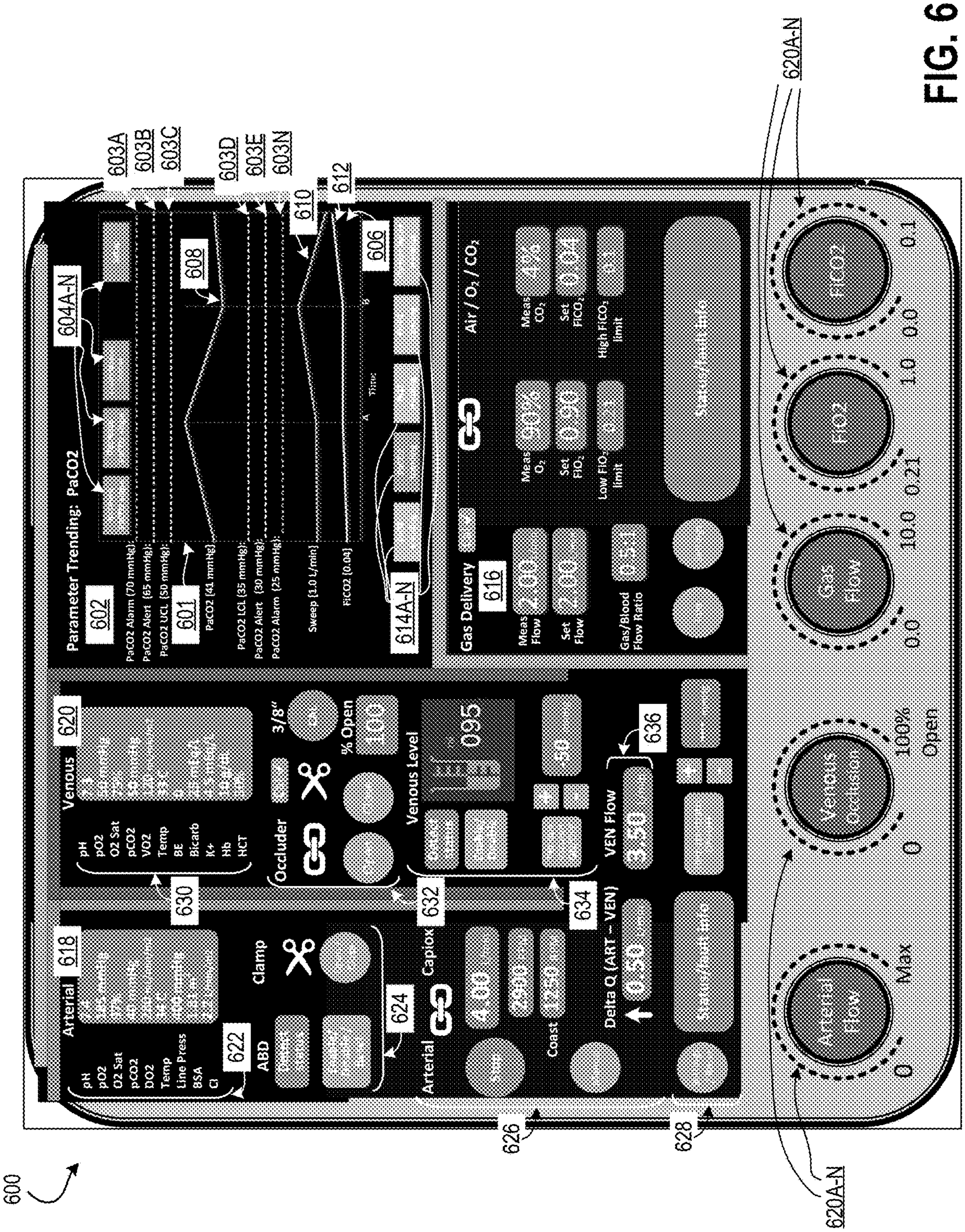

FIG. 6

PERFUSION MONITORING AND CONTROL SYSTEM

BACKGROUND

1. Technical Field

This document relates to medical systems that have integrated monitoring and control features to perform manual and semi-autonomous operations. For example, this document relates to heart/lung machine systems that are integrated with a calibrated blood gas monitor to facilitate real-time manual and semi-autonomous perfusion monitoring and control operations.

2. Background Information

Heart/lung machine ("HLM") systems are used, along with an extracorporeal circuit and hollow fiber oxygenator, to meet a patient's circulatory and blood gas exchange needs during medical procedures such as cardiopulmonary bypass ("CPB") surgery. Blood from the patient is either gravity drained, or VAVD (vacuum assisted venous drainage) is used, to obtain the required amount of flow to maintain sufficient volume in a reservoir of the extracorporeal circuit. A pump, such as a peristaltic pump or a centrifugal pump coupled with a magnetic drive system, is sometimes used in the main line of the extracorporeal circuit in order to pump blood from the reservoir, through the oxygenator, and finally back to the patient. In addition to a heart/lung machine per se, heart-lung machine systems can include multiple types of patient monitoring devices that are used in conjunction with the heart/lung machine.

During CPB surgery, the HLM can provide arterial blood flow at appropriate pressures to circulate throughout the patients' body while the blood bypasses the patients' heart and lungs that are not functioning during the surgery. One or more cannula can be placed in a right side of the heart, allowing the low oxygen/high carbon dioxide (de-saturated) blood from the body to enter the extracorporeal circuit. The de-saturated blood flows through the circuit into an oxygenator that performs the same job as the lungs: oxygenation of the blood while removing carbon dioxide. A mechanical (arterial) pump on the HLM can replace the function of the heart. This pump can provide the proper cardiac output for the specific patient. The cardiac output delivered to the patent can be chosen to be similar to patient needs during normal circulation. The re-oxygenated blood can then returned to the body via another cannula placed in the aorta.

SUMMARY

This document describes medical systems that have integrated monitoring and control features to perform manual and semi-autonomous operations. For example, the document describes a perfusion monitoring and control system that integrates the functionalities of an HLM and a calibrated blood gas monitor, which can be used to safely and effectively perfuse a patient during medical procedures such as, but not limited to, CPB surgery. The integrated functionalities can provide real-time control and monitoring of arterial and venous blood flow, ventilation gas delivery to an oxygenator, continuous in-line blood gas parameter monitoring (arterial and venous), and optional user-configurable semi-automated monitoring and parameter trending response features. Using capnography, the integrated functionalities can also provide for real-time exhaust gas monitoring to measure expiratory gases from the oxygenator. The systems described herein can also provide synergistic monitoring and control functionality that can be customized by a user (e.g., practitioner, perfusionist, clinician) to meet the user's needs for maintaining perfusion parameters in desired ranges, quickly identifying any undesired trending, and providing pre-configured corrective parameter trending response capability. As a result, the safety and effectiveness of perfusion practices can be improved.

In one aspect, this disclosure is directed to a system for monitoring patient parameters of a patient during a medical procedure. The system can include a heart/lung machine used with a continuous blood gas monitor; a data store for storing one or more of parameter presets, patient parameters, semi-autonomous parameter trending response adjustments, parameter ranges, and control limits; a user device for providing monitoring and control capabilities of patient parameters, wherein the user device is configured to output a first graphical user interface (GUI) display on a display screen before the medical procedure and to receive, via the first GUI display before the medical procedure, user input indicating parameter settings for (i) ranges for each of the patient parameters and (ii) semi-autonomous parameter trending response adjustments to one or more of the patient parameters, wherein the semi-autonomous parameter trending response adjustments are executed during the medical procedure based on sensed real-time changes in the patient parameters; and a computer system for monitoring and controlling, in real-time during the medical procedure, the patient parameters, the computer system configured to: receive, from the user device before the medical procedure, the parameter settings; generate, based on the user input indicating parameter settings and before the medical procedure, a second GUI display to be outputted by the display screen of the user device during the medical procedure, wherein the second GUI display provides (i) a display of the sensed real-time changes in the patient parameters, (ii) controls to adjust one or more of the ranges for each of the displayed patient parameters, (iii) and controls to perform one or more of the semi-autonomous parameter trending response adjustments to one or more of the displayed patient parameters; generate, based on (i) real-time patient parameters received from at least one of the heart/lung machine and one or more sensors during the medical procedure and (ii) the parameter settings, projected trends for each of the real-time patient parameters; update the second GUI display to further provide the projected trends for each of the real-time patient parameters; transmit the updated second GUI display to the user device to be outputted by the display screen of the user device; receive, from the user device, user input indicating a selection of one or more of the controls to perform one or more of the semi-autonomous parameter trending response adjustments to the displayed real-time patient parameters; and execute the user-selected one or more of the semi-autonomous parameter trending response adjustments.

Such a system for monitoring patient parameters of a patient during a medical procedure may optionally include one or more of the following features. For example, the computer system can further be configured to: receive, (i) from at least one of the heart/lung machine and the one or more sensors and (ii) after execution of the user-selected one or more of the semi-autonomous parameter trending response adjustments, updated real-time patient parameters; determine, based on the updated real-time patient parameters, updated trends for each of the updated real-time patient parameters; update the second GUI display to further provide the updated real-time patient parameters and the updated trends for each of the updated real-time patient parameters; transmit the updated second GUI display to the user device to be outputted by the display screen of the user device; and store, in the data store, (i) the executed one or more of the semi-autonomous parameter trending response adjustments, (ii) the updated real-time patient parameters, and (iii) the updated trends for each of the updated real-time patient parameters.

The one or more sensors can include at least one of: a camera, an arterial shunt sensor, a venous shunt sensor, an air detector, a bubble sensor, an arterial optical fluorescent sensor, a venous optical fluorescent sensor, an arterial optical reflective sensor, a venous optical reflective sensor, a hematocrit level sensor, and a hemoglobin sensor. The one or more sensors can be configured to monitor, in real-time before and during the medical procedure, at least one of a blood gas level, a blood flow, a venous reservoir blood level, a temperature, and a pressure of the patient.

The one or more semi-autonomous parameter trending response adjustments can include adjusting an arterial blood flow of the patient, adjusting a venous blood flow of the patient, adjusting a venous vacuum source, adjusting a hemoconcentrator circuit flow, monitoring an exhaust gas flow and concentration, monitoring an anesthetic gas inlet and outlet, adjusting a ventilation gas flow, adjusting a ventilation gas concentration, monitoring inlet gas ventilation, and monitoring exhaust gas ventilation.

The second GUI display can provide, in a single interface and for each of the displayed real-time patient parameters, (i) sensed changes in the real-time patient parameters, (ii) the controls to perform one or more of the semi-autonomous parameter trending response adjustments to the displayed real-time patient parameters, (iii) controls to perform one or more manual adjustments to the displayed real-time patient parameters, and (iv) the projected trends for each of the displayed real-time patient parameters.

The computer system can further be configured to receive, from the user device and during the medical procedure, updated user input indicating (i) updated ranges for one or more of the displayed real-time patient parameters and (ii) updated semi-autonomous parameter trending response adjustments to one or more of the displayed real-time patient parameters.

Generating, by the computer system, the projected trends for each of the real-time patient parameters can include determining a slope for each of the real-time patient parameters over a predetermined period of time.

The ranges for each of the patient parameters can include upper and lower limits, and the computer system can further be configured to update the second GUI display to further provide the upper and lower limits concurrently with the projected trends.

The one or more semi-autonomous parameter trending response adjustments can include (i) incrementally increasing, based on the parameter settings and the projected trends, a slope of the one or more of the displayed real-time patient parameters until an upper limit is reached and (ii) incrementally decreasing, based on the parameter settings and the projected trends, the slope of the one or more of the displayed real-time patient parameters until a lower limit is reached.

Executing, by the computer system, the user-selected one or more of the semi-autonomous parameter trending response adjustments can include at least one of (i) semi-autonomously increasing a slope of one of the real-time patient parameters until the slope of the one of the real-time patient parameters is within a first threshold range defined by the parameter settings and (ii) semi-autonomously decreasing a slope of another of the real-time patient parameters until the slope of the another of the real-time patient parameters is within a second threshold range defined by the parameter settings.

The computer system can also be configured to update the second GUI display to further provide a graph depicting changes to a user-selected real-time patient parameter of the displayed real-time patient parameters, wherein trend lines depicted in the graph are adjusted, by the computer system in real-time, in response to (i) sensed changes in the user-selected real-time patient parameter, (ii) sensed changes in one or more other real-time patient parameters that are associated with the user-selected real-time patient parameter, and (iii) execution of one or more semi-autonomous parameter trending response adjustments.

Moreover, the computer system can be further configured to: receive, from the one or more sensors and during the medical procedure, signals indicating a blood level in a venous reservoir; automatically open a clamp of a hemoconcentrator in fluid communication with the venous reservoir based on the signals indicating that the blood level satisfies a predetermined threshold value, wherein the predetermined threshold value is defined by the parameter settings; actuate, in response to opening the clamp of the hemoconcentrator and during the medical procedure, a vacuum of the hemoconcentrator by a predetermined amount, wherein the predetermined amount is defined by the parameter settings; receive, from the one or more sensors and during the medical procedure, updated signals indicating the blood level in the venous reservoir; and close the clamp of the hemoconcentrator in response to determining that the signals are less than the predetermined threshold value.

In another aspect, this disclosure is directed to a method for monitoring patient parameters of a patient during a medical procedure. The method can include: receiving, from a user device before a medical procedure, parameter settings indicating (i) ranges for patient parameters that are monitored during the medical procedure and (ii) semi-autonomous parameter trending response adjustments to one or more of the patient parameters, wherein the semi-autonomous parameter trending response adjustments are executed during the medical procedure based on sensed real-time changes in the patient parameters; generating, based on the parameter settings and before the medical procedure, a graphical user interface (GUI) display to be outputted by a display screen of the user device during the medical procedure, wherein the GUI display provides (i) a display of the sensed real-time changes in the patient parameters, (ii) controls to adjust one or more of the ranges for each of the displayed patient parameters, (iii) and controls to perform one or more of the semi-autonomous parameter trending response adjustments to one or more of the displayed patient parameters; generating, based on (i) real-time patient parameters received from at least one of a heart/lung machine and one or more sensors during the medical procedure and (ii) the parameter settings, projected trends for each of the real-time patient parameters; updating the GUI display to further provide the projected trends for each of the real-time patient parameters; transmitting the updated GUI display to the user device to be outputted by the display screen of the user device; receiving, from the user device, user input indicating a selection of one or more of the controls to perform one or more of the semi-autonomous parameter trending response adjustments to the displayed real-time patient parameters; and executing the user-selected one or more of the semi-autonomous parameter trending response adjustments.

Such a method for monitoring patient parameters of a patient during a medical procedure may optionally include one or more of the following features. For example, the method can further include receiving, (i) from at least one of the heart/lung machine and the one or more sensors and (ii) after execution of the user-selected one or more of the semi-autonomous parameter trending response adjustments, updated real-time patient parameters; determining, based on the updated real-time patient parameters, updated trends for each of the updated real-time patient parameters; updating the GUI display to further provide the updated real-time patient parameters and the updated trends for each of the updated real-time patient parameters; transmitting the updated GUI display to the user device to be outputted by the display screen of the user device; and storing, in a data store, (i) the executed one or more of the semi-autonomous parameter trending response adjustments, (ii) the updated real-time patient parameters, and (iii) the updated trends for each of the updated real-time patient parameters.

The method can also include receiving, from the user device and during the medical procedure, updated user input indicating (i) updated ranges for one or more of the displayed real-time patient parameters and (ii) updated semi-autonomous parameter trending response adjustments to one or more of the displayed real-time patient parameters; updating the GUI display to further provide the updated user input; and transmitting the updated GUI to the user device to be outputted by the display screen of the user device.

As another example, generating the projected trends for each of the real-time patient parameters can include determining a slope for each of the real-time patient parameters over a predetermined period of time. The ranges for each of the patient parameters can also include upper and lower limits, and the method can further include updating the GUI display to further provide the upper and lower limits concurrently with the projected trends.

Executing the user-selected one or more of the semi-autonomous parameter trending response adjustments can include at least one of (i) semi-autonomously increasing a slope of one of the real-time patient parameters until the slope of the one of the real-time patient parameters is within a first threshold range defined by the parameter settings and (ii) semi-autonomously decreasing a slope of another of the real-time patient parameters until the slope of the another of the real-time patient parameters is within a second threshold range defined by the parameter settings.

The method can also include updating the GUI display to further provide a graph depicting changes to a user-selected real-time patient parameter of the displayed real-time patient parameters, wherein trend lines depicted in the graph are adjusted, in real-time, in response to (i) sensed changes in the user-selected real-time patient parameter, (ii) sensed changes in one or more other real-time patient parameters that are associated with the user-selected real-time patient parameter, and (iii) execution of one or more semi-autonomous parameter trending response adjustments.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. In case of conflict, the present specification, including definitions, will control. In addition, the materials, methods, and examples are illustrative only and not intended to be limiting. Furthermore, all references to features or objects A-N mean that there can be an infinite number of such features or objects.

The technology described in this document can provide one or more benefits. For example, the user and/or the HLM system can maintain perfusion parameters in control, based on real-time monitoring of such parameters. The disclosed systems provide an integrated system that can be used by the user to assess different parameters that are monitored during a medical procedure. Therefore, the user can see the parameters trending in real-time via a user interface. From that user interface, the user can, if desired, make adjustment to maintain the displayed parameters within a desired range of values. This capability can improve patient safety during perfusion using the HLM systems described herein. Thus, the disclosed systems and methods provide a single-device solution with integrated, synergistic HLM and blood gas monitor functionality for safe and effective perfusion.

As another example, using the systems and methods described herein, the user can more quickly identify any undesired trending during perfusion practice. Since parameters are continuously monitored and displayed on the user interface in real-time, the user can readily view trends of each of the parameters. Being able to see how the parameters are trending in real-time can be advantageous for the user to more quickly identify and respond to potential undesired trends. As a result, the user can adjust one or more parameters before the patient experiences any harm.

As yet another example, in some embodiments the disclosed technology can provide pre-configured corrective parameter trending capability during the medical procedure. When the user identifies undesired trending, the user can select an option on the user interface that adjusts one or more of the parameters. As a result, the undesired trending can be remedied or avoided. Before the medical procedure, in some embodiments the user can program or customize adjustments for one or more of the parameters. In other words, the user can select what actions can be taken to correct a parameter that is trending in an undesired manner. Therefore, during the medical procedure, when the user identifies undesired trending of a parameter, the user can readily select the option to correct the parameter based on the pre-identified adjustments that the user previously established. The pre-identified adjustment(s) can be immediately performed, and the parameter trends can be updated in real-time on the user interface. This is advantageous so that the user does not have to manually calculate or estimate adjustments to the parameter during the medical procedure. Therefore, because the user can identify and calculate adjustments to the parameter before the procedure and implement such adjustments during the procedure if need be, the patient's safety and perfusion efficacy can be improved.

The disclosed technology can also provide for semi-autonomous control of one or more devices used during medical procedures. The semi-autonomous control can be based on parameters, settings, and parameter adjustments that are configured by the user before the medical procedure. For example, during the procedure, the user can merely select an option on the user interface that causes one or more devices to be semi-autonomously controlled. This can assist the user in performing effective perfusion practices because the user can focus their time on monitoring all the parameters and ensuring the procedure is being correctly performed. During high-stress situations, it can be challenging for the user to monitor all the parameters and make adjustments to one or more devices to maintain the patient's safety. Therefore, having an option to invoke semi-autonomous control of one or more devices/parameters based on the user-defined settings prior to the procedure, patient safety and overall perfusion practices can be improved.

Moreover, the disclosed technology provides a more comprehensive approach to medical procedures that use HLMs. The disclosed technology can combine functions of the HLM, monitoring devices, and sensors in a central environment. Therefore, the user can monitor all parameters in the central environment, for example, by a single user interface. With centralized monitoring capabilities, the user can more easily and quickly identify trends of the parameters and make any necessary adjustments to ensure patient safety and effective perfusion practices. Moreover, this comprehensive approach to perfusion practice provides for advanced data collection for case record purposes and post-case analysis. This comprehensive approach also provides foundational functionality for more advanced servo-control of aspects such as arterial blood flow and gas delivery to target blood gas parameter values.

The disclosed technology can also provide the user with more tools that can improve medical procedures that use HLMs. With the disclosed technology, the user can improve their ability to appropriately respond to trending parameters, conditions, and other settings during the procedure. For example, the user can create custom settings for one or more parameters that are monitored during the medical procedure. The user can define ranges that they want the parameters to operate in throughout the procedure. The user can also pre-configure how the system responds in situations when the parameters are outside of the user-defined ranges. The pre-configured system responses can then be manually implemented by the user or semi-autonomously implemented by the system during the procedure. These tools assist the user in performing more effective and safe medical procedures.

The disclosed technology can assist the user in defining parameters and settings for different medical practice areas. Thus, the disclosed technology can provide a high degree of user-customization of controls and monitoring to address a wide range of user and institutional preferences and practices. In other words, the user can define parameters and settings for a first type of medical procedure. Those parameters and settings can be applied to any patient undergoing the first type of medical procedure. The user can then define different parameters and settings for a second type of medical procedure. Those parameters and settings can be applied to any patient undergoing the second type of medical procedure. This provides for a streamlined monitoring and control system that facilitates faster and more efficient preparation before a procedure, and monitoring and control of conditions during the procedure. As a result, patient safety can be improved across the board.

The disclosed technology can provide for optional user-configurable semi-automated functionality in the perfusion practice. For example, some of the semi-automated functionality that the user can configure includes trending of key parameters, defining desired control ranges/alert/alarm limits, defining corrective responses to undesired parameter trends, and the ability to quickly initiate the corrective responses. Such user-configurable semi-automated functions can be executed while the user still maintains full manual control capability during a procedure. Thus, the perfusion practice and patient outcomes can be improved.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 4 is a flowchart of an example process to monitor and control parameters for a medical procedure.

FIG. 6 is an example user interface for some embodiments of the monitoring and control system described herein.

Like reference numbers represent corresponding parts throughout.

DETAILED DESCRIPTION

This document describes medical systems that have integrated monitoring and control features to perform manual and semi-autonomous operations. For example, the document describes a perfusion monitoring and control system that integrates functionality of a HLM system and a calibrated blood gas monitor.

During medical procedures using HLMs (e.g., CPB, heart transplants, etc.), a practitioner (e.g., perfusionist) can continuously monitor patient physiologic parameters and extracorporeal circuit parameters. In response to such monitoring, the practitioner can make frequent adjustments to HLM system parameters to meet patient needs. The patient needs can vary over a course of the bypass procedure (e.g., patient-specific physiologic characteristics, response(s) to surgical events or conditions, etc.).

Some of the goals of continuous monitoring and adjusting can include ensuring that an intended blood flow and oxygenated gas mixture are properly delivered to the patient, ensuring efficiency of perfusion within the patient, and diagnosing possible patient parameter trends/directionality to facilitate correction before a problem occurs. Many different delivery methods, surgeon-specific protocols, monitoring techniques, and patient-management strategies can be employed. These can also vary based on a particular patient, practitioner (e.g., perfusionist), surgeon, or institution. The medical systems disclosed herein can provide an integrated solution of HLM and blood gas monitor functionality in order to achieve the above goals more efficiently.

Figure 1:
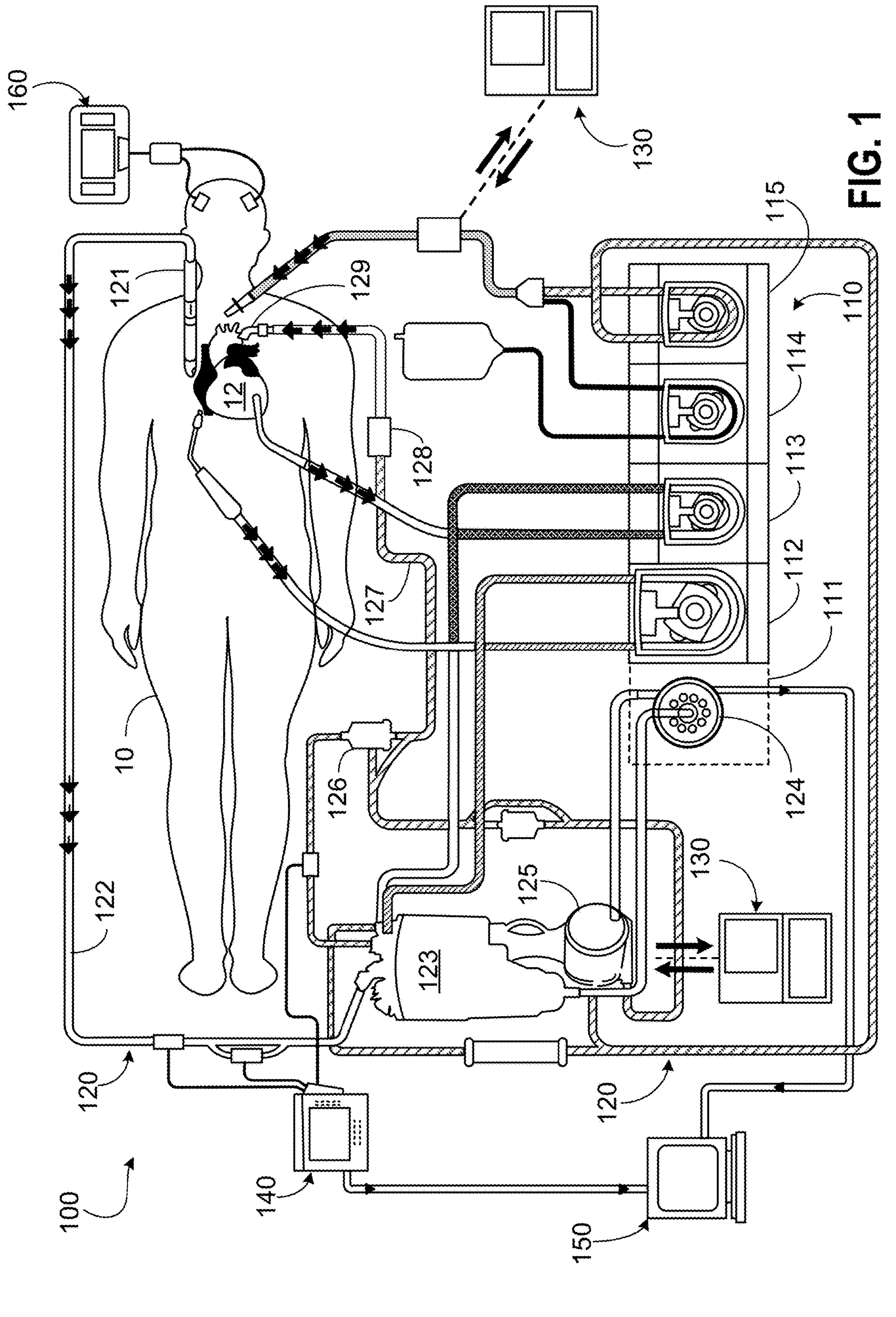
FIG. 1 is a schematic diagram of a patient undergoing open-heart surgery while being supported using a conventional HLM system and extracorporeal circuit.

Now referring to the figures, in FIG. 1, various types of medical procedures can be performed on a patient 10 while the patient 10 is connected to a life-sustaining HLM system 100. In this example, the patient 10 is undergoing open-heart surgery during which the heart 12 and lungs of the patient 10 are temporarily intentionally caused to cease functioning. Because the body of the patient 10 continues to have a metabolic need to receive a supply of circulating oxygenated blood during the medical procedure, however, the HLM system 100 performs such functions. That is, as described further below, the HLM system 100 is connected to the patient 10 and performs the functions of the heart 12 and lungs of the patient 10 so that the patient 10 stays alive and healthy during open-heart surgery.

The HLM system 100 can be used for many different types of medical procedures. For example, the medical procedures for which the HLM system 100 can be used include, but are not limited to, coronary artery bypass grafts, heart valve repairs, heart valve replacements, heart transplants, lung transplants, ablation procedures, repair of septal defects, repair of congenital heart defects, repair of aneurysms, pulmonary endarterectomy, pulmonary thrombectomy, and the like.

The HLM system 100 is typically set up and operated by a specially-trained clinician called a perfusionist. Perfusionists form part of the wider cardiovascular surgical team that includes cardiac surgeons, anesthesiologists, and nurses. During medical procedures using the HLM system 100, the perfusionist is tasked with many responsibilities, not the least of which is ensuring that the patient 10 is kept alive and healthy by operating the HLM system 100 in a manner that maintains blood flow to the patient's tissues, and which regulates levels of oxygen and carbon dioxide in the blood of the patient 10. Other responsibilities of the perfusionist include, but are not limited to, administering blood products, administering anesthetic agents or drugs, measuring selected laboratory values (such as blood cell count), monitoring circulation, monitoring blood gases, surveilling anticoagulation, induction of hypothermia, and hemodilution. The responsibilities of the perfusionist are diverse, dynamic, and critically important to achieving successful outcomes of procedures performed on the patient 10 using the HLM system 100.

In the depicted example, the HLM system 100 includes components and sub-systems such as a HLM 110, an extracorporeal circuit 120, one or more temperature control systems 130, a blood monitoring system 140 (e.g., a CDI® Blood Parameter Monitoring System), a perfusion data management system 150, and a regional oximetry system 160. Some types of procedures that use the HLM system 100 may not require all of the components and sub-systems that are shown. Some types of procedures that use the HLM system 100 may require additional components and/or sub-systems that are not shown.

The extracorporeal circuit 120 is connected to the patient 10, and to the HLM 110. Other systems, such as the temperature control system 130, blood monitoring system 140, and perfusion data management system 150 may also be arranged to interface with the extracorporeal circuit 120. The extracorporeal circuit 120 is connected to the patient 10 at the patient's heart 12. Oxygen-depleted blood (venous blood) from the patient 10 is extracted from the patient 10 at the patient's heart 12 using a venous catheter 121. As described further below, the blood is circulated through the extracorporeal circuit 120 to receive oxygen and remove carbon dioxide. The oxygenated blood is then returned through the extracorporeal circuit 120 to the patient's heart 12 via an aortic cannula 129.

The extracorporeal circuit 120 can include, at least, a venous tube 122 that is coupled to the venous catheter 121, a blood reservoir 123, a centrifugal pump 124, an oxygenator 125, an arterial filter 126, one or more air bubble detectors 128, and an arterial tube 127 that is coupled to the aortic cannula 129. The venous catheter 121 and venous tube 122 are in fluid communication with the venous side of the circulatory system of the patient 10. The venous tube 122 is also in fluid communication with an inlet to the reservoir 123. An outlet from the reservoir 123 is connected by tubing to an inlet of the pump 124. The outlet of the pump 124 is connected by tubing to an inlet of the oxygenator 125. The outlet of the oxygenator 125 is connected by tubing to an inlet of the arterial filter 126. An outlet of the arterial filter 126 is connected to the arterial tube 127. One or more pressure transducers can be located along the arterial tube 127 to detect a heart/lung machine (HLM) system line pressure of the blood in the arterial tube 127, which is measured by the HLM 110 and monitored by the perfusionist. The arterial tube 127 is connected to the arterial cannula 129, which is in physical contact with the heart 12 and in fluid communication with the arterial side of the circulatory system of the patient 10.

Briefly, the extracorporeal circuit 120 operates by removing venous, oxygen-depleted blood from the patient 10 via the venous catheter 121, and depositing the venous blood in the reservoir 123 via the venous tube 122. In some cases, gravity is used to cause the blood to flow or drain from the patient 10 to the reservoir 123. In some cases, vacuum is used to assist the blood to flow from the patient 10 to the reservoir 123. At least some amount of blood is intended to be maintained in the reservoir 123 at all times during the surgical procedure. Otherwise, if the reservoir 123 becomes empty, air could be pumped into the extracorporeal circuit 120, and potentially into the vasculature of the patient 10. Such a result would likely be catastrophic for the patient 10. Accordingly, the perfusionist is tasked with visually monitoring the level of the blood in the reservoir 123. In addition, level detectors can be included in conjunction with the reservoir 123 to issue an alarm in response to detection of low-level conditions within the reservoir 123. Moreover, one or more air bubble detectors 128 can be located at various sites along the extracorporeal circuit 120.

Blood from the reservoir 123 is drawn from the reservoir 123 by the pump 124. While the depicted embodiment includes a one-time use centrifugal pump as the pump 124, in some cases a peristaltic pump of the HLM 110 is used instead. The pressure generated by the pump 124 propels the blood through the oxygenator 125. The perfusionist will adjust the pump 124 to operate as desired, while avoiding operational issues such as negative cavitation that could create micro air in the blood of the extracorporeal circuit 120. In the oxygenator 125, the venous blood is enriched with oxygen, and carbon dioxide is removed from the blood. The now oxygen-rich arterial blood exits the oxygenator 125, travels through the arterial filter 126 to remove emboli, through the arterial tube 160 via the aortic cannula 129. The extracorporeal circuit 120 can also include tubing and other components for facilitating functions such as, but not limited to, drainage of blood accumulating in the heart of the patient 10, providing surgical suction for maintaining visibility of the surgical field, delivery of cardioplegia solution to the heart 12 of the patient 10 during the procedure, measuring blood parameters, removing air from the blood, hemoconcentration, drug addition, obtaining blood samples, heating and cooling of the blood, and the like.

During a surgical procedure using the HLM system 100, various vital signs of the patient 10 are measured and/or monitored. For example, a patient mean arterial pressure ("MAP") may be measured. The MAP of the patient 10 is a parameter that a perfusionist operating the HLM system 100 will monitor in order to ensure that the HLM system 100 is functioning as desired during the surgical procedure. In some cases, the MAP reading is displayed on a screen of an anesthesia system, and/or displayed on the operating room screen. If the MAP of the patient 10 is outside of a desired range, the perfusionist may make adjustments to the HLM system 100 to improve the MAP of the patient 10.

The HLM system 100 also includes the HLM 110. The HLM 110 is a complex system that includes multiple pumps, monitors, controls, user interfaces, alarms, safety devices, and the like, that are all monitored and operated/adjusted by the perfusionist during a surgical procedure. For example, the depicted HLM 110 includes an arterial pump 111 (which can be a drive system for a disposable centrifugal pump 124 as shown, or a peristaltic pump), a suction pump 112, a vent/drainage pump 113, a cardioplegia solution pump 114, and a cardioplegia delivery pump 115. The HLM 110 can also include, or be interfaced with, devices such as a tubing occluder, gas blender, hemoconcentrator, and the like. The parameters of the HLM 110, such as the rotational speed and other parameters of each of the pumps, are set and adjusted by the perfusionist. For example, the speed of the arterial pump 111 is adjusted to maintain a desirable level of blood in the reservoir 123, and to provide a requisite level of blood circulation within the patient 10.

The HLM system 100 also includes one or more temperature control systems 130. In a first aspect, the temperature control system(s) 130 is/are used to heat and cool the patient's blood in the oxygenator 125 via a heat exchanger. Additionally, the temperature control system(s) 130 is/are used to heat and cool the cardioplegia solution being delivered to the heart 12 of the patient 10. In general, the temperature control system(s) 130 is/are used in cooling modes during the procedure (to reduce metabolic demands), and subsequently used to warm the blood and/or cardioplegia solution when the surgical procedure is nearing its end. The perfusionist is tasked with monitoring and adjusting the temperature control system(s) 130 as needed during the surgical procedure.

The HLM system 100, as depicted, also includes the blood monitoring system 140. The blood monitoring system 140 uses one or more blood gas sensors (e.g., venous shunt sensor, arterial shunt sensor, H/S cuvette, etc.) located at various locations along the extracorporeal circuit 120 (e.g., the venous tube 122, the arterial tube 127, etc.) to monitor the arterial and/or venous extracorporeal blood of the patient 10 during the surgical procedure. The blood monitoring system 140 can also use one or more other blood gas sensors, which can include an air detector, a bubble sensor, an arterial optical fluorescent sensor, a venous optical fluorescent sensor, an arterial optical reflective sensor, a venous optical reflective sensor, a hematocrit level sensor, and/or a hemoglobin sensor. Parameters being monitored can include, but are not limited to, pH, $pCO_2$, $pO_2$, K+, temperature, $SO_2$, hematocrit, hemoglobin, base excess, bicarbonate, oxygen consumption and oxygen delivery. The perfusionist is tasked with monitoring the blood monitoring system 140 during the surgical procedure. In some cases, the perfusionist will need to adjust other components or subsystems of the HLM system 100 in response to readings from the blood monitoring system 140.

The HLM system 100, as depicted, also includes the perfusion data management system 150 and the regional oximetry system 160. These systems can also be used by the perfusionist to monitor the status of the patient 10 and/or the status of the HLM system 100 during surgical procedures.

From the above description, it can be observed and understood that the perfusionist is tasked with a vast amount of very important responsibilities during a surgical procedure using the conventional HLM system 100. Accordingly, the HLM systems described herein provide innovative systems and techniques to assist the perfusionist.

Figure 2:
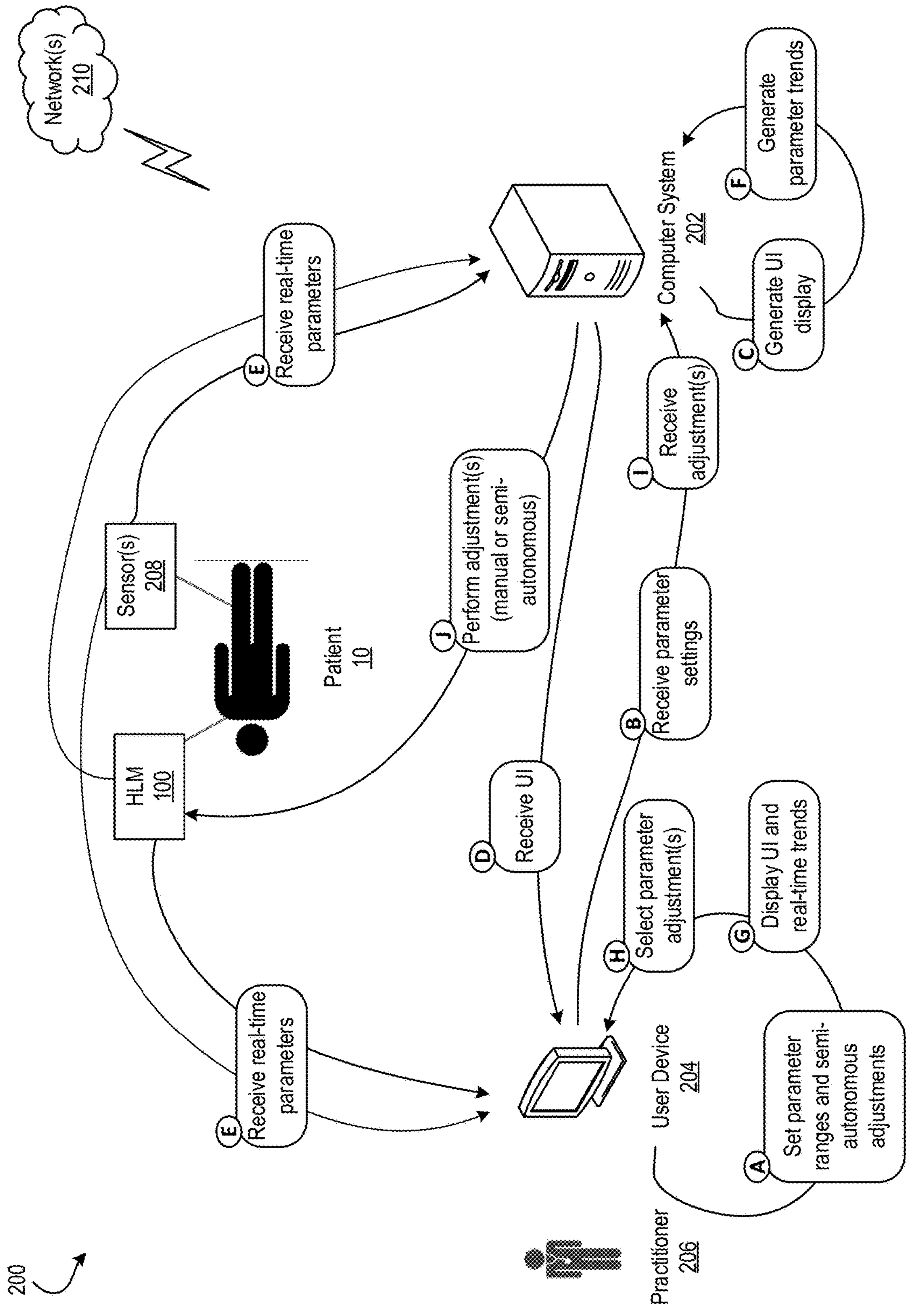
FIG. 2 is a schematic diagram of an example monitoring and control system used during a medical procedure.

FIG. 2 is a schematic diagram of an example monitoring and control system used during a medical procedure 200. The procedure 200 can include the patient 10 and a practitioner 206. The practitioner 206 can be a perfusionist or other professional who performs the procedure 200 and/or portions of the procedure 200. The patient 10 can be hooked up or in communication with the HLM (e.g., HLM system 100), as depicted and described throughout this disclosure. Sensor(s) 208 can also be attached to the patient 10 or the extracorporeal circuit. The sensor(s) 208 can further be in communication with the HLM system 100 and/or any other devices used during the procedure 200. The sensor(s) 208 can capture real-time conditions of the patient 10, the HLM system 100, and parameters that are being monitored during the procedure 200.

The practitioner 206 can use a user device 204 to monitor conditions or parameters of the patient 10, the HLM system 100, and other devices used during the procedure 200. In some embodiments, the user device 204 is part of the HLM system 100, or physically attached thereto. In some embodiments, the user device 204 can be separate from the HLM system 100. In some embodiments, the user device 204 can be a mobile computing device, such as a smartphone or tablet. The user device 204 can also be a computer or laptop. The user device 204 can have a user interface (e.g., touchscreen, monitor, etc.) configured to display monitored conditions and parameters in real-time. The user device 204 can also have one or more input devices configured to receive adjustments from the practitioner 206. The practitioner 206 can make adjustments to any one of the conditions and parameters by providing input to the user device 204.

The user device 204 can be in communication with a computer system 202 (e.g., monitoring and control system). In some embodiments, the computer system 202 is part of the HLM system 100. In some embodiments, the user device 204 is part of the computer system 202. Moreover, the computer system 202 can include one or more input devices and/or displays.

The computer system 202 can be configured to provide the user device 204 with a user interface that displays monitored conditions and parameters. In some implementations, the computer system 202 and the user device 204 can be the same system. In other implementations, the computer system 202 and the user device 204 can be remote from each other. The computer system 202 can also facilitate one or more adjustments made or suggested by the practitioner 206 during the procedure 200. Therefore, the computer system 202 can also be in communication with the HLM system 100, the sensor(s) 208, and any other devices that are used during the procedure 200. Communication between one or more components (e.g., the user device 204, the HLM 110, the sensor(s) 208, and the computer system 202) can be wireless and/or wired via network(s) 210.

Still referring to FIG. 2, before the procedure 200 begins, the practitioner 206 can set parameter ranges and semi-autonomous adjustments at the user device 204 (A). The user device 204 can provide a display to the practitioner 206, prompting the practitioner 206 to set values for each of the parameters that will be monitored during the procedure 200. The practitioner 206 can also be prompted to input desired adjustments to the parameters that the practitioner 206 may want implemented during the procedure 200 if the parameters stray from the practitioner-defined parameter ranges. In other words, before the procedure 200, the practitioner 206 can indicate what actions (e.g., pre-defined adjustments) can be taken should any of the parameters exceed or fall below ideal ranges that the practitioner 206 also defines before the procedure 200. Then, during the procedure 200, if any of the parameters do in fact stray outside of the practitioner-defined ranges, the practitioner 206 can select and perform one of the pre-defined adjustments. Such adjustments can be performed manually by the practitioner 206. Such adjustments can also be performed semi-autonomously by the computer system 202.

The practitioner 206 can set parameter ranges and semi-autonomous adjustments that apply generally to all similar procedures or a specific practice area. Therefore, regardless of which patient undergoes the procedure 200, the same parameter ranges and semi-autonomous adjustments can be applied to the procedure 200. This can be beneficial for the practitioner 206 to perform all procedures the same way, which can improve patient safety and overall procedure outcomes. Moreover, using the same parameter ranges and semi-autonomous adjustments in a specific practice area can be advantageous for the computer system 202 to more accurately predict and/or generate parameter trend analysis. In other examples, the practitioner 206 can set parameter ranges and semi-autonomous adjustments per procedure per patient. In other words, first and second patients can undergo the same procedure. However, the practitioner 206 can set different parameter ranges and adjustments for each of the patients. This can be beneficial where the patients have different health conditions or sensitivities.

Next, the computer system 202 can receive the parameter settings from the user device 204 (B). These parameter settings can be one or more of the practitioner-defined parameter ranges and/or semi-autonomous parameter adjustments.

Based on the received parameter settings, the computer system 202 can generate one or more user interface displays (C). For example, the computer system 202 can generate interactive/selective options on a user interface, wherein each of the selective options correlates to a semi-autonomous adjustment that the practitioner 206 defined at the user device 204. In other words, if the practitioner 206 defined an adjustment to increase blood flow through the extracorporeal circuit in the HLM system 100, the computer system 202 can generate a button that, when clicked on by the practitioner 206 during the procedure 200, can automatically cause the blood flow to be increased through the circuit. As another example, the computer system 202 can also generate one or more graphs or other depictions for each of the parameters that the practitioner 206 defined at the user device 204.

The generated user interface display can be received at the user device 204 (D). In other words, the user interface can be displayed on the user device 204 during the procedure 200. The display can be updated during the procedure 200 to reflect real-time changes in parameters, parameter trends, and/or conditions of the patient 10. The display, as depicted and described throughout this disclosure, can provide information for each of the monitored or defined parameters on a single user interface. As a result, in some embodiments the practitioner 206 can monitor all parameters during the procedure 200 concurrently. In other implementations, the practitioner 206 can switch between multiple different user interface displays/screens. Each of the user interface displays/screens can be related to a particular parameter. Each of the user interfaces can be related to a subset of all of the practitioner-defined parameters.

In some cases, consolidating the parameters into a singular user interface display can be advantageous. This is because the practitioner 206 can more easily and continuously monitor all parameters during the procedure 200. With real-time updates, the practitioner 206 can also more quickly and accurately respond to any undesired changes in the parameters.

In some implementations, the user device 204 can display a first user interface (e.g., GUI) for setting parameters and a second user interface (GUI) for viewing the real-time changes to the parameters, as described throughout this disclosure. Thus, the first and second user interfaces can be resident on the user device 204. In some implementations, one or more of the first and second user interfaces can be located or otherwise displayed on another user device and/or computing system that is separate and/or different from the user device 204.

The user device 204 can receive real-time parameter information from the HLM system 100 and/or the sensor(s) 208 during the procedure (E). The computer system 202 can also receive real-time parameter information from the HLM system 100 and/or the sensor(s) 208 (E). Based on the real-time parameter information, the computer system 202 can generate parameter trends (F). For example, the computer system 202 can generate graphs depicting a trend analysis of each of the monitored parameters. The graphs can indicate past, current, and projected trends of the monitored parameters. The graphs can also indicate past, current, and projected trends of the monitored parameters relative to the practitioner-defined parameter ranges.

The generated parameter trends can be provided from the computer system 202 to the user device 204. Therefore, the parameter trends can be displayed at the user interface (G). Thus, the user interface can be dynamically updated as real-time parameter information is received (E) and parameter trends are generated (F). In some implementations, the user device 204 can determine and generate the parameter trends. The user device 204 can also display the real-time parameter information that is received from the HLM system 100 and/or the sensor(s) 208 (G). For example, the user device 204 can update the user interface with parameter values that are sensed in real-time by the sensor(s) 208. That user interface can also be updated to reflect the parameter trends generated by the computer system 202 (F). Thus, the user interface can display both the present or current parameter values as well as the projected parameter trends. As described throughout this disclosure, data can be extrapolated from trending parameter values and used to predict conditions of the patient 10 during the procedure 200.

Current trend lines can also be determined for the parameters based on historic data. The current trend lines can be informative about where and how parameters are trending. In some implementations, the projected parameter trends can be used by the practitioner 206 to make one or more adjustments during the procedure 200. For example, the practitioner 206 can view trending parameters to determine a dropping rate over time for a venous reservoir to then control an arterial pump. Thus, the projected parameter trends can be advantageous to improve patient safety and control different parameters and/or system components during the procedure 200. Furthermore, providing all this information in one location can assist the practitioner in continuously monitoring and controlling parameters during the procedure 200.

As all this information is displayed to the practitioner 206 at the user device 204, the practitioner can choose whether or not to make any adjustments to affect the monitored parameters. For example, if one of the parameters is projected to trend out of the practitioner-defined range for that parameter, then the practitioner 206 can select one of the practitioner 206's pre-defined parameter adjustments from the user interface (H). As mentioned, the pre-defined parameter adjustments can be displayed in the user interface as a selectable option, such as a button.

When the practitioner 206 selects one or more of the pre-defined parameter adjustments, the computer system 202 can receive the adjustment from the user device 204 (I). In some implementations, the practitioner 206 can select more than one pre-defined parameter adjustment. Selections by the practitioner 206 can be communicated and performed simultaneously by the computer system 202.

The parameter adjustment(s) can then be performed (J). In some embodiments, the parameter adjustment can be semi-autonomously performed by the computer system 202. In other words, the practitioner 206 defined the adjustment before the procedure 200 began. When the practitioner 206 selected the pre-defined parameter adjustment during the procedure 200, the computer system 202 received instructions to execute the adjustment. Therefore, the practitioner 206 maintains control of what type of adjustments occur during the procedure 200. In some embodiments, the computer system 202 does not predict or suggest to the practitioner 206 what adjustment(s) to make. Alternatively, in some embodiments the computer system 202 does suggest to the practitioner 206 what adjustment(s) to make.

In other examples, the adjustment(s) can be performed manually by the practitioner 206. The practitioner 206 can also override a semi-autonomous adjustment by selectively controlling one or more buttons or other physical components of the user device 204, the HLM system 100, and/or any other device that is used during the procedure 200. For example, the practitioner 206 may have established a pre-defined parameter adjustment before the procedure 200 that required increasing pressure through a particular portion of the extracorporeal circuit by a first value. During the procedure 200, the practitioner 206 may still want to perform that adjustment but increase pressure through the particular portion of the extracorporeal circuit by a second value instead of the first value. The second value can be greater or less than the first value. Therefore, the practitioner 206 can manually take control and operate one or more physical buttons to adjust the pressure by the second value. This can be a manual or semi-manual performance of a pre-defined adjustment.

The user device 204 and the computer system 202 can continue to receive real-time parameter information during the procedure 200, after such one or more adjustments have been made. As a result, the practitioner 206 can continuously monitor the parameters and make any necessary adjustments throughout the procedure 200.

Figure 3:
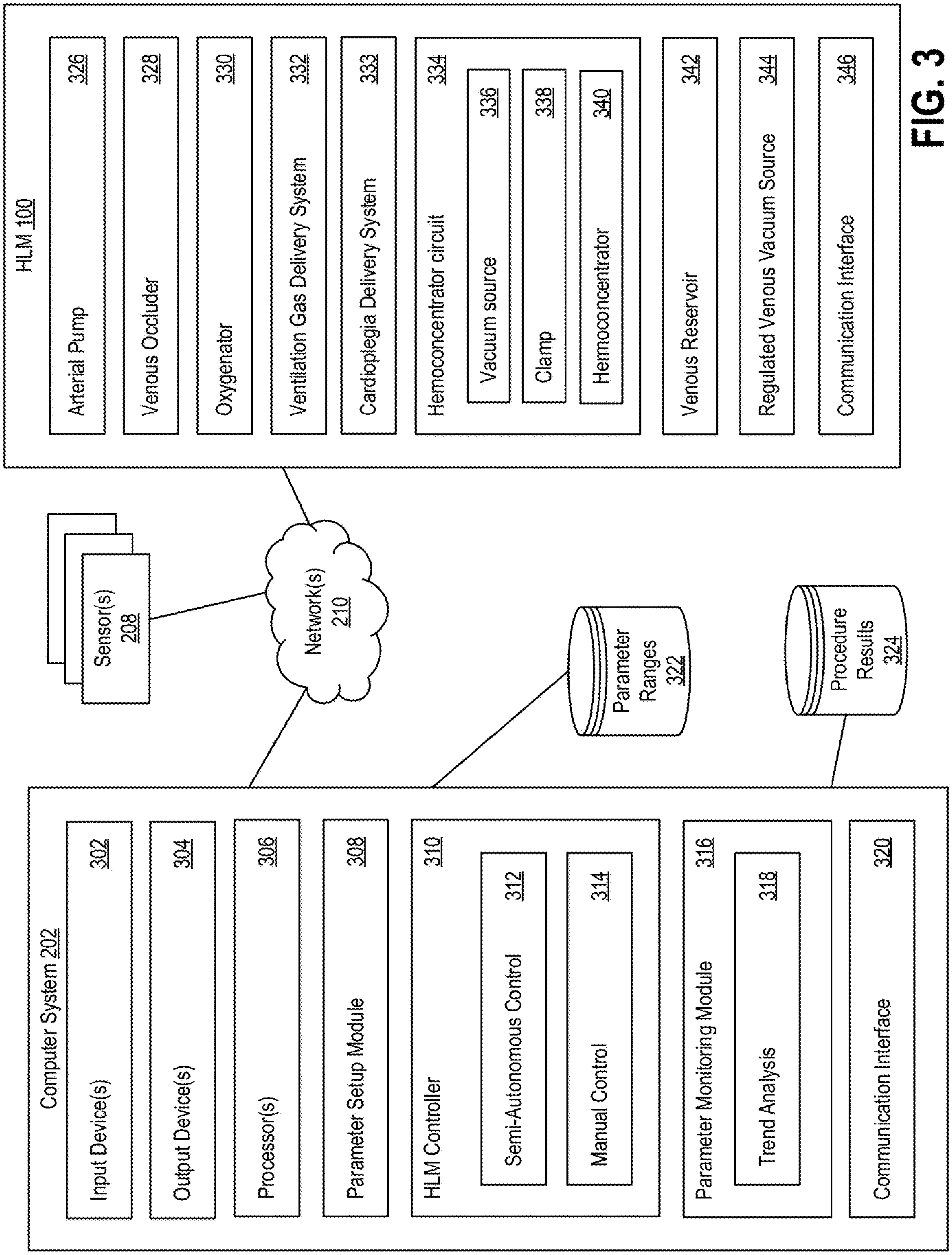
FIG. 3 is another schematic diagram of the example monitoring and control system described herein.

FIG. 3 is a schematic system diagram of the example monitoring and control system described herein. As depicted, the computer system 202 (e.g., the monitoring and control system), the sensor(s) 208 and the HLM system 100 can be in communication (e.g., wired and/or wireless) via the network(s) 210. In some embodiments, the user device 204 depicted and described in reference to FIG. 2 can be separate from the computer system 202. As depicted in FIG. 3, in some embodiments the user device 204 and the computer system 202 can be portions of the same system.

The computer system 202 includes input device(s) 302, output device(s) 304, processor(s) 306, a parameter setup module 308, an HLM controller 310, a parameter monitoring module 316, and a communication interface 320. The input device(s) 302 can be one or more touchscreen displays, microphones, keyboards, mouse, or any other device(s) used to provide input to the computer system 202. The practitioner 206 can provide/establish parameter settings, ranges, and/or adjustments to the computer system 202 via the input device(s) 302. The output device(s) 304 can be any type of display used to provide output from the computer system 202. For example, the display can be a screen on a mobile device such as a smartphone, laptop, tablet, or other computer. The output device(s) 304 can output a user interface display that provides real-time parameter information including graphical depictions of trending parameters and selectable options for parameter adjustments.

The processor(s) 306 can be configured to perform one or more operations by the computer system 202 as described herein. Moreover, the communication interface 320 can be configured to provide for communication (e.g., wired and/or wireless) between the computer system 202, the sensor(s) 208, and/or the HLM system 100 via the network(s) 210.

Still referring to the computer system 202, the parameter setup module 308 can be configured to receive input from the practitioner 206 regarding parameters to be monitored during a medical procedure. As described throughout this disclosure, the practitioner 206 can identify which parameters to monitor, set parameter ranges, and define semi-autonomous adjustments. These inputs can be received by the computer system 202 and stored in a parameter ranges database 322. The parameter ranges database 322 can store practitioner-defined parameter ranges and semi-autonomous adjustments from past as well as present. As a result, user interfaces can be more quickly generated by the computer system 202 (e.g., at the parameter setup module 308). Moreover, the generated user interfaces can be stored in the parameter ranges database 322. These stored user interfaces can then be used by the computer system 202 in generating user interfaces for other and/or similar procedures.

The parameter setup module 308 can access these inputs from the parameter ranges database 322. The module 308 can use these inputs to generate a user interface display. The user interface display can reflect the parameters that the practitioner identified for monitoring as well as graphical depictions for each of the parameters, and selectable options for each of the practitioner-defined semi-autonomous adjustments. The user interface can then be displayed by the output device(s) 304. In other examples, such as in FIG. 2, the user interface can be transmitted from the computer system 202 to the user device 204 for display.

The HLM controller 310 can have a semi-autonomous control 312 and a manual control 314. During a procedure, if the practitioner selects one of the pre-defined adjustments, the HLM controller 310 can be actuated. Thus, where the practitioner selects an adjustment that requires the computer system 202 to perform the adjustment, the semi-autonomous control 312 can be activated. For example, where the adjustment requires a valve to be opened or closed a predetermined amount, the semi-autonomous control 312 can cause the valve to be opened or closed the predetermined amount. Where the practitioner selects an adjustment but the practitioner performs the adjustment themselves (e.g., by physically turning or actuating buttons on the user device 204 or the computer system 202), the manual control 314 can be activated.

The parameter monitoring module 316 can include trend analysis 318. The parameter monitoring module 316 can receive real-time parameter conditions from the sensor(s) 208 and/or the HLM system 100. Based on those received values, the trend analysis 318 can generate graphical depictions of each of the monitored parameters. The graphical depictions can indicate a past, present, and projected trend of the parameters. The graphical depictions can also indicate whether the parameter trends are within the practitioner's pre-defined ranges. The real-time parameter conditions and the generated graphical depictions/trends can be outputted to the practitioner in the user interface display via the output device(s) 304.

Once the procedure is completed, procedure results can be stored in the procedure results database 324. The database 324 can also store generated graphical depictions and trends of the monitored parameters. The information stored in the database 324 can be used by the computer system 202 to more accurately generate and predict parameter trends in other procedures. Thus, the computer system 202 can employ machine learning and/or deep learning to train one or more algorithms or components (e.g., the parameter monitoring module 316) off the data stored in the procedure results database 324.

The HLM system 100 can include an arterial pump 326, a venous occluder 328, an oxygenator 330, a ventilation gas delivery system 332, a cardioplegia delivery system 333, a hemoconcentrator circuit 334, a venous reservoir 342, a regulated venous vacuum source 344, and a communication interface 346. The arterial pump 326 and venous occluder 328 can control flow of blood between the HLM system 100 and a patient. Furthermore, one or more of the sensors 208 can be configured to any one or more components of the HLM system 100 to monitor in-line blood gas, flow, pressure, temperature, etc.

The cardioplegia delivery system 333 can include a cardioplegia pump, similar to the arterial pump 326. A cardioplegic solution high in potassium can be used to arrest the heart of the patient undergoing cardiopulmonary bypass. The solution can be delivered in various ratios and concentrations of drug constituents via the system 333 to enable a diastolic arrest and have a continuously quiescent heart. Serum potassium can monitored by an in-line blood gas analyzer. The serum potassium can be evaluated for additional cardioplegia administration, dependent upon procedural cadence of a need to increase serum potassium to keep myocardial arrest. Conversely, at a termination of cardiopulmonary bypass, the potassium level can be tailored to be within a narrow range to support electric activity of the myocardial cell.

User control of the potassium can include user-selectable limits (e.g. target, range, alert/alarm thresholds) that can be utilized for semi-automated control of the needed level. The semi-automated control can include the changes that can be made to a ratio of blood solution to potassium crystalloid solution, volume of cardioplegia, changes in hemoconcentration and various pharmacological protocols.

Moreover, the system 333 can be configured to analyze serum potassium levels versus (high) patient set points. The system 333 can evaluate a set of cardioplegia ratios and volumes, level detection points, and EKG electrical activity. The system 333 can also suggest increases or decreases in blood to crystalloid ratio for cardioplegia administration, hemoconcentration or an increase and/or decrease in effluent rate, and/or administration of protocolized insulin and sodium bicarbonate, or renal diuretic. In some implementations, the system 333 can be the same as or part of the computer system 202. In some implementations, the system 333 can be different than the computer system 202.

The ventilation gas delivery system 332 can be used to control gas flow rate and concentration (e.g., a mixture of air, oxygen) delivered to the oxygenator 330. Blood flows through the oxygenator 330. The system 332 can be used to add O2 and/or ambient air to physically control O2, CO2, and sweep rate (e.g., respiratory rate) to the blood and the patient when the blood is in the oxygenator 330. The system 332 can be manually controlled by the practitioner and/or semi-autonomously controlled by the computer system 202, as described herein. For example, the practitioner can define an adjustment to a level or concentration of a mixture of gases to be added to the blood in the oxygenator 330. During the procedure, the practitioner can select this adjustment to be performed, which prompts the computer system 202 to control the ventilation gas delivery system 332 and provide the level or concentration of the mixture of gases that the practitioner defined before the procedure.

Moreover, the ventilation gas delivery system 332 can determine and monitor expired carbon dioxide measurement (expiredCO2) and anesthetic gas in the oxygenator 330 exhaust gas. The system 332 can convert the expiredCO2 to an independent volumetric number (VCO2) and/or a patient body surface area indexed value (VCO2i). Measurement of expired CO2 and evaluation of the VCO2 can add to efficiency of perfusion, for carbon dioxide production is a byproduct of cellular metabolism from oxygen delivery to end tissues. The measurement of carbon dioxide production (VCO2, expiredCO2, VCO2/DO2 ratio) can aid in control of adequate oxygen delivery to the patient. User selectable carbon dioxide variables (ranges) can trigger adjusted increase in oxygen delivery to end tissues, or a decrease in metabolic demands.

An in-line blood gas monitoring system (e.g., the blood monitoring system 140 shown in FIG. 1) can also be used to provide continuous, real-time measurements of various patient parameters to monitor and maintain optimal metabolic performance of the patient. Regulation of blood gas parameters can be beneficial to avoid the negative outcomes linked to sub-optimal blood gas parameter control. For example, monitoring blood gas parameters can provide improvements in cardiac function, renal function, pulmonary function, cerebral function, transfusion requirements (e.g., reducing a need for transfusions), ventilator requirements (e.g., reducing an amount of time on a ventilator), ICU stays (e.g., reducing a number of days in ICUs), and/or post-operative hospital stays (e.g., reducing a number of days for hospital stays).

The hemoconcentrator circuit 334 further includes a vacuum source 336, a clamp 338 (e.g., clamping mechanism), and a hemoconcentrator 340. The circuit 334 can be used to remove water from the blood. The clamp 338 can be used to control flow of shunted arterial blood through the hemoconcentrator 340 and back to the venous reservoir 342 as a means of increasing a hemoglobin number (e.g., decreasing hemodilution) in the arterial blood provided to the patient. As depicted and described herein, opening and closing the clamp 338 can be automated, or performed semi-autonomously by the computer system 202. The regulated venous vacuum source 344 can be used to supplement venous blood flow into the venous reservoir 342. Finally, the communication interface 346 is configured to facilitate communication between the HLM, the sensor(s) 208, and/or the computer system 202 via the network(s) 210.

Moreover, arterial blood flow can be measured with a flow probe. The flow through a cardiopulmonary bypass circuit can be measured anywhere in the circuitry, using one or more sensors such as the sensor(s) 208. While the most common area to measure flow is the arterial flow being delivered to the patient, there are other areas within the circuit that a practitioner may choose to monitor flow (venous, cardioplegia, modified ultrafiltration, selective perfusion to an area of the patient, etc.). A determination of flow can be done with either a calculated flow rate when a roller pump is employed to produce forward flow, or a measured flow rate with a flow probe when a centrifugal pump is used. The monitored flow can be displayed at the output device(s) 304 of the computer system 202. The monitored flow can indicate the flow rate of oxygenated arterial blood delivered to the patient. Estimated cardiac output can also reflect a patient's Body Surface Area (BSA) and the Metabolic demands of such patient (Cardiac Output=BSA×Cardiac Index). These are parameters that the practitioner can also use to determine what other adjustments may be needed to improve procedure outcomes.

As described throughout, the HLM system 100 and the computer system 202 can be the same system. The HLM system 100 and the computer system 202 can also be remote from each other. Similarly, the sensor(s) 208 and/or the user device 204 can be part of or integrated with any one of the HLM system 100, the computer system 202, or a combination thereof. The sensor(s) 208 and/or the user device 204 can also be remote from any one of the HLM system 100, the computer system 202, or a combination thereof.

FIG. 4 is a flowchart of an example process 400 to monitor and control parameters for a medical procedure. The process 400 can be performed by the computer system 202, as described herein. The process 400 can also be performed by one or more other computer systems.

User-defined parameter settings can be received in 402. For example, the parameter setup module 308 of the computer system 202 can receive the settings (e.g., refer to FIG. 3). A practitioner can input the settings into an input device (e.g., the input device(s) 302 of the computer system 202 in FIG. 3) and/or a user device (e.g., the user device 204 in FIG. 2). As described throughout this disclosure, the practitioner can indicate which parameters they would like to monitor and ranges that those parameters should stay within during the procedure. The practitioner can also indicate one or more adjustments that can be taken should the monitored parameters stray from the user-defined ranges during the procedure. The practitioner can also indicate how they would like the user interface to be displayed. For example, the practitioner can select and place different displays and controls on the user interface. The practitioner can choose to display a graph or trend lines for only some of the parameters. The practitioner can also choose how many parameters to display on the user interface and what control options to have for each of the parameters. The practitioner can select primary and/or secondary display features. The practitioner can also indicate numeric and trending formats for each of the monitored parameters. Moreover, the practitioner can set alarms or alerts to go off whenever a parameter trends towards one of the user-define parameter ranges.

The user-defined parameter settings can be received before the procedure. These settings can be generally applicable to a practice area or type of procedure. In some examples, these settings can be applicable to a particular patient and/or a particular procedure.

A user interface (UI) display can be generated in 404. For example, generating the display can be performed by the parameter setup module 308 and/or the parameter monitoring module 316 of the computer system 202 (e.g., refer to FIG. 3). The user interface display can be generated based on the practitioner-defined settings in 402. Generating the UI can include creating graphs for each monitored parameter. The graphs can include indicators for the user-defined parameter ranges. Generating the UI can also include creating selectable options, such as buttons, for each of the user-defined adjustments. The generated graphs and selectable options can be presented in a single user interface display. This can be advantageous for the practitioner to monitor all parameters at the same time. In other words, the practitioner would not have to look at different devices or displays to monitor each of the parameters during the procedure. Moreover, this configuration is advantageous because the practitioner can identify how parameters trend relative to each other. As a result, the practitioner can more adequately and accurately respond to changes in any of the monitored parameter conditions during the procedure.

In some examples, additional user interface displays can be generated. Additional UIs can be generated if, for example, the practitioner indicates in the user-defined settings (402) that the practitioner wants certain parameters grouped together in a display. Additional UIs can also be generated if, for example, the user-defined settings (402) indicate that many parameters are going to be monitored. When many parameters are monitored, graphs and selectable options for each of the parameters may crowd the UI display, thereby making it challenging or confusing for the practitioner to monitor all the parameters from the same display. Therefore, one or more parameters can be grouped together into different UI displays. The computer system 202 can determine which parameters to group together. In other examples, the practitioner can indicate in the user-defined settings (402) which parameters to group together. In yet other examples, the computer system 202 can generate a single UI display and provide selectable options for each of the monitored parameters. Therefore, the practitioner can click on any one of the selectable options to view information about the monitored parameters.

Real-time parameter conditions can be received in 406. In other words, during the procedure, parameter conditions can be continuously sensed by one or more sensors and/or devices (e.g., refer to FIG. 2). As depicted in reference to FIG. 3, the parameter conditions can be received by the parameter monitoring module 316. One or more flow sensors can be placed on components of an in-line blood flow circuit to measure a flow of blood from the patient to the HLM and back to the patient. 402-404 can be performed before the procedure begins. In some examples, the UI display can be generated (404) during the procedure and then continuously updated for a duration of the procedure.

Parameter trends can be generated based on the user-defined settings and the real-time parameter conditions in 408. The parameter monitoring module 316, and specifically the trend analysis 318, of the computer system 202 can generate parameter trends (e.g., refer to FIG. 3). For example, graphs can be generated for each of the monitored parameters, as described in further detail below (e.g., refer to FIGS. 10, 12, 14). A graph can include a trend line that indicates past sensed conditions, present sensed conditions, and projected sensed conditions of the monitored parameter. The projected sensed conditions can be determined based on an analysis of the past sensed conditions, the real-time present sensed conditions, and any other parameters that can impact the projected trend of the monitored parameter. The graph can also include indicators or markers of the user-defined parameter ranges. Therefore, the aggregate graph can depict the parameter trend amidst the user-defined parameter ranges, which can assist the practitioner in determining or identifying when the monitored parameter may surpass one of the defined ranges and cause harm or other implications during the procedure.

For a duration of the procedure, the parameter trends generated in 408 can be continuously updated to reflect changes in sensed real-time parameter conditions (406). This can be advantageous for the practitioner to more accurately monitor and respond to changes in the parameters during the procedure.

The generated parameter trends can be transmitted to the user device for display in 410 (e.g., the user device 204 in FIG. 2). In other words, the UI display that was generated in 404 can be updated to reflect the generated parameter trends. This updated UI display can be transmitted to and outputted at the user device. In implementations where the computer system 202 and the user device are the same system, the generated parameter trends can be outputted for display on an output device, such as a touchscreen, LCD monitor, or other type of display or screen (e.g., the output device(s) 304 of the computer system 202 in FIG. 3).

During the procedure, parameter adjustments can be received in 412. For example, the practitioner can monitor the parameters at the user device and decide to adjust a flow rate for one of the parameters through one or more components of the in-line blood flow circuit. The practitioner can make this determination based on seeing that the parameter trend is projected to surpass the user-defined ranges in a certain amount of time. The practitioner can provide input to the computer system 202 (e.g., by selecting a selectable option on the user interface display or pressing/actuating a physical button on the user device; using the input device(s) 302 of the computer system 202 in FIG. 3 and/or the user device 204 in FIG. 2) that indicates that a parameter adjustment needs to be made. The HLM controller 310 of the computer system 202 can receive the practitioner's input (e.g., refer to FIG. 3). In some examples, the practitioner can select one of the practitioner's user-defined adjustments. In other examples, the practitioner can instigate a parameter adjustment that the practitioner did not define before the procedure began.

The adjustment(s) can be transmitted to the HLM in 414. In some examples, the adjustment(s) can be manually performed by the practitioner. In other examples, the adjustment(s) can be semi-autonomously performed by the computer system 202 or any other system. The semi-autonomous control 312 of the HLM controller 310 can perform the semi-autonomous adjustment(s) (e.g., refer to FIG. 3). The manual control 314, on the other hand, can be actuated when the practitioner performs the adjustment(s) on their own (e.g., refer to FIG. 3).

A semi-autonomous adjustment can be made when the practitioner selects one of the selectable options on the UI display for a user-defined adjustment. Once the practitioner selects the option (e.g., a button), the computer system 202 can immediately perform the adjustment. Real-time parameter conditions can be sensed and received again (406) and the UI display can be updated to reflect changes to the parameter based on the semi-autonomous adjustment.

A manual adjustment can be made when the practitioner changes any of the parameters during the procedure. For example, the practitioner can use a physical button or dial to increase or decrease blood flow rate through a portion of the in-line blood flow circuit. As another example, the practitioner can in put different values for the blood flow rate into the user device using an input device (e.g., touchscreen, keyboard, mouse, etc.). The practitioner's manual adjustment(s) can override any semi-autonomous adjustments such that the practitioner can maintain control of the parameters during the procedure. The practitioner may choose to perform a manual adjustment when the practitioner realizes that a pre-defined adjustment may not be applicable to real-time sensed conditions or projected sensed conditions of a parameter. In other words, the pre-defined adjustment may not account for how the parameter actually trends during the procedure. Having the ability to perform semi-autonomous and manual adjustments during the procedure can help the practitioner maintain control over procedure decision-making, ensure patient safety, and improve procedure outcomes.

The user-defined settings and procedure results can be stored in 416. For example, the user-defined settings can be stored in the procedure ranges database 322 and the procedure results can be stored in the procedure results database 324 as depicted in FIG. 3. In some implementations, the user-defined settings can be stored once the settings are received in 402. The procedure results can include trends or graphs of each of the monitored parameters for the duration of the procedure. The procedure results can also include information about what adjustments were made and the effects of such adjustments on parameter trends.

Optionally, the computer system 202 can use the stored user-defined settings and/or procedure results in order to improve one or more components or algorithms of the system 202. For example, the trend analysis 318 of the parameter monitoring module 316 can be trained using the procedure results such that the trend analysis 318 can more accurately predict projected parameter trends. By predicting more accurate projected parameter trends, fewer parameter adjustments may need to be made during the procedure. As a result, patient safety and procedure outcomes can be improved.

In other implementations, the practitioner can also review the stored user-defined settings and/or procedure results so that the practitioner can improve their practice. For example, the practitioner can determine that they should create different adjustments based on procedure results where other adjustments were implemented.

In yet other implementations, the stored user-defined settings and/or the procedure results can be used by the computer system 202 to more quickly and efficiently generate user-friendly, readable UI displays. In other words, the computer system 202 can use stored user-defined settings to provide similar UI displays to different practitioners who are performing the same procedure. This can streamline the process of generating UI displays and ensure that standard, effective practices are used in the same practice area. As a result, patient safety and procedure outcomes can be improved across the board in the practice area.

404-416 can be repeated for a duration of the procedure. For example, when parameter adjustments are made in 414, the UI display can be generated and/or updated (404), real-time parameter conditions can be received (406), parameter trends can be updated to reflect the adjustments and real-time conditions (408), and these updated trends can be displayed at the user device (410). The practitioner may optionally continue performing parameter adjustments for the duration of the procedure (412-414) based on the continuously monitored real-time parameter conditions.

Figure 5A:
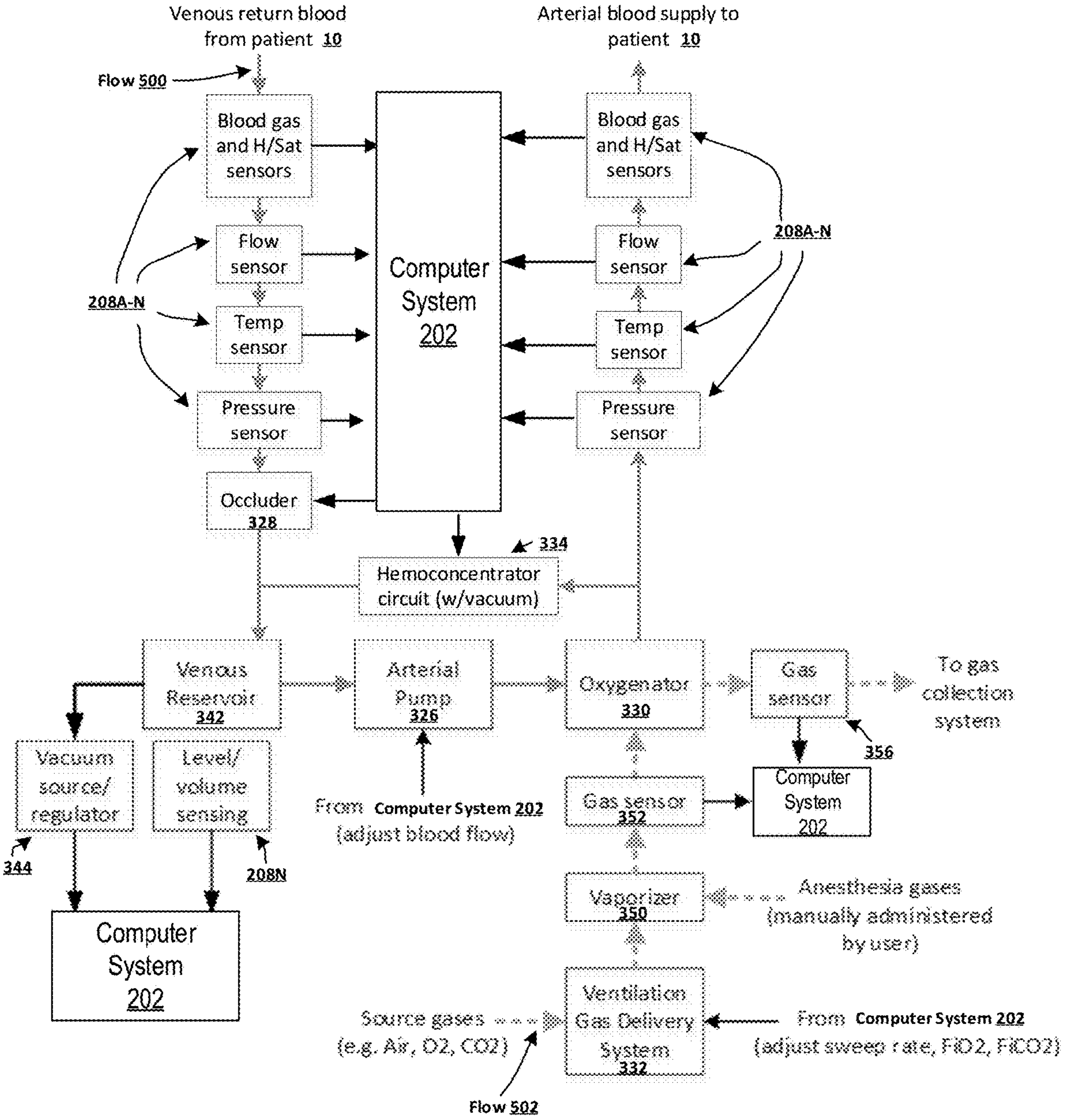
FIG. 5A is a block diagram of the example monitoring and control system during a procedure.

FIG. 5A is a block diagram of the example monitoring and control system during a procedure. Flow 500 indicates a flow of blood between components of the HLM system 100 and the patient 10. Flow 502 (represented by a dashed line in FIG. 5A) indicates a flow of ventilation and anesthesia gases that enter and exit the oxygenator 330, which is controlled by the ventilation gas delivery system 332 and vaporizer 350. As described herein (e.g., refer to FIG. 3, the ventilation gas delivery system 332 can also monitor exhaust gas. By use of capnography and/or various sensors, exhaust gas monitoring can provide real-time measurements of expiratory gases from the oxygenator 330. In-line blood gas monitoring, flow, pressure, and temperature sensors 208A-N (e.g., probes) are depicted in both venous return and arterial supply sections of the extracorporeal circuit of the HLM system 100. These sensors 208A-N can provide real-time measurements of monitored parameters during the procedure.

The venous return blood from the patient 10 can follow the flow 500 through one or more components of the HLM system 100. As the blood moves through the HLM system 100 circuit, one or more sensors 208A-N can measure (or be used to calculate) real-time conditions of the blood. For example, some of those conditions can include pH, $pCO_2$, $pO_2$, $K+$, temperature, $SO_2$, hematocrit, hemoglobin, base excess, bicarbonate, oxygen consumption and oxygen delivery. Any of these values that are sensed by the sensors 208A-N can be transmitted to the computer system 202, as described herein.

The blood can then flow through the occluder 328 and into the venous reservoir 342. The vacuum source or regulator 344 can be configured to regulate the blood in the venous reservoir 342. While the blood is in the venous reservoir 342, blood levels in the reservoir 342 and/or volume levels can be sensed/monitored by the sensor 208N. A level sensing system can be used to determine how full of blood the reservoir 342 is. A certain amount of volume may be needed to open the hemoconcentrator circuit 334 and adjust different levels of the blood. The vacuum source/regulator 344 can thus be used to adjust volume levels in the venous reservoir 342. For example, the sensed volume can be transmitted to the computer system 202. Based on the sensed volume level, the practitioner can select an adjustment that causes the computer system 202 to semi-autonomously adjust the vacuum source 344.

From the venous reservoir 342, the blood can flow through the arterial pump 326. One or more manual and/or semi-autonomous adjustments can be performed at the arterial pump 326. For example, a semi-autonomous adjustment performed by the computer system 202 can include adjusting a blood flow through the arterial pump 326.

The blood then flows into the oxygenator 330. The ventilation gas delivery system 332 can be configured to monitor exhaust gas and adjust levels of source gases that are removed or added to the blood in the oxygenator 330 (e.g., refer to FIG. 3). The computer system 202 can perform a semi-autonomous adjustment of adjusting a sweep rate. This adjustment can be performed at the ventilation gas delivery system 332. Source gases, such as ambient air, oxygen, and/or carbon dioxide can be brought into the system 332 via the flow 502. The source gases can pass through the vaporizer 350, where anesthesia gases can be administered by a user (e.g., the practitioner). The gas vaporizer 350 can be placed in the gas delivery line to deliver the inhalation anesthetic (e.g., isoflurane, sevoflurane, etc.) to an input gas mixture of the oxygenator 330. For example, the gas vaporizer 350 can create a vapor from a liquid anesthetic and deliver a gaseous anesthetic in vapor form to the input gas mixture of the oxygenator 330. Anesthetic gases can therefore be administered to the input gas mixture of the oxygenator 330 and adjusted by the user by means of the gas vaporizer 350. Inhalation anesthetic can be used during cardiopulmonary bypass to maintain general anesthesia.

Once through the vaporizer 350, the gases can pass through a gas sensor 352 before entering the oxygenator 330 via a ventilation gas inlet. The gas sensor 352 can determine levels and/or concentrations of the gases and report such values to the computer system 202. Monitoring the gases (include the anesthesia gases) can be advantageous to control patient safety. The gas sensor 352 can sense presence of anesthetic agent or lack of agent, and a measured input percentage, in the gas. Such a sensor 356 can therefore detect a percentage in the exhaust gas that can be used by the computer system 202 to calculate a difference between inhalation anesthetic being delivered to the oxygenator 330 and an actual dosage amount to the patient. Inlet and outlet percentages of anesthetic gases can also be displayed and trended for the practitioner at the user device displays. Exhaust gas can be expelled from the oxygenator 330, pass through a gas sensor 356, and be delivered to a gas collection system. The gas sensor 356 can determine levels and/or concentrations of the exhaust gas and report such values to the computer system 202.

Once the blood passes through the oxygenator 330, the blood can be passed through the hemoconcentrator circuit 334. One or more adjustments can be semi-autonomously performed on components of the hemoconcentrator circuit 334 by the computer system 202. The blood can be routed back through the venous reservoir 342, the arterial pump 326, and the oxygenator 330.

The blood can then flow back to the patient 10 as an arterial blood supply. As the blood is transported back to the patient 10, one or more sensors 208A-N can measure real-time conditions of the blood flow. For example, the sensors 208A-N can measure blood gas and H/Sat values, flow rate, temperature, and pressure. The sensed conditions can be transmitted to the computer system 202.

Figure 5B:
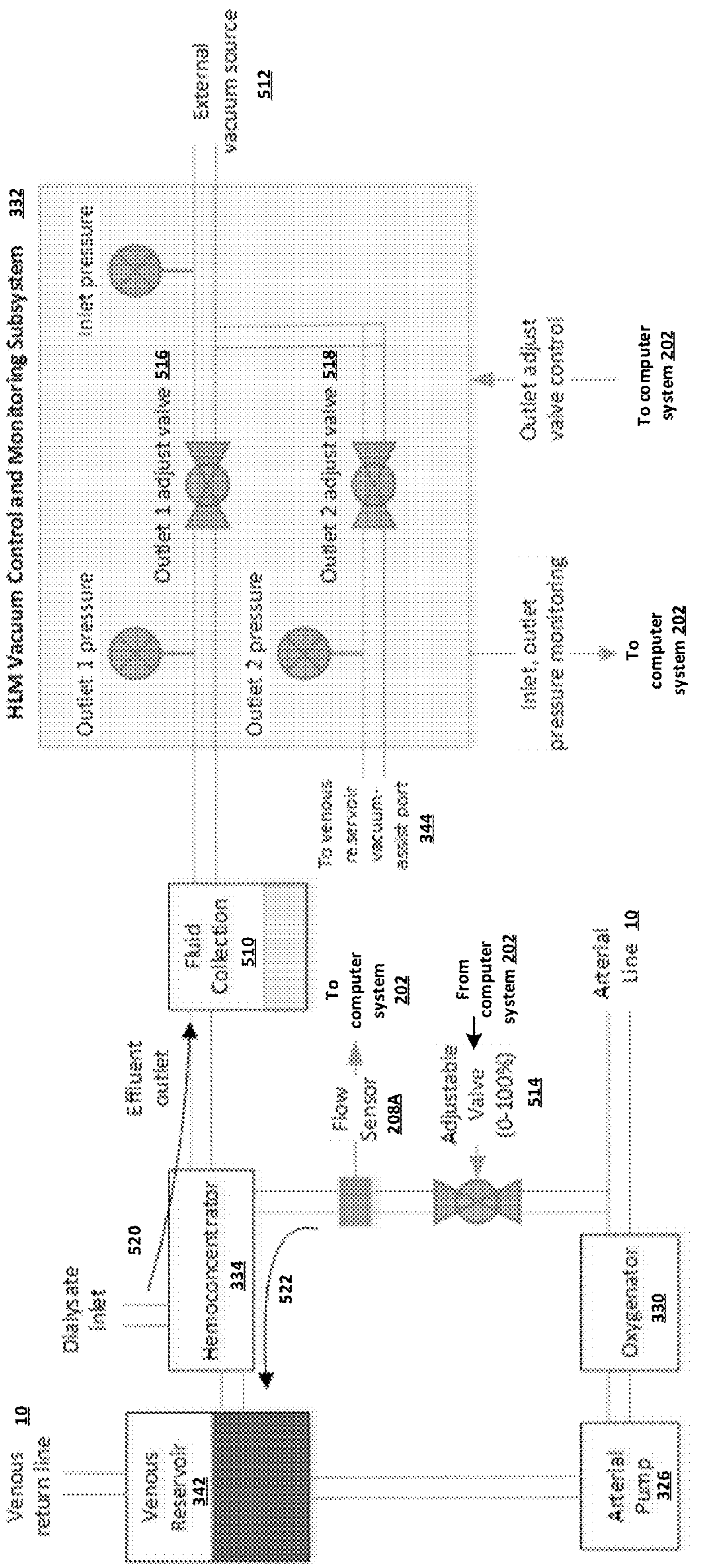
FIG. 5B is a block diagram of an example HLM system for monitoring and controlling a hemoconcentrator.

FIG. 5B is a block diagram of the example heart/lung machine system 332 that is configured for monitoring and controlling the hemoconcentrator 334. Using an adjustable valve 514, HLM vacuum control and monitoring subsystem 332, as described in reference to FIG. 3 and FIG. 5A, a practitioner can control the external hemoconcentrator 334 for purposes of adjusting a level of hemoglobin in arterial blood. Moreover, this control can be advantageous to improve control and monitoring of $DO_2$, as described further below (e.g., refer to FIGS. 13-14).

As depicted, the subsystem 332 can provide for at least two HLM-adjustable vacuum sources, such as the venous reservoir vacuum 344 and an external vacuum source 512. At least one vacuum source (e.g., the vacuum 512) can be used to control flow between the hemoconcentrator 334 via an effluent outlet and a fluid collection 510 (e.g., via a flow 520). At least another vacuum (e.g., the venous reservoir vacuum 344) can be connected to the venous reservoir 342 to provide for adjustable vacuum-assisted venous blood return via the venous return line 10.

Additional functionality of the subsystem 332 includes flow sensing (e.g., via the flow sensor 208A) and control of the adjustable valve 514. The valve 514 can be adjusted to provide for 0-100% flow to the hemoconcentrator 334 blood inlet (e.g., via a flow 522). Resultant hemoglobin concentration can be measured by a system blood gas parameter monitor, such as the computer system 202. Additional adjustable valves, such as adjustable vacuum valves 516 and 518, can be controlled by the subsystem 332 to provide for practitioner-desired vacuum flow. In some embodiments, one or more additional adjustable valves can be added to the hemoconcentrator 334, the venous reservoir 342, and/or the effluent outlet at the fluid collection 510 to provide for more precise means of fluid control within the disclosed perfusion circuit.

Moreover, as depicted, the subsystem 332 can receive instructions from the computer system 202 to automatically adjust one or more components, such as the valves 516 and/or 518. For example, the practitioner can input into the computer system 202 outlet adjustments and valve controls that can be semi-autonomously performed by the computer system 202 and/or the subsystem 332. The practitioner can define these adjustments before real-time use of the disclosed perfusion circuit. Then, during real-time use of the circuit, the practitioner can actuate the semi-autonomous adjustment at the computer system 202, thereby causing one or more valves (e.g., the valves 514, 516, and/or 518) to adjust to provide for a different flow or pressure through such valves. As another example, the computer system 202 can receive inlet and/or outlet pressure monitoring values (e.g., from the sensors 208A-N). These values can be displayed at the computer system 202 and/or a display device. The practitioner can then view real-time updates of pressure and flow throughout the disclosed perfusion circuit. Based on the displayed pressure and flow, the practitioner can make manual adjustments and/or actuate semi-autonomous adjustments that the practitioner had defined before the procedure.

Figure 5C:
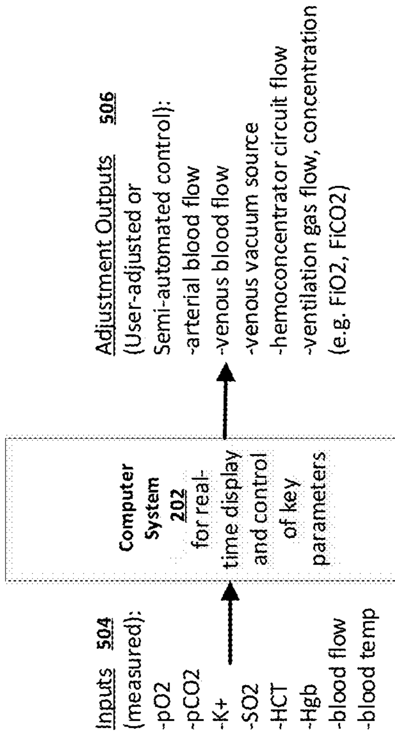
FIG. 5C is a block diagram of inputs and outputs of the example monitoring and control system described herein.

FIG. 5C is a block diagram of inputs 504 and outputs 506 of the example monitoring and control system described herein. As depicted, the computer system 202 can receive various inputs 504. The inputs 504 can be values that are measured by the sensors 208A-N in real-time, during a procedure. For example, some of the measured inputs 504 can include pO2, pCO2, K+, SO2, HCT, Hgb, blood flow, and blood temperature. The computer system 202 can use the inputs 504 to generate real-time display and control of one or more parameters. Thus, the computer system 202 can provide adjustment outputs 506 for adjusting components of the HLM system, and/or for display at a user device. The outputs 506 can be user-adjusted and/or semi-automated controls. Some of the adjustment outputs 506 can relate to an arterial blood flow, a venous blood flow, a venous vacuum source, a hemoconcentrator circuit flow, a ventilation gas flow, a ventilation gas concentration, and exhaust gas monitoring.

The venous and arterial sensors 208A-N, as depicted in FIG. 5A, can provide real-time measurements (e.g., the inputs 504) that are displayed and processed by the computer system 202. Calculated values may also be derived from these measurements and further processed by the computer system 202 and/or by a CDI (e.g. cardiac index, oxygen extraction ratio, VO2, DO2, and VCO2). The computer system 202 can also include user interface controls or semi-automated control features that are used to adjust the arterial pump 326, venous occluder 328, hemoconcentrator circuit 334, regulated venous vacuum source 344, and ventilation gas delivery system 332, as described throughout this disclosure. Therefore, the computer system 202 can be used by the practitioner to meet dynamic patient needs, ensure patient safety, and improve procedure outcomes.

FIG. 6 is an example user interface 600 of the example monitoring and control system described herein. The user interface 600 can include arterial flow control and parameters 618 and venous flow control and parameters 620, ventilation gas delivery 616, and monitored blood gas parameters 602. The blood gas parameters 602 can be user-selectable by the practitioner during system configuration (e.g., refer to FIGS. 2-4). This user interface 600 can be deployed in any display or other output device, such as a touchscreen, monitor, or other screen. In addition, the user interface 600 can be adjusted in appearance based on a display screen's ratio. In some examples, the user interface 600 can be deployed on a mobile devices. For example, the mobile device can be remote-mountable. The practitioner can position the device at a desired location, such as near associated arterial/venous circuit components (e.g., venous reservoir, oxygenator, hemoconcentrator, vacuum source(s)) as depicted and described throughout this disclosure. The fully integrated user interface 600 can improve usability and patient safety by reducing a need for the practitioner to rely upon interaction with multiple different monitoring and control devices.

While the user interface 600 is intended for primary control of the arterial-venous perfusion circuit (e.g., one or more components of the HLM system 100), one or more additional displays can be utilized to supplement display and control capability. In some implementations, the content of any of the additional displays can be kept in-sync with the computer system 202 for the purpose of redundancy or practitioner preference. The other displays can also provide additional space for supplemental features and/or monitoring and control of less critical parameters. User interfaces associated with each of the displays can provide for a high degree of user-configurability (e.g., selection and placement of displays and controls, selection of primary and secondary display features, selection of parameters and associated numeric/trending format, parameter alert/alarm limits, etc.).

Referring to FIG. 6, the monitored blood gas parameters 602 can include parameter trending information. The real-time blood gas and physiologic parameter monitoring 602 functionality can provide for user-selectable parameters to be displayed as necessary or desired for a range of user-specific blood gas parameter management practices. As a result, the display 602 can be used to help ensure proper gas delivery and efficiency of patient perfusion. User-selectable display formats can be numeric, graphical trending, or combinations of both. For user-selected parameters, capability can be provided for the practitioner to select or set up limits (e.g., target, range, alert/alarm thresholds) that can be utilized for manual monitoring and control, as well as optional semi-automated or advanced servo-parameter control.

The parameter trending information in the display 602 can include a graph 601. The graph 601 can be associated with one or more parameters that are being monitored during the procedure. The practitioner can define what parameters are monitored and graphed. In the example user interface 600, the practitioner selected partial pressure of carbon dioxide (PaCO2) as the trending parameter. The practitioner also set parameter ranges 603A-N for PaCO2 monitoring. For example, the practitioner set ranges 603A-C for upper alarms, alerts, and control limits. The practitioner also set ranges 603D-N for lower alarms, alerts, and control limits. The ranges 603A-N are the practitioner's desired ranges to keep the target parameter PaCO2 within. Trending line 608 indicates past sensed conditions, present sensed conditions, and projected conditions of the parameter PaCO2. Selectable options 604A-N can also be placed along a top portion of the graph 601. The selectable options 604A-N can be one-touch buttons on a touchscreen user interface. The practitioner can select any of these options to actuate an adjustment that corresponds to the selected option. For example, if the practitioner selects the button "Increase PaCO2 slope," the computer system 202 described herein can semi-autonomously increase the PaCO2 slope based on an amount of increase in PaCO2 that the practitioner defined before the procedure. The trend 608 can be updated in real-time to reflect this semi-autonomous adjustment.

As another example, the practitioner can see that the trend 608 is increasing at a time A. At time A, the practitioner can select the option "Decrease PaCO2 slope" to avoid the trend 608 from hitting the upper control limit 603C. The computer system 202 can semi-autonomously reduce the PaCO2 slope based on an amount of decrease in PaCO2 that the practitioner defined before the procedure. This adjustment can be reflected in the trend 608 in real-time. This configuration is advantageous because the practitioner does not have to spend time during the procedure manually determining how much to increase or decrease the PaCO2 slope and then manually increasing or decreasing the PaCO2. The practitioner can more effectively monitor and control all the parameters during the procedure.

The practitioner can establish a desired control range and specify one or more pre-defined sequences of control adjustments and associated timing that can be automatically executed by the computer system 202 upon practitioner initiation. Practitioner initiation can be in response to a desired trending effect on common patient blood gas parameter target correction scenarios. Such functionality can provide a timely and consistent response while the practitioner retains full control of initiation. The primary safety and usability benefit of this semi-automated functionality can provide the practitioner with a means of early detection of any undesired parameters or grouped parameters trending. Therefore, the practitioner can take timely and consistent corrective responses.

In response to correcting the trending of any practitioner-selected blood gas parameter, the practitioner can establish a pre-defined sequence of control adjustments for any combination of the following: arterial blood flow rate, venous blood flow return rate, blood flow through the hemoconcentrator, sweep gas flow rate, FiO2, and/or FiCO2. As described herein, for any control adjustment parameter, the practitioner can specify an amount of increment/decrement and upper/lower adjustment limits. In addition, the practitioner can specify a time duration of each adjustment, a number of allowed adjustments, and a total duration of a sequence of adjustments.

Any adjustments made to control the parameters, whether semi-automated or manual, can be reflected in the graph 601. The graph 601 can reflect real-time changes to the monitored parameters trends. This is beneficial to assist the practitioner in accurately monitoring and controlling the parameters for a duration of the procedure.

As demonstrated, more than one gas parameter or control can be depicted in the graph 601. For example, trend line 610 can indicate trending of a sweep control. Trend line 612 can indicate trending of a fraction of inspired oxygen (FiCO2) control. Sweep and FiCO2 are additional controls that can be semi-autonomously adjusted based on trending of PaCO2. These controls can also be configured by the practitioner before the procedure. For example, the practitioner can determine which additional parameters and controls to display in the graph 601 with the PaCO2 parameter. As another example, the practitioner can determine what semi-autonomous adjustment(s) should be made to the sweep and/or FiCO2 when the PaCO2 slope is increased and/or decreased. Thus, when the PaCO2 slope is decreased, the sweep can be automatically increased in response. Therefore, the practitioner can decide that when adjustments are made to the PaCO2 parameter, one or more adjustments can also be made (e.g., simultaneously or at a different time) to one or more other related parameters.

The trends of PaCO2 in 608 can be dynamically updated in real time due to physiological changes in the patient or circuit. Changes that occur to effect the PaCO2 parameter will also cause the sweep and/or FiCO2 to change dependent upon the preconfigured semi-autonomous actions (e.g., an increase or decrease in slope of the sweep and/or FiCO2). Changes to the sweep and/or FiCO2 can be reflected in real-time in the trends 610 and 612 in the graph 601.

For example, as shown in the graph 601, at time A, PaCO2 parameter 608 was trending in an upward slope. The practitioner adjusted the sweep 610 upward to decrease the upward slope of the PaCO2 parameter 608. Additional example as shown in the graph 601, at time B, the PaCO2 parameter was trending in a downward slope. Because of the adjustment of the sweep 610 in a downward slope, and/or the FiCO2 in an upward slope 612, the trending line 608 is slowly increasing. This demonstrates physiological changes that occur to the PaCO2 parameter can also affect trending of both the sweep and the FiCO2 parameters. Effects to the trending of sweep and FiCO2 can be reflected in real-time in the graph 601.

Still referring to FIG. 6, the selectable options 604A-N can include "Enable Manual Control" and "Setup" options. The "Enable Manual Control" option allows the practitioner to take over full control of parameter adjustments. In other words, the practitioner does not select an option that enables the computer system 202 to semi-autonomously perform a pre-defined adjustment. The practitioner can manually control the parameters by pressing one or more buttons depicted in the user interface 600. The practitioner can also manually control the parameters by using any one of the physical buttons 620A-N (e.g., knobs) beneath the user interface 600. The physical buttons 620A-N can be part of the user device. The buttons 620A-N can also be connected wirelessly and/or wired to the user interface 600 and/or one or more components of the user device, the computer system 202, and/or the HLM. In yet other examples, the buttons 620A-N can be located on one or more devices or the HLM that the practitioner is manually controlling. Exemplary buttons 620A-N can permit the practitioner to adjust arterial flow, venous occlusion, as flow, FiO2, and/or FiCO2. One or more other parameters and/or conditions can be monitored and adjustable by the buttons 620A-N. In some implementations, fewer or more physical buttons 620A-N can be provided to the practitioner to have increased manual control during the procedure. When the practitioner makes manual adjustments, the graph 601 can be updated in real-time to reflect such changes.

Figure 7:
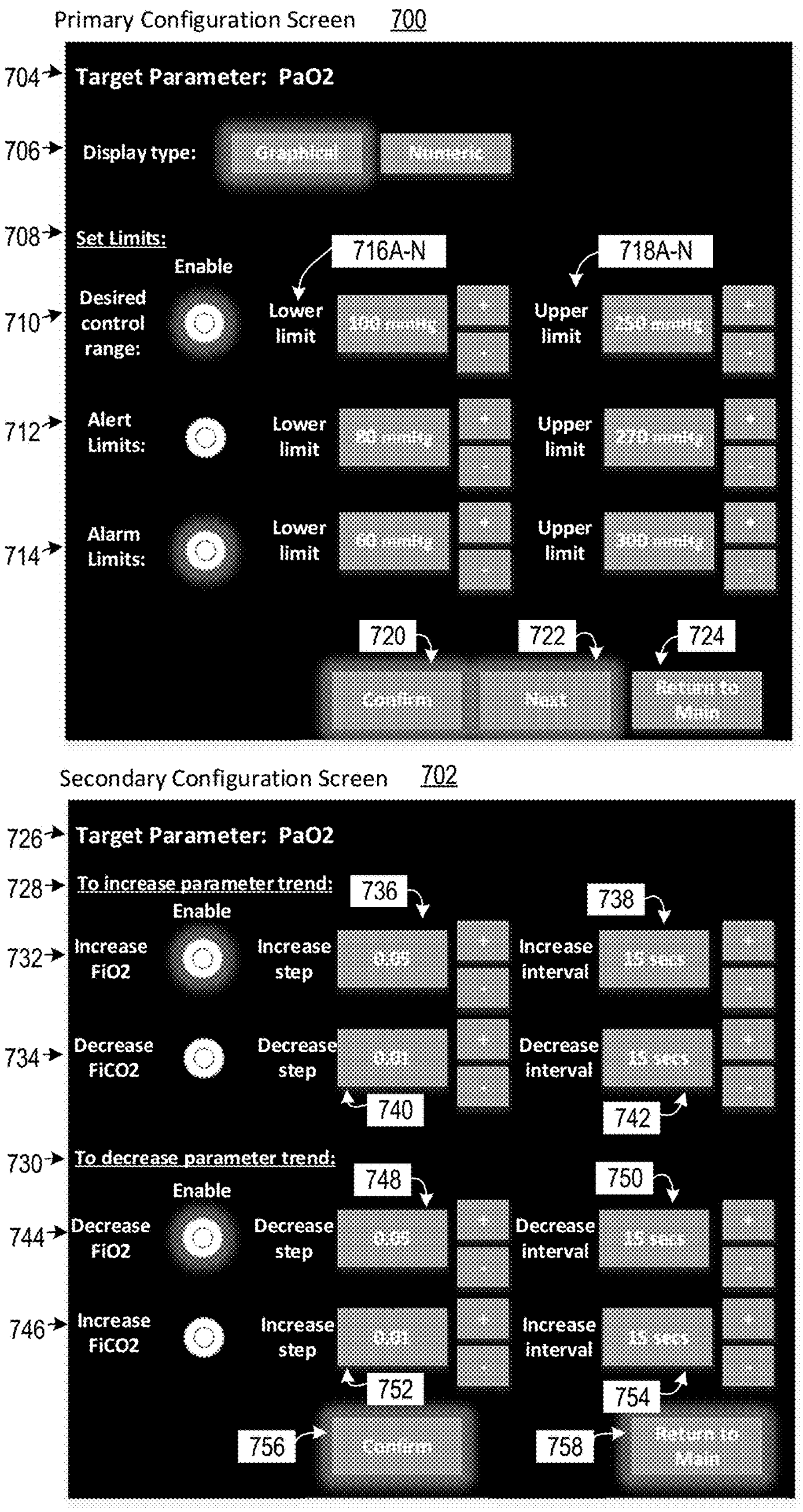
FIG. 7 illustrates example user interface for configuring the monitoring and control system described herein.

The "Setup" selectable option can provide the practitioner with a second user interface (e.g., refer to FIG. 7). The second user interface can include options for the practitioner to customize or configure the user interface 600, set parameters, set parameter trends and ranges, and establish parameter adjustments. The practitioner can access this second user interface before the procedure begins.

The user interface 600 can be adjusted to the practitioner's preferences, thereby allowing a high degree of display layout customization. This customization can include left, right, up and down orientation of the arterial flow control and parameters 618, the venous flow control and parameters 620, the gas delivery controls 616, and the parameters 602. The practitioner can decide such layout customization using defined layout frameworks provided via the computer system 202. Using the defined layout frameworks can ensure that the user interface 600 can be appropriately used by the practitioner and/or not overcrowded with too much information. For example, the defined layout frameworks can prevent the practitioner from placing controls, displays, or graphs too close to each other. The defined layout frameworks can also be adapted to fit different screen ratios. For example, a mobile device screen, such as that of a smartphone or tablet, may permit the practitioner to include fewer controls or displays on the user interface 600 than a computer screen or monitor.

The practitioner can also access this second user interface during the procedure by selecting (e.g., pressing, touching, clicking on, etc.) the "Setup" option (e.g., button) of the options 604A-N. If the practitioner makes any user-defined adjustments during the procedure, those adjustments can be automatically reflected in the user interface 600.

Still referring to FIG. 6, the monitored blood gas parameters 602 can also include selectable options 614A-N. These options 614A-N can be buttons that the practitioner clicks, selects, and/or touches. Each of the options 614A-N can provide the practitioner with a graph associated with a different monitored parameter. In this example, the options 614A-N allow the practitioner to flip between graphs for "PaO2 trending," "PaCO2 trending," "DO2 trending," "O2ER trending," and "Cardiac Index Trending." When the practitioner sets parameters and settings for the user interface 600, the practitioner can indicate which parameters should be monitored and displayed, as well as an order to display such parameters. Thus, the options 614A-N can dynamically adjust based on the user-defined settings.

In other implementations, the user interface 600 can present multiple trending parameters and their associated graphs on a same screen. For example, when setting up the user interface 600 before the procedure, the practitioner can indicate that they want PaO2, PaCO2, DO2, O2ER, VCO2, ratios, etc., and/or Cardiac Index trending graphs all on the same user interface 600. Therefore, the practitioner would not have to move between graphs by selecting the options 614A-N. By displaying more than one trending parameter on the user interface 600 at a time, the practitioner can more easily and effectively monitor and control the parameters. This can result in ensuring patient safety and improving patient outcomes.

As mentioned, the practitioner can also monitor gas delivery 616 using the user interface 600. The ventilation gas delivery 616 functionality includes configuration of blending gases (e.g., air, 95/5, CO2), control of gas flow rate and concentration (e.g., FiO2, FiCO2), monitoring of exhaust gas, and safety features. The safety features can include user-selectable FiO2 and FiCO2 limits. In addition, for consideration of oxygenator transfer efficiency, a ratio of gas to blood flow can be displayed. As an optional alternative, a feature could be added to allow the gas and blood flow rates to be adjusted "in-sync" or in real-time to maintain a user-selectable target ratio. This can be beneficial to achieve optimal gas transfer through an oxygenator as gas delivery parameters are altered during a medical procedure (e.g., in response to patient temperature and/or associated metabolic needs).

Thus, the gas/blood flow ratio can allow the practitioner to adjust gas or blood flow in proportion to each other. After all, oxygenators can perform more efficiently when gas and blood flow are proportionately adjusted (e.g., in a one to one ratio). Using the gas delivery 616, the practitioner can control operation of vacuums in the HLM (e.g., the vacuum source 336 and/or the regulated venous vacuum source 344 in FIG. 3). The practitioner can select options/buttons such as "Info," "Settings," and/or "Status/fault info" in order to view real-time information about the gas/blood flow and make any necessary adjustments. For example, the user interface 600 can be in communication with an input device, such as a keyboard. The practitioner can input values at the keyboard to adjust any of the conditions for the gas delivery 616. These values can be reflected in the updated gas delivery 616.

The gas delivery 616 can also include expired carbon dioxide measurement (expiredCO2) in oxygenator exhaust gas analysis and can be converted to an independent volumetric number (VCO2) or a patient body surface area indexed value (VCO2i). Measurement of expiredCO2 and evaluation of the VCO2 can add to efficiency of perfusion, since carbon dioxide production is a by-product of cellular metabolism from oxygen delivery to end tissues. Measurement of the carbon dioxide production (VCO2, expiredCO2, VCO2/DO2 ratio) values can aid in control of adequate oxygen delivery to the patient. User selectable carbon dioxide variables (e.g., ranges) can trigger an adjusted increase in oxygen delivery to end tissues, or a decrease in metabolic demands.

Likewise, the practitioner can monitor arterial blood flow via the arterial flow control and parameters 618 and venous blood flow via the venous flow control and parameters 620. With regards to the arterial control and parameters 618, one or more selectable options can be presented on the user interface 600 to provide the practitioner with manual and semi-autonomous adjustment capabilities. For example, the practitioner can view gases 622. The practitioner can monitor air bubble detection (ABD) via ABD and clamp controls 624. The controls 624 can include "Detect status," "Enable/Disable/Reset," and "Open/Close." The practitioner can also control and monitor flow via Arterial, Capiox, and Delta Q controls 626. The controls 626 can include "Stop" and "Manual" functionality. The practitioner can also control and monitor status, fault information, and the hemoconcentrator via status/fault info and hemoconcentrator controls 628. The controls 628 can include selectable options for "Settings/Reset" and "Hemoconcentrator On/Off."

The arterial control and parameters 618 can be adjusted depending upon usage of a centrifugal or roller pump. For arterial pumping with a centrifugal pump, the user interface 600 includes the "Open/Close" selectable option for the clamp in the controls 624. In addition to configuring a triggered response to a safety event (e.g., activate clamp if an air bubble is detected in an arterial line), a control can be provided to allow the practitioner to manually open or close the clamp, along with an associated graphical indicator of a clamp status (e.g., hemostat icon in open or closed position). Therefore, the clamp can be semi-autonomously opened or closed by the computer system 202 and can also be manually controlled by the practitioner.

The "Detect Status" and "Enable/Disable/Reset" options for the ABD controls 624 can provide for safety monitoring features. For air bubble detection, controls can be provided to manually and/or semi-autonomously enable, disable, and reset bubble detection, as well as selecting a small, medium, or large bubble size setting for detection purposes. Bubble detection status can be indicated by a visual (e.g., color icon) and/or textual (e.g., a message in the "status/fault info" window at the bottom of the arterial blood flow 618) means.

With regards to the venous flow control and parameters 620, one or more selectable options can be presented. For example, the practitioner can view gases 630 as they are monitored in real-time during the procedure. Occluder controls 632 can include selectable options to "Calibrate," "Open," and "Close" components associated with the venous blood flow. Venous level controls 634 can include selectable options to "Detect status," "Enable/Disable," and "Venous vacuum On/Off." The "Detect Status" and "Enable/Disable/Reset" options for the venous level can provide for safety monitoring features. The practitioner can also view real-time measurements of venous flow 636. For venous reservoir level detection, controls 634 can be provided to enable or disable detection, as well as select detect modes (e.g., alert only, alert and alarm level detection thresholds, etc.). Level detection status can also be indicated by visual and/or textual means, as described above in reference to the ABD. For venous reservoir volume, the measured value can be indicated by visual and/or textual means, which can be utilized by the practitioner in determining whether to increase arterial flow and supplemental hemoconcentrator flow.

The occluder controls 632 can allow the practitioner to control blood flow to the venous reservoir. If a venous flow probe (e.g., sensor) is utilized, then a calculated "delta Q" value (e.g., arterial-venous blood flow) can be displayed along with a trending indicator to inform the practitioner of a dynamic balance of flow within the arterial-venous perfusion circuit, including an indication of whether a blood level in the venous reservoir is increasing or decreasing. The venous level and vacuum controls 634 can also allow the practitioner to enable or disable a regulated vacuum source. The vacuum source can provide supplemental venous return blood flow to the venous reservoir. In addition, monitoring of the vacuum pressure can be indicated in the venous flow control and parameters 620.

Referring back to the controls 628, a summary of any component-triggered safety event responses can be provided for the arterial pump and/or the venous occluder via the "Status/fault info" window of the controls 628. The hemoconcentrator control and status display can allow the practitioner to enable or disable a fully-open/close clamping mechanism (e.g., proximal and/or distal to the hemoconcentrator). For example, the fully-open/close clamping mechanism or valve can provide for fully adjustable flow through the hemoconcentrator, from 0-100% flow. In some implementations, the clamping mechanism can be adjustable valves having 0-100% flow capability. The adjustable valves can be placed proximal and/or distal to the hemoconcentrator, as necessary to adequately control flow of blood through the hemoconcentrator. Additionally, as depicted and described herein, a flow sensor can be used to measure blood flow through the hemoconcentrator. The measured blood flow can be outputted to the user interface 600. The practitioner can benefit from viewing the measured blood flow because it can assist pediatric and other clinical applications that require precise management of fluid in a medical procedure.

These controls and display 628 can also allow the practitioner to adjust the regulated vacuum source to control effluent of arterial blood through a hemoconcentrator and back to the venous reservoir. Any of these adjustments can be performed manually by the practitioner or semi-autonomously by the computer system 202 when the user selects the controls on the user interface 600. Control of the hemoconcentrator can provide the user with the ability to adjust a level of hemoglobin in arterial blood. Although not depicted, the user interface 600 can provide additional selectable options that assist the user in adjusting a pressure of a vacuum source that is connected to the hemoconcentrator circuit to pull fluid out of the blood. For example, the control(s) can be linked to a second vacuum source that can be used to supplement return of blood flow in a venous line.

One or more other selectable options can be provided in the user interface 600. Moreover, when setting up the user interface 600, the practitioner can indicate which selectable options, HLM components, parameters, and/or real-time conditions should be displayed.

FIG. 7 illustrates example user interfaces for configuring the monitoring and control system described herein. Depicted is a primary configuration screen 700 and a secondary configuration screen 702. The screens 700 and 702 pertain to configuring the monitoring and control system described herein for a PaO2 target parameter. Each target parameter can have a parameter-specific set of configuration options for limits and trending responses. In some implementations, another target parameter can have different configuration options than the PaO2 target parameter, as depicted in FIG. 7.

Referring to the primary configuration screen 700, a target parameter 704 can be identified. In the example of FIG. 7, PaO2 is the target parameter 704. A practitioner has an option to select a display type 706, which can be "Graphical" or "Numeric." In some implementations, the practitioner can select both graphical and numeric display types to be displayed at the monitoring and control system. Each of the options "Graphical" and "Numeric" can be selectable buttons presented on the user interface screen 700. The practitioner can then define limits for the target parameter 704 in a set limits portion 708 of the screen 700. The practitioner can select what options to display for the target parameter 704 at the monitoring and control system. In this example, the practitioner can enable display of one or more of a desired control range 710, alert limits 712, and alarm limits 714. Alert limits 712 can be conditions in which the target parameter 704 is trending towards an alarm state.

Alarm limits 714 can be a higher priority, more urgent state that informs the practitioner that the target parameter 704 is in a range that can be detrimental to patient care and safety. In other examples having different target parameters, one or more other or additional options can be displayed on the screen 700 for practitioner configuration. Here, the practitioner selected to enable display of the desired control range 710 and the alarm limits 714. The practitioner can set parameter ratios (e.g. Gas/Blood flow, DO2/VCO2, etc.) to allow trending and data collection of custom parameter ratios of interest to a specific perfusionist, surgeon-protocol, and/or institution.

The practitioner can also set values or ranges for each of the options 710, 712, and 714. Lower limits 716A-N and upper limits 718A-N can be set for each option 710, 712, and 714, respectively. Here, the practitioner set the lower limit 716A for the desired control range 710 at 100 mmHg and the upper limit 718A at 250 mmHg. For the alert limits 712, even though the practitioner did not enable display of this option, the practitioner set the lower limit 716B at 80 mmHg and the upper limit 718B at 270 mmHg. For the alarm limits 714, the practitioner set the lower limit 716N at 60 mmHg and the upper limit 718N at 300 mmHg.

As depicted, the practitioner can set the lower limits 716A-N and the upper limits 718A-N using selectable up and down buttons (e.g., + and − buttons) that are displayed on the screen 700. In other implementations, the practitioner can set the lower limits 716A-N and the upper limits 718A-N using one or more input devices, such as a keyboard, physical buttons, a microphone, and/or a touchscreen display.

The screen 700 further includes a confirm button 720, a next button 722, and a return to main button 724. Selecting the confirm button 720 can save the configuration selections made by the practitioner on the screen 700. The configuration selections can be saved to a data store (e.g., the parameter ranges database 322 in FIG. 3) such that these configuration selections can be used for subsequent similar procedures in the future. Selecting the next button 722 can bring the practitioner to a new configuration screen, such as the secondary configuration screen 702 depicted in FIG. 7. In other implementations, selecting the next button 722 can bring the practitioner to another primary configuration screen 700 for a different target parameter. Therefore, the practitioner can configure each target parameter in one seamless process rather than having to return to a main screen of the monitoring and control system and then selecting a different target parameter to configure. Selecting the return to main button 724 can bring the practitioner back to the main screen of the monitoring and control system (e.g., refer to the user interface 600 in FIG. 6). The main screen can seamlessly be updated to reflect configuration selections made by the practitioner at the primary configuration screen 700.

As depicted in the primary configuration screen 700, one or more selectable options can have a glow or highlight effect. This type of visualization can assist the practitioner in reviewing or seeing what selections they made. For example, the “Graphical” button has a glow effect because the practitioner selected that option for the display type 706. Radio buttons for the desired control range 710 and alarm limits 714 have glow effects because the practitioner chose to enable those limits. Moreover, the confirm button 720 and the next button 722 can have glow effects to prompt the user to select those options.

Still referring to FIG. 7, the secondary configuration screen 702 can include target parameter 726, a increase parameter trend portion 728 of the screen 702, and a decrease parameter trend portion 730 of the screen 702. In this example, the secondary configuration screen 702 is prompted to the practitioner when the practitioner selects the next button 722 in the primary configuration screen 700. Therefore, the secondary screen 702 displays the same target parameter 704 of the primary screen 700: PaO2. In other implementations, the secondary configuration screen 702 can present a different target parameter 726 than the target parameter 704 of the primary configuration screen 700.

The secondary configuration screen 702 can automatically populate with additional configurable parameters or properties based on the target parameter 726. Here, because the example target parameter 726 is PaO2, the increase parameter trend portion 728 presents selectable options to increase FiO2 732 and decrease FiCO2 734. Like the screen 700, in the secondary screen 702, the practitioner can select one or more radio buttons for enabling to increase FiO2 732 and/or decrease FiCO2 734. The practitioner’s selection can have a glow effect, as depicted where the practitioner selected to enable the increase FiO2 732. The practitioner can then adjust or select to increase step 736 and/or increase interval 738 for the increase FiO2 732 trend. In this example, the practitioner chose to increase step 736 by 0.05 and to increase interval 738 by 15 seconds. In relation to the decrease FiCO2 734 control, the practitioner can adjust or select to decrease step 740 and/or decrease interval 742. The practitioner can adjust values for the increase step 736, increase interval 738, decrease step 740, and decrease interval 742 using one or more selectable up and down options or buttons that are displayed on the screen (e.g., + and − buttons). In other implementations, the practitioner can use one or more input devices, such as a keyboard, physical buttons, a microphone, and/or a touchscreen display.

In the example secondary configuration screen 702, the decrease parameter trend portion 730 presents selectable options to decrease FiO2 744 and increase FiCO2 746. As mentioned above, these trends can be different depending on the target parameter 736. Like the screen 700, in the secondary screen 702, the practitioner can select one or more radio buttons for enabling to decrease FiO2 744 and/or increase FiCO2 746. The practitioner’s selection can have a glow effect, as depicted where the practitioner selected to enable the decrease FiO2 744. The practitioner can then adjust or select to decrease step 748 and/or decrease interval 750 for the decrease FiO2 744 trend. In this example, the practitioner chose to decrease step 748 by 0.05 and to decrease interval 750 by 15 seconds. In relation to the increase FiCO2 746 trend, the practitioner can adjust or select to increase step 752 and/or increase interval 754. The practitioner can adjust values for the decrease step 748, decrease interval 750, increase step 752, and increase interval 754 using one or more selectable up and down options or buttons that are displayed on the screen (e.g., + and − buttons). In other implementations, the practitioner can use one or more input devices, such as a keyboard, physical buttons, a microphone, and/or a touchscreen display.

Still referring to the configuration screen 702, the practitioner can select a confirm button 756 and/or a return to main button 758. Selecting the confirm button 756 can save the configuration selections that the practitioner made in the screen 702. As mentioned above in reference to the screen 700, selections made in the screen 702 can be saved in a database and used in subsequent, similar medical procedures. Selecting the return to main button 758 can return the practitioner to the user interface 600 depicted in FIG. 6. Once the practitioner returns to the main screen (e.g., the user interface 600 in FIG. 6), the main screen can be automatically updated to reflect any of the configuration selections that the practitioner made in the primary configuration screen 700 and/or the secondary configuration screen 702. For example, selectable options to increase or decrease a slope of a trending parameter can be programmed to increase or decrease the slope based on the selections that the practitioner made in the screens 700 and 702.

Selections that the practitioner makes in the increase parameter trend portion 728 and the decrease parameter trend portion 730 of the screen 702 can be semi-autonomously performed during a medical procedure. As described throughout this disclosure, the practitioner sets measures or adjustments that can be performed manually or semi-autonomously during the procedure. These adjustments are set using the secondary configuration screen 702. During the procedure, as depicted in FIG. 6, the user interface 600 can display selectable options to invoke the measures or adjustments that the practitioner set using the secondary configuration screen 702. For example, in the increase parameter trend portion 728 of the screen 702 in FIG. 7, the practitioner selected to increase step 736 in order to increase FiO2 732. As depicted in FIG. 6, during the procedure, the practitioner can select one of the buttons 604A-N to "Increase PaCO2 slope." Once the practitioner selects that button, the monitoring and control system can semi-autonomously increase the PaCO2 slope by increasing step 736 by 0.05 for the increase FiO2 732 trend, as the practitioner set in the secondary configuration screen 702.

In some implementations, a practitioner who makes configurable selections in the configuration screens 700 and 702 may not be the same practitioner who performs the medical procedure. For example, one practitioner or user can make the configurable selections in advance of a medical procedure. A second practitioner can then perform the medical procedure at a later time using a monitor and control system that already reflects the configurable selections made by the first practitioner (e.g., the first practitioner's selections can be saved in a database and then retrieved from the database and applied to the monitor and control system just prior to the medical procedure). As a result, the second practitioner can immediately begin performing the procedure without having to adjust or make any of the selections for a trending parameter in the procedure.

Figure 8:
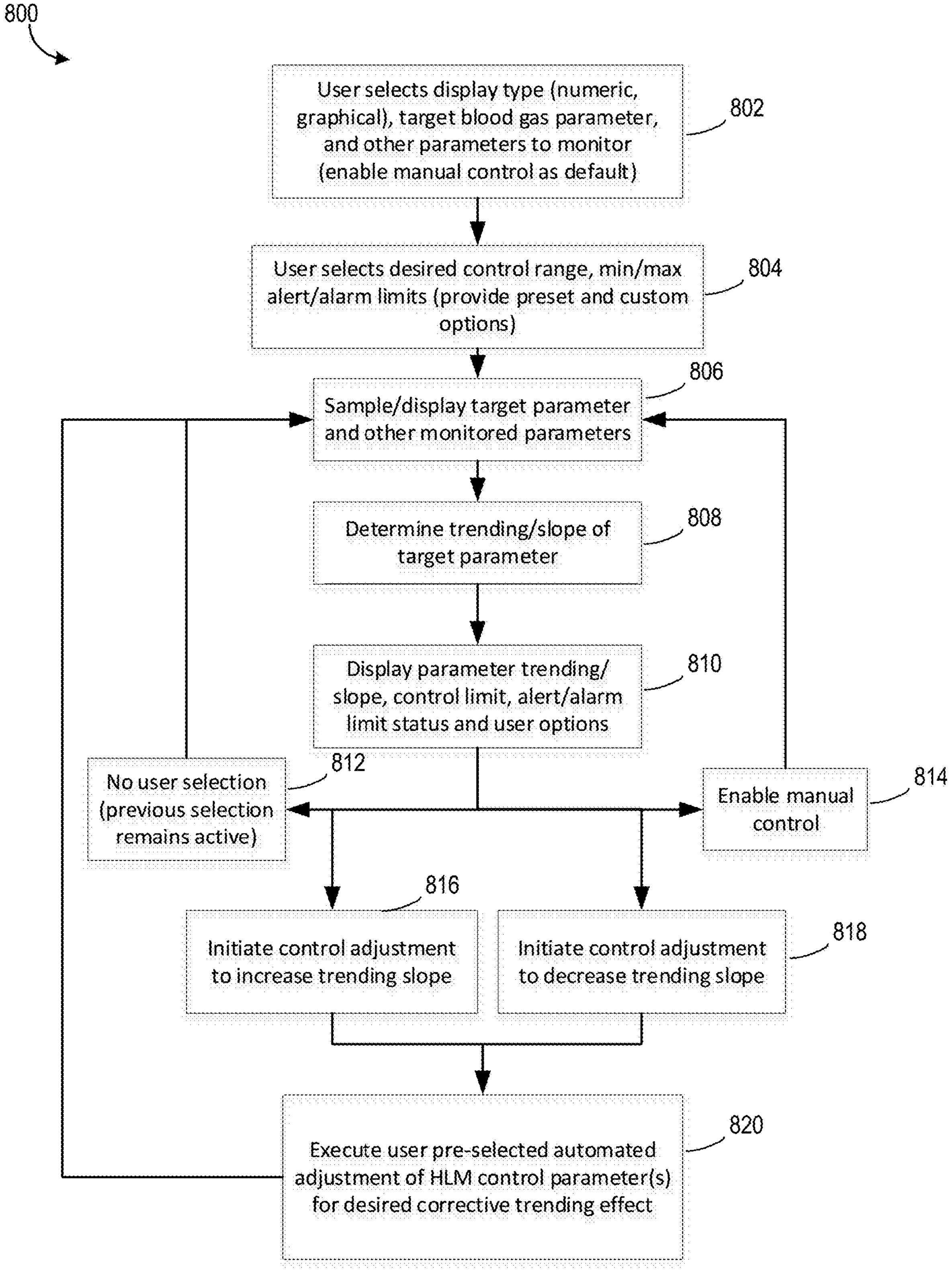
FIG. 8 is a flowchart of an example process for monitoring and controlling a blood gas parameter.

FIG. 8 is a flowchart of a process 800 for monitoring and controlling a blood gas parameter. The process 800 is an example algorithm that can be used to implement semi-autonomous adjustments of targeted parameters. This process 800 allows a practitioner (e.g., user) to select a numeric or graphical display type along with a target blood gas parameter and other associated parameters that can be simultaneously monitored (e.g., refer to FIG. 7 configuration screens). As described throughout this disclosure, the process 800 also provides for the practitioner to select and set desired control ranges, alert limits, and/or alarm limits.

Once the practitioner's selections are implemented by the monitoring and control system described herein, selected parameters can be sampled and displayed in real-time. Consequently, a trending slope can be determined and displayed at the monitoring and control system. As the practitioner monitors the parameter(s) trending during a procedure in real-time, the parameters can be presented with options to initiate the pre-defined control adjustment sequence (e.g., to semi-autonomously increase or decrease trending) that the practitioner made before the procedure. The parameters can also be presented with options to enable full, manual monitoring and control functionality by the practitioner. If the practitioner initiates a control adjustment sequence, the monitoring and control system described herein can execute that control adjustment sequence as it was pre-defined by practitioner's configuration (e.g., refer to FIG. 7). Once execution of the control adjustment begins, the practitioner can see correction of a direction of the parameter(s) trending displayed at the monitoring and control system.

Optionally, the practitioner can also configure a corrective trending response (e.g., the control adjustment sequence) to initiate automatically if a target parameter reaches one of the limits of a desired control range.

Not only does the process 800 assist the practitioner in performing adjustments on target parameters during a medical procedure, the process 800 also improves data collection techniques of the monitoring and control system described herein. For example, additional parameters, events, and continuous real-time trending patterns can be tracked, monitored, and recorded during a procedure (e.g., stored in a database). With such advanced data collection, collection timeframes can be extended and faster sampling rates can be generated. During the procedure, data can be collected that includes all parameter readings, control adjustments, events, user-selected patient size information, user-selected equipment configuration, procedure type, surgeon/surgical protocol, user-selected control range(s), alert/alarm limits, user-selected parameter trending response(s), safety/triggers, and out of range control/limit events. The advanced data collection can also make perfusion records more robust, such that they can be used for post-procedure analysis, historical analysis, and generation of more accurate procedure adjustments for future procedures and/or target parameters. For example, post-procedure data analysis can include statistical analyses by patient and/or by procedure categories, analysis of user-selected control ranges and adjustments, and data analysis for semi-automated algorithm development. Thus, simultaneously monitoring more information during a procedure allows practitioners to generate more effective and/or accurate procedure adjustments. These procedure adjustments can maintain and improve patient safety and procedure outcomes.

Referring to the process 800 in FIG. 8, a user (e.g., practitioner) selects a display type, target blood gas parameter, and other parameters to monitor in 802. As described throughout this disclosure, the user can select numeric and/or graphical displays for each of the monitored parameters. The user can also enable manual control of parameter adjustments as a default setting. Thus, the user or another practitioner performs any parameter adjustments during a procedure. The monitoring and control system may not semi-autonomously execute the user's pre-defined parameter adjustments upon happening of an event. In some implementations, however, the user can select a button on a display of the monitoring and control system during the procedure that causes the system to semi-autonomously performs the user's pre-defined parameter adjustment(s).

In 804, the user selects a desired control range and minimum and/or maximum alerts and/or alarm limits. The user can make these selections for the target blood gas parameter and any other parameters that the user selected for monitoring in 802. In some implementations, the user can be presented with preset options for each of the target parameter and the other parameters. The user can chose to keep the preset options, ignore them, or modify them.

The preset options can be previous configurations for the same target parameter and the other parameters. The previous configurations can be stored in a database (e.g., the parameter ranges database 322 in FIG. 3). The previous configurations could have been made by the same user or a different user and/or for the same procedure or a different procedure. In other implementations, the preset options can also be suggestions generated by the monitoring and control system. For example, the system can aggregate previous configurations and other data that collected during prior procedures (e.g., data stored in the procedure results database 324 in FIG. 3) to determine optimal ranges, limits, alarms, and/or alerts.

The user can also be presented with custom options. In other words, instead of receiving preset options, the user can set control ranges, alerts, and/or alarm limits manually and from scratch. The user may not be presented with previous configurations or suggested configurations. 804 and 806 can be performed at one or more configuration screens, as depicted in reference to FIGS. 6. 804 and 806 can also be performed before a procedure and/or at a start of the procedure. In some implementations, the user can perform 804 and 806 before any procedures that would use these settings occur. For example, the user can configure the monitoring and control system in advance of any scheduled procedures such that when the procedures occur, the monitoring and control system can be immediately prepped or loaded with the user-defined settings. In yet other implementations, the user can perform 804 and/or 806 during a procedure. For example, certain user-defined configurations may have been set before the procedure, but based on how the procedure is panning out in real-time, the user may decide to update or modify one or more of the user-defined configurations. Thus, 804 and/or 806 can be performed during the procedure.

The target parameter is sampled and/or displayed in 806. The target parameter can be displayed in a user interface on a display of the monitoring and control system, as described herein (e.g., refer to the user interface 600 in FIG. 6). In some implementations, the target parameter can be sampled, which includes displaying individual measurements. In some implementations, the target parameter can be displayed, which can include displaying a running average of more than one measurement. The target parameter is displayed in real-time. Therefore, for a duration of the procedure, the user can watch how the target parameter trends and make any necessary adjustments if need be. Any other parameters that the user selected to monitor (802) can also be sampled and/or displayed in 806. For example, the other parameters can be displayed in the same user interface as the target parameter. The other parameters can be displayed on a same graph as the target parameter. In other examples, the other parameters can be displayed in different user interface screens. The user can switch to the different user interface screens by selecting selectable options or buttons on the display of the monitoring and control system. The other parameters can also be displayed in different graphs.

Trending and/or slope of the target parameter is determined in 808. In some implementations, the monitoring and control system can determine the trend and/or slope of the target parameter. In other implementations, trending and/or slope of one or more of the other monitored parameters can be determined. The trend and/or slope of the target parameter is determined in real-time during the procedure.

The determined parameter trending and/or slope are displayed in 810 (e.g., refer to the user interface 600 in FIG. 6). For example, the slope of the target parameter can be displayed as a line in a graph. Any changes to the determined parameter trend and/or slope can be displayed in real-time. Additionally, control limit(s), alert limits, alarm limits, alert status, and alarm status can be displayed and updated in real-time in 810. One or more selectable options or buttons can be displayed. The user can select any of these buttons in order to perform some action on the monitored parameters. For example, selecting one of the buttons can cause the monitoring and control system to semi-autonomously perform the user's pre-defined control adjustment. Selecting another of the buttons can allow the user to manually control or adjust any one or more settings of any of the monitored parameters. Additional buttons can be displayed to the user to assist the user in performing perfusion or any other tasks during the procedure.

Once everything described above is displayed to the user, the user can choose to make no user selection in 812. In other words, any previous selection that the user made remains active. For example, if the user had previously selected an option to semi-autonomously increase the slope of the target parameter, then the user can decide to let that semi-autonomous adjustment continue until it is completed (e.g., the user previously defined this adjustment so that it automatically ends once a desired slope is achieved). As another example, the user may not have made any previous selection. Instead, the user may be monitoring the parameters and decided that no adjustment needs to be made to any of the parameters at that time. Thus, the user may make no selection in 812 and instead can continue watching in real-time the trending and/or slope of all the monitored parameters.

The process 800 can then return to sampling and/or displaying the target parameter and other monitored parameters in 806. One or more steps can be repeated in the process 800 in a feedback loop. In other words, the target parameter and other monitored parameters are continuously displayed and updated in real-time for a duration of the procedure, even when the user makes no adjustment selection in 812.

In addition or alternatively, once everything described above is displayed to the user (810), the user can enable manual control in 814. The user can select an option or button that allows the user to make all adjustments to the monitored parameters. Therefore, user-defined control adjustments may not be automatically executed by the monitoring and control system. Instead, the user can manually make those previous user-defined control adjustments (e.g., refer to 804). The user can also manually perform any other adjustments that the user had not previously defined in 802 and/or 804. As described throughout this disclosure, the user can make adjustments using selectable options on the display. For example, the display can be a touchscreen. The user can press on up and down buttons (e.g., + and − buttons) that are associated with one or more settings of the monitored parameters to make any manual adjustments. The user can also press or use physical buttons and/or dials to make manual adjustments. The physical buttons and/or dials can be part of the monitoring and control system. The physical buttons and/or dials can also be separate from the monitoring and control system and in communication (e.g., wired and/or wireless) with the system.

The process 800 can then return to sampling and/or displaying the target parameter and other monitored parameters in 806. One or more steps can be repeated in the process 800. In other words, the target parameter and other monitored parameters are continuously displayed and updated in real-time for a duration of the procedure, even when the user enables manual control in 814.

Whether manual control is enabled (814) or semi-autonomous adjustments (e.g., a previous user selection in 812) remain active, the user initiates a control adjustment to increase a trending slope in 816. The user can also initiate a control adjustment to decrease a trending slope in 818. As described herein, the user can press a selectable option (e.g., button) presented in the user interface for 816 and/or 818. When the user defined control ranges in 804, one or more selectable options or buttons in the user interface were updated to reflect the user-defined control ranges. Thus, a button that initiates a control adjustment to increase the trending slope (816) can be linked to a user-defined configuration indicating how much to increase the slope. Moreover, a button that initiates a control adjustment to decrease the trending slope (818) can be linked to a user-defined configuration indicating how much to decrease the slope.

Once the user initiates the control adjustment in 816 or 818, that control adjustment is executed in 820. As mentioned above, the user-defined configuration associated with the initiated control adjustment is semi-autonomously executed by the monitoring and control system. Thus, the control adjustment is executed for the user's desired corrective trending effect (e.g., increase the trending slope in 816 or decrease the trending slope in 818).

One or more example controls can be semi-autonomously executed by the monitoring and control system in 820. For example, the system can analyze arterial pCO2 versus a patient set point. Based on this analysis, the system can slowly increase or decrease arterial pCO2 by decreasing sweep gas by 0.1 L/min every 30 seconds. The system can also increase or decrease FICO2 0.01 every 15 seconds. As another example, the system can analyze arterial $pO_2$ versus the patient set point. Based on this analysis, the system can slowly increase or decrease arterial $pO_2$ by increasing FiO2 percentage by 0.05 every 15 seconds.

As yet another example, the system can analyze DO2 (indexed) versus patient set point. The system can slowly increase arterial blood flow by 0.05 L/min×every 15 seconds. In so doing, the system can also evaluate level detection and evaluate an FiO2 set point. The system can also slowly increase or decrease pO2 by increasing FiO2 percentage by 0.05 every 15 seconds. Moreover, the system can also make suggestions for hemoconcentration, an increase in effluent rate, and/or transfusions.

As another example, the system can semi-autonomously analyze oxygen extraction ratio, O2ER (VO2/DO2), versus the patient set point. As a result, the system can slowly increase arterial blood flow by 0.05 L/min×every 15 seconds. In so doing, the system can evaluate level detection and/or FiO2 set point. The system can also slowly increase or decrease pO2 by increasing FiO2 percentage by 0.05 every 15 seconds. Moreover, the system can make various suggestions for hemoconcentration, increase in effluent rate, transfusion(s), increasing or decreasing temperature, and/or increasing or decreasing a sedative.

As yet another example, the system can semi-autonomously analyze Cardiac Index (CI) versus the patient set point. The system can evaluate arterial flow, venous flow, and a level detection system. The system can also make suggestions based off such semi-autonomous evaluations. For example, if the arterial flow does not equal the venous flow by X %, the system can suggest to the practitioner to increase venous drainage. If the venous does not equal the arterial by X %, then the system can suggest to increase the arterial flow.

As yet another example, the system can monitor serum potassium level versus a (high or low) patient set point. The system can evaluate a previously delivered cardioplegia volume and ratio, time of cross clamp placement, time since delivery and EKG electrical activity versus the potassium set range. The system then can determine response alternatives. For example if the potassium is higher than set range level, the system can change the cardioplegia ratio and/or volume administered, concurrently if the level detection point is above a threshold, hemoconcentration or an increase in effluent rate can occur to decrease the serum potassium level. Additionally, the system can suggest to the practitioner start an administration of protocolized insulin and sodium bicarbonate or renal diuretic.

The monitoring and control system can provide for execution of one or more additional semi-autonomous controls and functionality, as described throughout this disclosure. In some implementations, the system can provide foundational functionality needed for optional advanced servo control of arterial and venous blood flow and gas delivery to user-specified target blood gas parameter values.

After execution of the control adjustment in 820, the process 800 can return to 806 and repeat one or more of the steps in the process 800. In other words, the target parameter and other monitored parameters are continuously displayed and updated in real-time for a duration of the procedure. The displayed target parameter and other monitored parameters can be updated in real-time to reflect changes to such parameters that result from execution of the control adjustment(s) (820).

Figure 9:
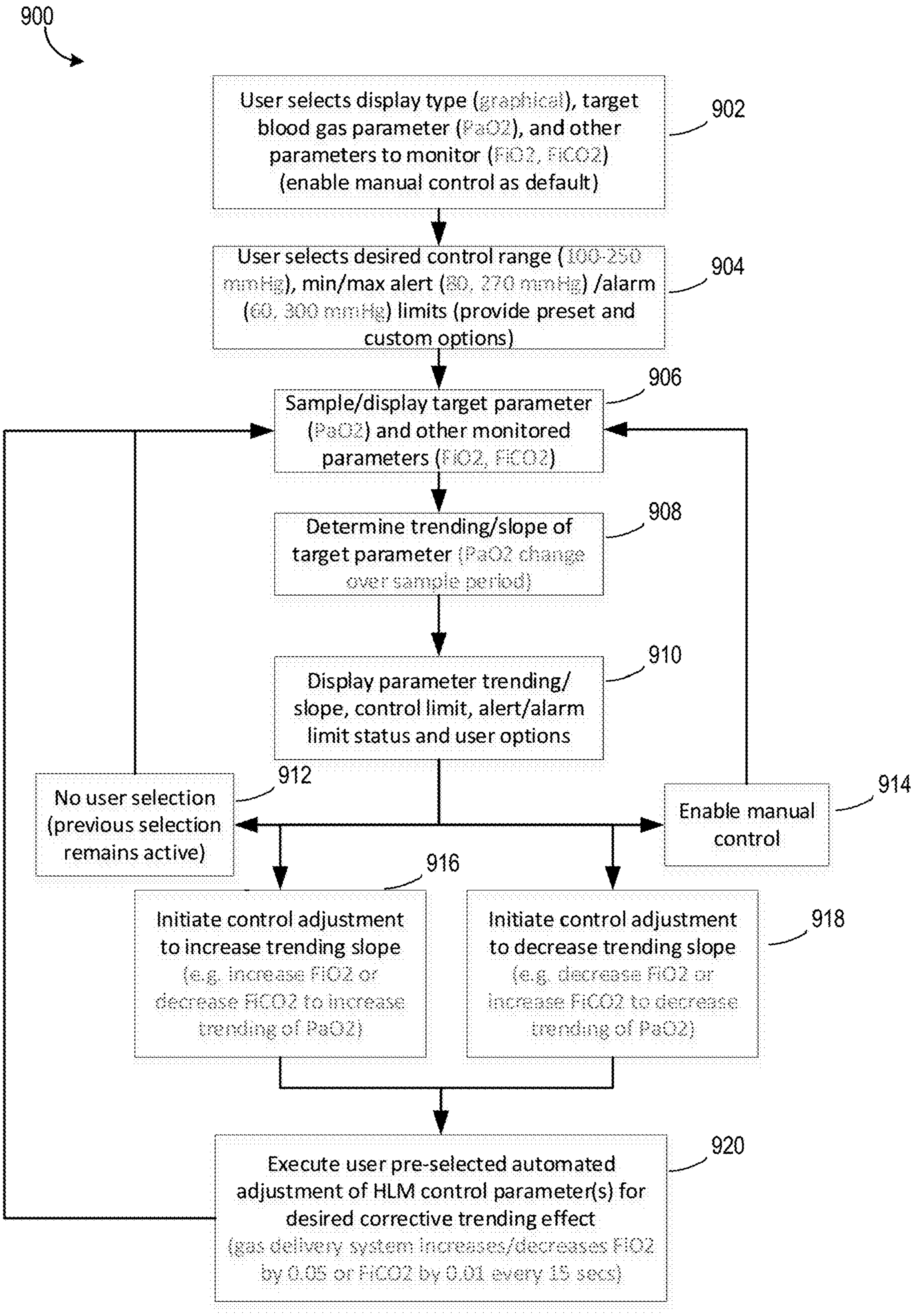
FIG. 9 is a flowchart of an example process for monitoring and controlling a partial pressure of oxygen parameter (PaO2).

FIG. 9 is a flowchart of a process 900 for monitoring and controlling a partial pressure of oxygen parameter (PaO2). The process 900 is an exemplary use of the process 800 depicted and described in reference to FIG. 8. In the example process 900, a practitioner (e.g., user) selected PaO2 as a target blood gas parameter in 902. The practitioner also selected FiO2 and FiCO2 as other parameters to monitor. The practitioner selected a graphical display type, as shown in FIG. 10.

The practitioner then selects a desired control range of 100-250 mmHg, a minimum alert of 80 mmHg, a maximum alert of 270 mmHg, a minimum alarm of 60 mmHg, and a maximum alarm of 300 mmHg in 904. These selections can be made in the primary configuration screen 700 as depicted and described in reference to FIG. 7.

Figure 10:
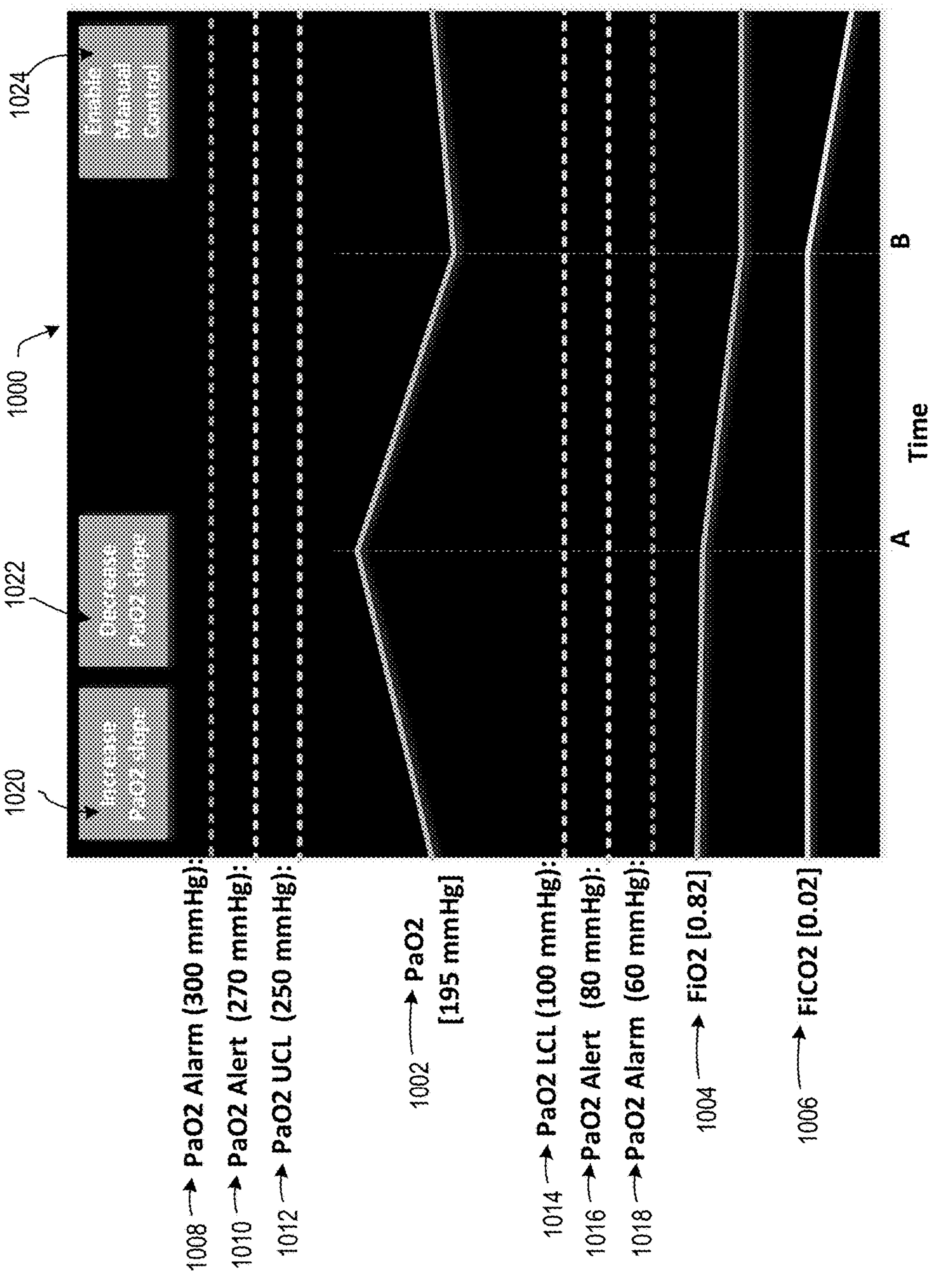
FIG. 10 is a graphical depiction of monitoring and controlling the partial pressure of oxygen parameter of FIG. 9.

PaO2, FiO2, and FiCO2 are sampled and displayed in the graphical display in 906 (e.g., refer to FIG. 10). PaO2 trending and/or slope can change over a sample period of time in 908 (e.g., refer to FIG. 10). As described in reference to FIG. 8, the parameter trends, slopes, control limits, and alert/alarm limit statuses can be displayed in a user interface with selectable buttons in 910. The practitioner can make no selection in 912 and/or enable manual control in 914. As one option, the practitioner can increase FiO2 or decrease FiCO2 to increase trending of PaO2 in 916. As another option, the practitioner can decrease FiO2 or increase FiCO2 to decrease trending of PaO2 in 918. Based on the practitioner's selection of 916 or 918, the monitoring and control system described herein can semi-autonomously increase or decrease FiO2 by 0.05 or FiCO2 by 0.01 every 15 seconds in 920.

FIG. 10 is a graphical depiction of monitoring and controlling the partial pressure of oxygen parameter of FIG. 9. A graph 1000 includes PaO2 trend 1002, FiO2 trend 1004, and FiCO2 control 1006. As described in reference to the process 900 in FIG. 9, these are the parameters that the practitioner selected for monitoring. The graph 1000 can optionally include real-time numeric values, as shown in FIG. 10. Depicted in the graph 1000 are maximum alarm 1008, maximum alert 1010, upper control limit 1012, lower control limit 1014, minimum alert 1016, and minimum alarm 1018. As described in reference to FIG. 9, these values were configured or set by the practitioner. Moreover, the graph 1000 includes an increase PaO2 slope button 1020, a decrease PaO2 slope button 1022, and an enable manual control button 1024. As described throughout this disclosure, one or more of the buttons 1020, 1022, and 1024 can provide different functionality based on the practitioner's configuration or selections. When the practitioner selects the buttons 1020 or 1022, the monitoring and control system can semi-autonomously execute a practitioner-defined control adjustment associated with the selected button. If the practitioner selects the button 1024, the practitioner can make any manual adjustments to the monitored parameters.

Any adjustments made to the parameters, whether semi-automated or manual, can be reflected in the graph 1000. Thus, the graph 1000 can reflect real-time changes to the monitored parameters trends. This is beneficial to assist the practitioner in accurately monitoring and controlling the parameters for a duration of the procedure.

Initial PaO2 1002 and FiO2 1004 values can be displayed and trended as time elapses. Prior to time A, the practitioner can observe that PaO2 1002 is trending upward toward the upper limit 1012 of the desired control range. At time A, the practitioner can initiate a pre-defined control adjustment action to correct the trending by pressing the Decrease PaO2 slope button 1022. The pre-defined control adjustment can instruct the monitoring and control system to decrease the PaO2 slope 1002 by decreasing FiO2 1004 by 0.05 every 15 secs. The resulting effect is depicted in the downward trending slope of PaO2 1002 and FiO2 1004. This pre-defined control adjustment was determined by the practitioner at the secondary configuration screen 702 as depicted and described in reference to FIG. 7.

Still referring to FIG. 10, prior to time B, the practitioner can observe that PaO2 1002 is trending downward more than desired. At time B, the practitioner can initiate a pre-defined control adjustment action to correct the PaO2 1002 trending by pressing the Increase PaO2 slope button 1020. The pre-defined control adjustment can instruct the monitoring and control system to increase the PaO2 slope 1002 by decreasing FiCO2 1006 by 0.01 every 15 secs. This pre-defined control adjustment was determined by the practitioner at the secondary configuration screen 702 as depicted and described in reference to FIG. 7. Moreover, at any time, the practitioner has the option to enable manual control of FiO2 1004 (e.g., by pressing the enable manual control button 1024). Doing so can immediately end any in-process semi-automated control adjustments of FiO2 1004 or one of the other parameters.

Figure 11:
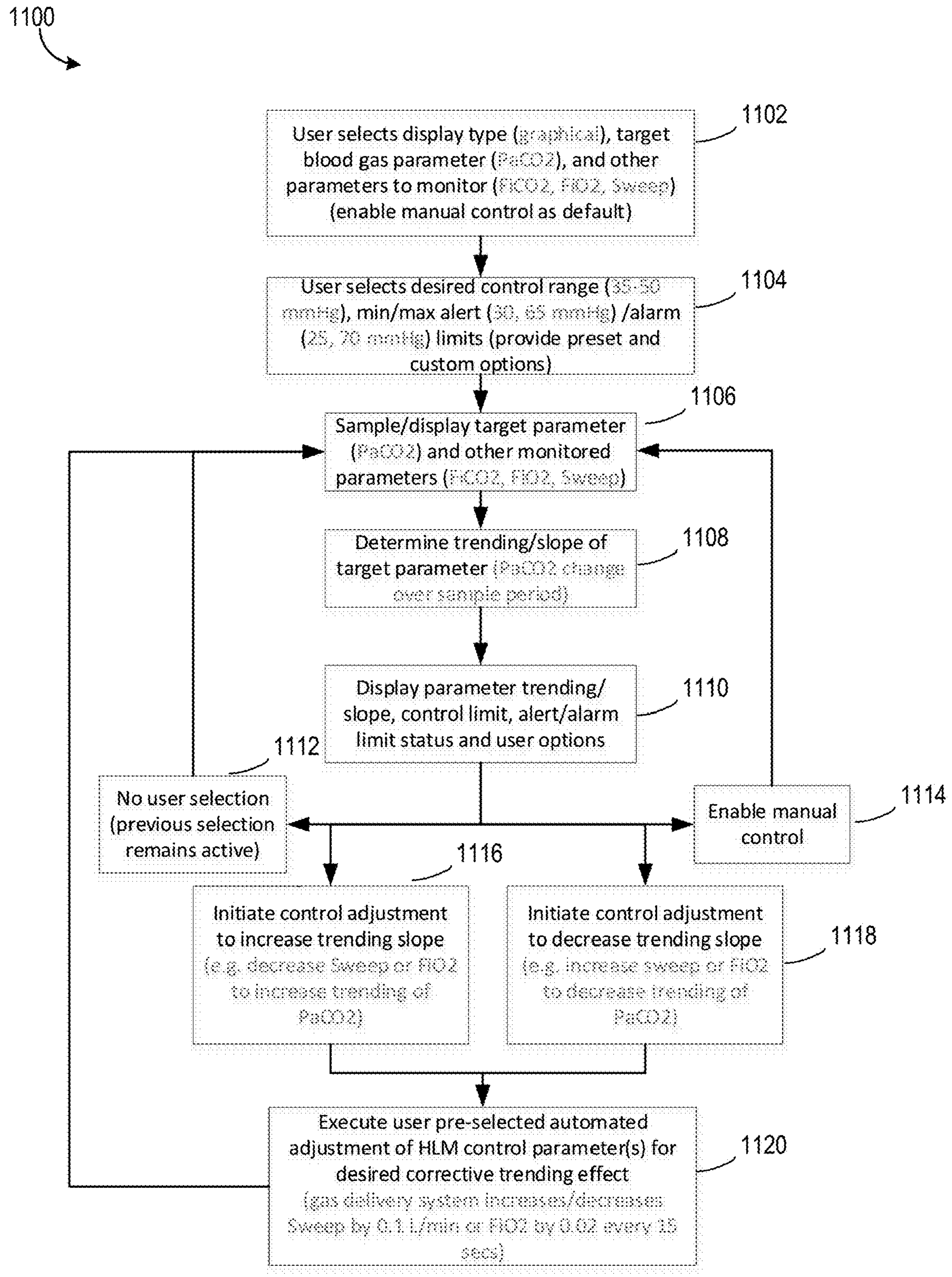
FIG. 11 is a flowchart of an example process for monitoring and controlling a partial pressure of carbon dioxide parameter (PaCO2).

FIG. 11 is a flowchart of a process for monitoring and controlling a partial pressure of carbon dioxide parameter (PaCO2). The process 1100 is an exemplary use of the process 800 depicted and described in reference to FIG. 8. In the example process 1100, a practitioner (e.g., user) selected PaCO2 as a target blood gas parameter in 1102. The practitioner also selected FiCO2, FiO2, and sweep as other parameters to monitor. The practitioner selected a graphical display type, as shown in FIG. 12.

The practitioner then selected a desired control range of 35-50 mmHg, a minimum alert of 30 mmHg, a maximum alert of 65 mmHg, a minimum alarm of 25 mmHg, and a maximum alarm of 70 mmHg in 1104. These selections can be made in the primary configuration screen 700 as depicted and described in reference to FIG. 7.

Figure 12:
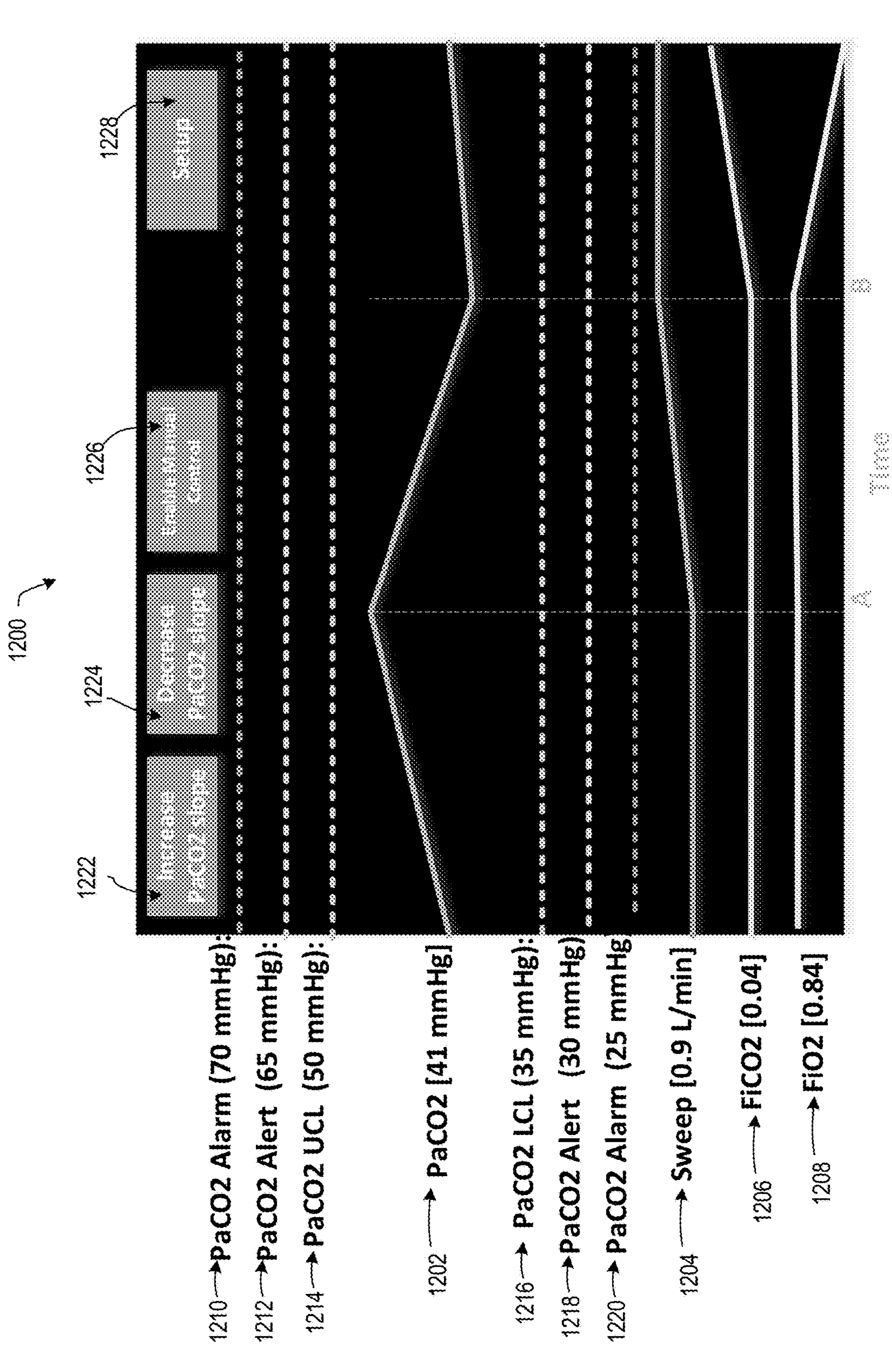
FIG. 12 is a graphical depiction of monitoring and controlling the partial pressure of carbon dioxide parameter of FIG. 11.

PaCO2, FiCO2, FiO2, and sweep are sampled and displayed in the graphical display in 1106 (e.g., refer to FIG. 12). PaCO2 trending and/or slope can change over a sample period of time in 1108 (e.g., refer to FIG. 12). As described in reference to FIG. 8, the parameter trends, slopes, control limits, and alert/alarm limit statuses can be displayed in a user interface with selectable buttons in 1110. The practitioner can make no selection in 1112 and/or enable manual control in 1114. As one option, the practitioner can decrease sweep or FiO2 to increase trending of PaCO2 in 1116. As another option, the practitioner can increase sweep or FiO2 to decrease trending of PaCO2 in 1118. Based on the practitioner's selection of 1116 or 1118, the monitoring and control system described herein can semi-autonomously increase or decrease sweep by 0.1 L/min or FiO2 by 0.02 every 15 seconds in 1120.

FIG. 12 is a graphical depiction of monitoring and controlling the partial pressure of carbon dioxide parameter of FIG. 11. A graph 1200 includes PaCO2 trend 1202, sweep trend 1204, FiCO2 trend 1206, and FiO2 trend 1208. As described in reference to the process 1100 in FIG. 11, these are the parameters that the practitioner selected for monitoring. The graph 1200 can optionally include real-time numeric values, as shown in FIG. 12. Depicted in the graph 1200 are maximum alarm 1210, maximum alert 1212, upper control limit 1214, lower control limit 1216, minimum alert 1218, and minimum alarm 1220. As described in reference to FIG. 11, these values were configured or set by the practitioner. Moreover, the graph 1200 includes an increase PaCO2 slope button 1222, a decrease PaCO2 slope button 1224, an enable manual control button 1226, and a setup button 1228. As described throughout this disclosure, one or more of the buttons 1222, 1224, 1226, and 1228 can provide different functionality based on the practitioner's configuration or selections. When the practitioner selects the buttons 1222 or 1224, the monitoring and control system can semi-autonomously execute a practitioner-defined control adjustment associated with the selected button. If the practitioner selects the button 1226, the practitioner can make any manual adjustments to the monitored parameters.

Any adjustments made to the parameters, whether semi-automated or manual, can be reflected in the graph 1200. Thus, the graph 1200 can reflect real-time changes to the monitored parameters trends. This is beneficial to assist the practitioner in accurately monitoring and controlling the parameters for a duration of the procedure.

As depicted in FIG. 12, initial PaCO2 1202, sweep 1204, and FiCO2 1206 values can be displayed and trended as time elapses. Prior to time A, the practitioner can observe that PaCO2 1002 is trending upward toward the upper limit 1214 of the desired control range. At time A, the practitioner can initiate a pre-defined control adjustment action to correct the trending by pressing the Decrease PaCO2 slope button 1224. This control adjustment can instruct the monitoring and control system described herein to decrease the slope of PaCO2 1202 by increasing sweep 1204 by 0.1 L/min every 15 secs. The resulting effect is noted in the downward trending slope of PaCO2 1202, sweep 1204, and FiCO2 1206.

Prior to time B, the practitioner can observe that PaCO2 1202 is trending downward more than desired. At time B, the practitioner can initiate a pre-defined control adjustment action to correct the trending by pressing the Increase PaCO2 slope button 1222. This control adjustment can instruct the monitoring and control system to increase the slope of PaCO2 1202 by increasing FiCO2 1206 by 0.01 and decreasing FiO2 1208 by 0.02 every 15 secs. Moreover, at any time, the practitioner has the option to enable manual control of sweep 1204 (e.g., by pressing the button 1226), which will immediately end any in-process semi-automated control adjustments of sweep 1204.

Figure 13A:
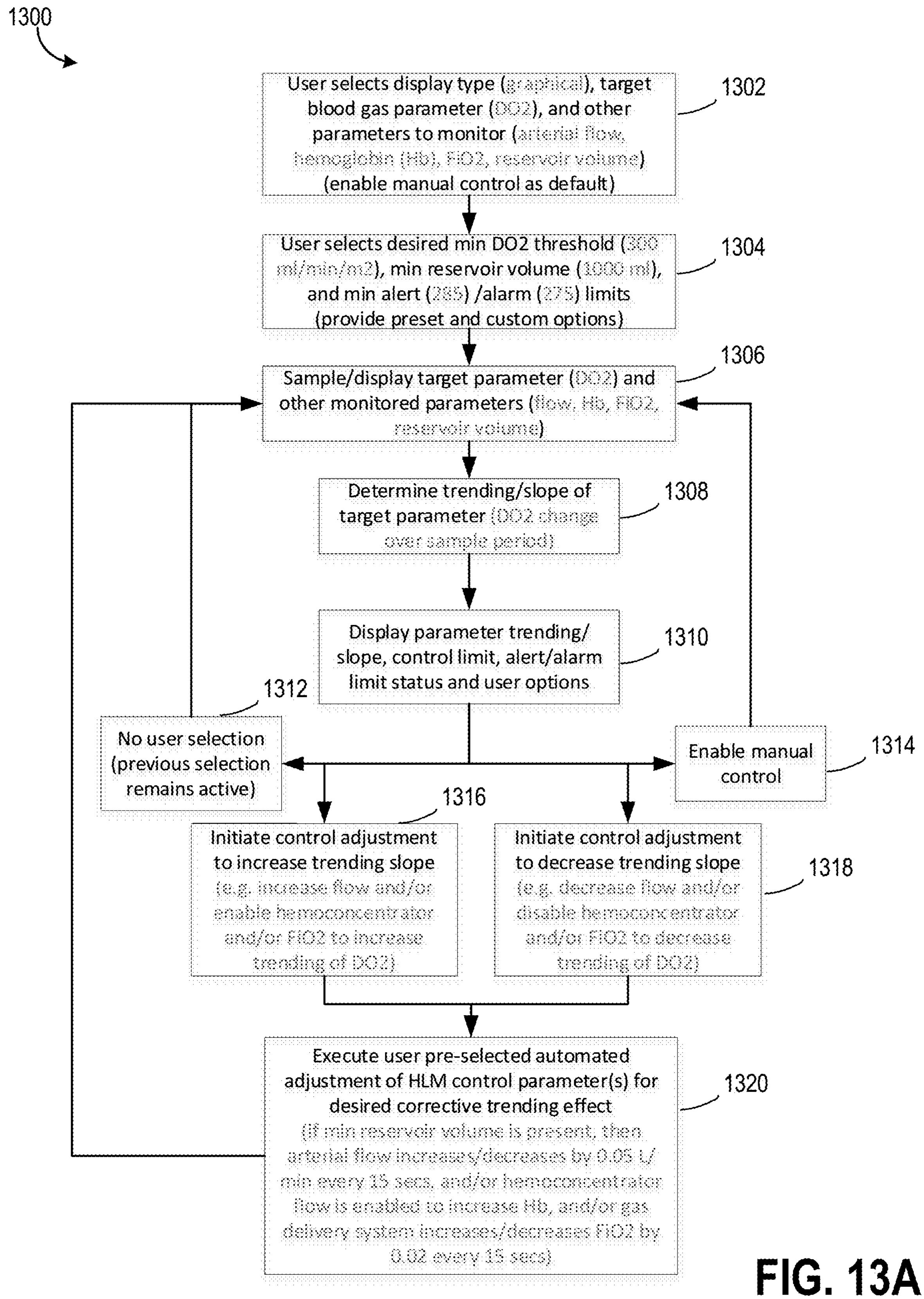
FIG. 13A is a flowchart of an example process for monitoring and controlling a global oxygen delivery parameter (DO2).

FIG. 13A is a flowchart of a process 1300 for monitoring and controlling a global oxygen delivery parameter (DO2). Delivered Oxygen is a calculated parameter that has various measured inputs from a CDI that determines the delivered oxygen to end organs during cardiopulmonary bypass. For example, DO2 can be determined using an equation such as the following: DO2=[10×CO (arterial)×((Hb×1.36×SaO2)+(0.0031×PaO2))]/patients BSA, if indexed. Inputs to this example equation include cardiac output (Q) patients arterial flow (CO), hemoglobin or red cell oxygen carrying capability (Hb), arterial saturation of blood (SaO2), partial pressure of oxygen (PaO2), and body surface area (BSA).

Maintaining optimal delivery of oxygen to end organs can provide for better patient outcomes. For example, an incident rate of acute kidney injury (AKI) during bypass can be linked to a lack of oxygen to outer medulla of the kidney. A critical oxygen delivery threshold of between 272 and 280 ml/min/m2 can be established and maintained during the bypass for adult patients. The incident rate of AKI can double when a patient's calculated oxygen delivery to the kidney is below this threshold value.

Additionally, there is a physiological relationship between oxygen delivery and carbon dioxide production. Oxygen can be delivered to end cells and carbon dioxide can be produced from those cells as a waste product of metabolism. When cells are in aerobic metabolism, delivered oxygen can be used and carbon dioxide can be produced. If the cells are in in anerobic metabolism, glucose and stored, dissolved oxygen can be used. Thus, lactate can be produced. If lactate is being produced by the cells, bicarbonate can buffer the lactic acid, and create more carbon dioxide. Since bicarbonate-based buffering of lactic acid occurs during anerobic metabolism, an increase in extra CO2 production can occur in under-perfused, critically ill and septic patients. There may be clinical situations in which oxygen delivery (DO2) may not be adequate, therefore anerobic metabolism at the cellular level occurs and produces an increase in CO2. The evaluation of a lactate level versus overall CO2 production can help predict the patients in which DO2 may not be sufficient. A ratio between oxygen delivery and carbon dioxide production of less than 5.3, an absolute value of VCO2 above 60 ml/min along with an increase in lactic acid, can be a predictor of AKI.

Thus, providing real time monitoring and primary control over factors that can alter the DO2 parameter can improve patient outcomes and safety. When monitoring DO2 using the process 1300 as depicted in FIG. 13A, the practitioner can have an absolute number for the DO2 to consider along with variables that are inputs to the absolute DO2 value. When the minimal threshold value is reached, the practitioner can take into account one or more factors to increase that absolute number for the DO2. Some of those factors can include increasing the patient's cardiac output, increasing a hemoglobin count (e.g., reducing hemodilution) of the patient, increasing saturation of available hemoglobin mass, and/or increasing a dissolved oxygen component by altering PaO2.

Using the disclosed process 1300, the practitioner can better prioritize clinical decisions and/or adjustments during a procedure. Decisions can be prioritized such that overall DO2 is increased first by increasing cardiac output (e.g., arterial flow). Next, the overall DO2 can be increased by increasing the hemoglobin count (e.g., a reduction in hemodilution). Then, DO2 can be increased by increasing PaO2 and O2 saturation by an increase in FiO2.

With each clinical action or decision, one or more factors can be modified by the practitioner to improve DO2 (e.g., according to the process 1300 in FIG. 13A). For example, to increase cardiac output, the practitioner, using the system described herein, can evaluate patient hemodynamics, evaluate whether there is a tolerance for an increase in flow to not flood a surgical field of fluid, and whether there is an amount of fluid in the reservoir to enable an increase in flow (e.g., the cardiac output). If the increase in flow can be tolerated, the practitioner can enable vacuum-assisted venous return, which can aid in venous return and aid in cardiac output to the patient. As another example, to increase a hemoglobin value of the patient, the practitioner can configure a volume in the reservoir to implement hemoconcentration, a volume in the reservoir to implement a transfusion of red blood cells, Delta Q, and a time to termination of the procedure (e.g., cardiopulmonary bypass). To implement the hemoconcentration, the practitioner can configure enough volume in the reservoir, which enables routing of arterial blood through a hemoconcentrator circuit, as depicted and described throughout this disclosure. To implement transfusion of the red blood cells, the practitioner can configure a low volume in the reservoir necessitating a transfusion. Moreover, Delta Q can be an acceptable difference of arterial and venous flow.

As yet other examples, to increase saturation of the available hemoglobin mass, the practitioner can configure the monitoring and control system to increase FiO2. To increase dissolved oxygen by increasing PaO2, the practitioner can configure the monitoring and control system to increase FiO2.

As another example, in conjunction with DO2 monitoring, enhanced control and monitoring of expired CO2, and volumetric carbon dioxide (VCO2), the DO2 to VCO2 ratio and lactate production can aid in metabolic demands of a patient undergoing cardiopulmonary bypass. The relationship of oxygen delivery is such that when oxygen delivery to end organs decreases, carbon dioxide production increases and vice versa; when oxygen delivery increases to the cells, carbon dioxide production decreases. Therefore, to decrease absolute expiredCO2, VCO2, the practitioner can configure the monitoring and control system to increase DO2, increase gas flow and decrease FiCO2, suggest added anesthetic management, and/or suggest pharmacological management. To increase the DO2 to VCO2 ratio, the practitioner can configure the monitoring and control system to increase DO2, increase gas flow and decrease FiCO2, suggested added anesthetic management, and/or suggest added pharmacological management. Moreover, to decrease lactate production, the practitioner can configure the monitoring and control system to increase DO2, increase gas flow and decrease FiCO2, suggest added anesthetic management, and/or suggest pharmacological management.

Still referring to FIG. 13A, the process 1300 is an exemplary use of the process 800 depicted and described in reference to FIG. 8. In the example process 1300, a practitioner (e.g., user) selected DO2 as a target blood gas parameter in 1302. The practitioner also selected arterial flow, hemoglobin (Hb), FiO2, and reservoir volume as other parameters to monitor. The practitioner selected a graphical display type, as shown in FIG. 14.

The practitioner then selected a desired control range of 300 ml/min/m2, a minimum reservoir volume of 1000 ml, a minimum alert of 285 ml/min/m2, and a minimum alarm of 275 ml/min/m2 in 1304. These selections can be made in configuration screens as depicted and described in reference to FIG. 7.

Figure 14:
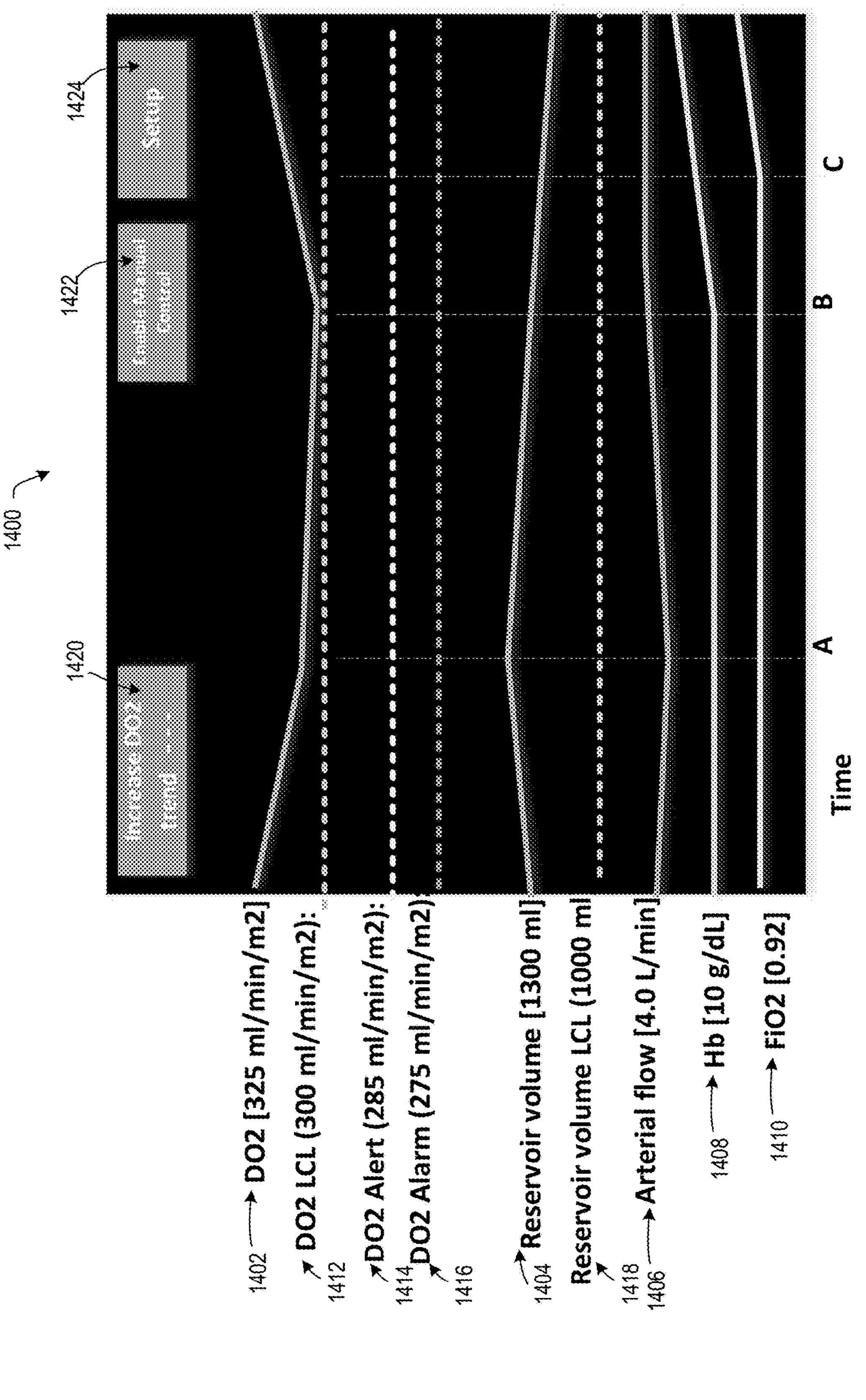
FIG. 14 is a graphical depiction of monitoring and controlling the global oxygen delivery parameter of FIGS. 13A-13B.

DO2, flow, Hb, FiO2, and reservoir volume are sampled and displayed in the graphical display in 1306 (e.g., refer to FIG. 14). DO2 trending and/or slope can change over a sample period of time in 1308 (e.g., refer to FIG. 14). As described in reference to FIG. 8, the parameter trends, slopes, control limits, and alert/alarm limit statuses can be displayed in a user interface with selectable buttons in 1310. The practitioner can make no selection in 1312 and/or enable manual control in 1314. As one option, the practitioner can increase flow and/or enable a hemoconcentrator and/or FiO2 to increase trending of DO2 in 1316. As another option, the practitioner can decrease flow and/or disable the hemoconcentrator and/or FiO2 to decrease trending of DO2 in 1318.

Based on the practitioner's selection of 1316 or 1318, the monitoring and control system described herein can make semi-autonomous adjustments in 1320. For example, if the minimum reservoir volume is present, then arterial flow can be increased and/or decreased by 0.05 L/min every 15 seconds. In addition or alternatively, hemoconcentrator flow can be enabled to increase Hb. In addition or alternatively, the monitoring and control system can increase or decrease FiO2 by 0.02 every 15 seconds.

Figure 13B:
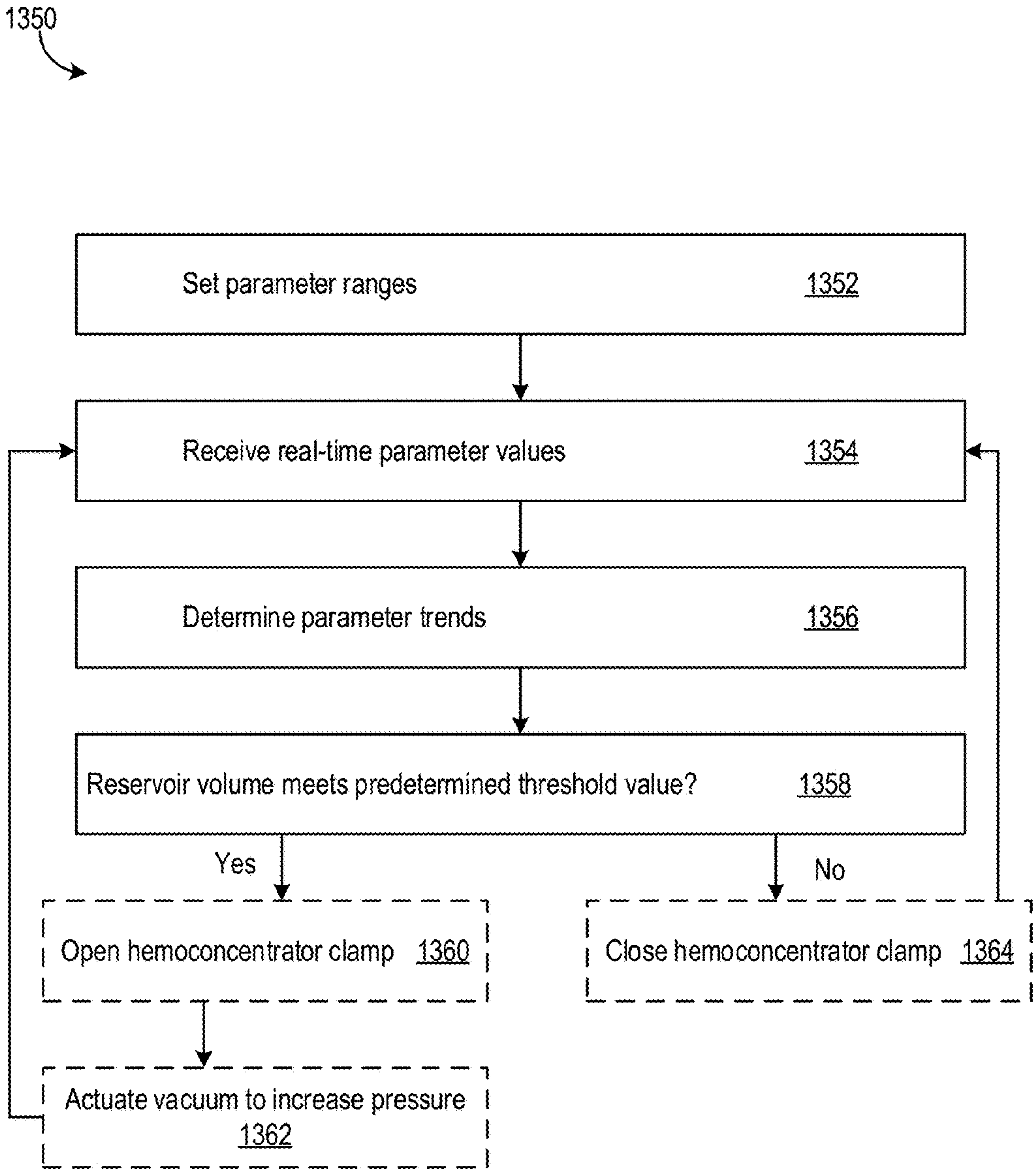
FIG. 13B is a flowchart of an example process for controlling a hemoconcentrator.

FIG. 13B is a flowchart of a process 1350 for controlling a hemoconcentrator (e.g., the hemoconcentrator circuit 334 in FIG. 3). The process 1350 can be performed in conjunction with the process 1300 depicted and described in reference to FIG. 13A. Moreover, the process 1350 can be performed to semi-autonomously control the hemoconcentrator circuit 334, as depicted and described in reference to FIG. 3.

Referring to the process 1350, parameter ranges can be set in 1352. A practitioner can set the parameter ranges according to the process 1300 depicted and described in reference to FIG. 13A. Real-time parameter values can be received in 1354. For example, a blood flow of the patient can be identified using one or more sensors as depicted and described throughout this disclosure. Parameter trends can be determined in 1356, as described herein.

Next, it can be determined whether a reservoir volume meets a predetermined threshold value in 1358. The predetermined threshold value can be determined by the practitioner when configuring the monitored parameters (e.g., refer to FIGS. 7, 13A).

If the volume does meet the predetermined threshold value, then a hemoconcentrator clamp can be opened in 1360. The monitoring and control system described herein can semi-autonomously open the clamp. Alternatively, the practitioner can manually open the clamp. By opening the hemoconcentrator clamp, blood can flow into the hemoconcentrator. As a result, a hemoglobin level can be increased, which will also increase the patient's DO2 level.

In addition or alternatively, a vacuum can be actuated to increase pressure to move the blood in 1362. The monitoring and control system described herein can semi-autonomously actuate the vacuum. Alternatively, the practitioner can manually actuate the vacuum. The vacuum can be positioned on either side of the hemoconcentrator as an alternative mechanism to increase transmembrane pressure. Steps 1354-1358 can then be repeated for a duration of the procedure.

If the volume does not meet the predetermined threshold value, then the hemoconcentrator clamp can remain closed in 1364. Steps 1354-1358 can then be repeated for the duration of the procedure.

Semi-autonomously adjusting the hemoconcentrator clamp can be advantageous to create higher or lower transmembrane pressure to get volume of the blood flow through the circuit faster or slower. The hemoconcentrator clamp can be positioned on an outlet side of the hemoconcentrator such that pressure of blood flow can be controlled on a blood side of the hemoconcentrator. Moreover, in some implementations, the monitoring and control system described herein can semi-autonomously or automatically modulate the hemoconcentrator clamp based on real-time sensed parameter values, ranges, and/or trends.

FIG. 14 is a graphical depiction of monitoring and controlling the global oxygen delivery parameter of FIGS. 13A-13B. A graph 1400 includes DO2 trend 1402, reservoir volume trend 1404, arterial flow trend 1406, Hb trend 1408, and FiO2 trend 1410. As described in reference to the process 1300 in FIG. 13A, these are the parameters that the practitioner selected for monitoring. The graph 1400 can optionally include real-time numeric values, as shown in FIG. 14. Depicted in the graph 1400 are DO2 lower control limit 1412, DO2 minimum alert 1414, DO2 minimum alarm 1416, and reservoir volume lower control limit 1418. As described in reference to FIG. 13A, these values were configured or set by the practitioner. Moreover, the graph 1400 includes an increase DO2 trend button 1420, an enable manual control button 1422, and a setup button 1424. As described throughout this disclosure, one or more of the buttons 1420, 1422, and/or 1424 can provide different functionality based on the practitioner's configuration or selections. When the practitioner selects the buttons 1420, the monitoring and control system can semi-autonomously execute a practitioner-defined control adjustment associated with the selected button. If the practitioner selects the button 1422, the practitioner can make any manual adjustments to the monitored parameters.

Any adjustments made to the parameters, whether semi-automated or manual, can be reflected in the graph 1400. Thus, the graph 1400 can reflect real-time changes to the monitored parameters trends. This is beneficial to assist the practitioner in accurately monitoring and controlling the parameters for a duration of the procedure.

As depicted, initial DO2 1402, reservoir volume 1404, arterial flow 1406, Hb 1408, and FiO2 1410 values can be displayed and trended as time elapses. Prior to time A, the practitioner can observe that DO2 1402 is trending slightly downward toward the minimum desired threshold, the lower control limit 1412. At time A, the practitioner can initiate a pre-defined control adjustment action to correct the trending by pressing the Increase DO2 trend button 1420. This control adjustment can instruct the monitoring and control system to semi-autonomously increase the DO2 slope 1402 by increasing arterial flow 1406 by 0.05 L/min every 15 secs (e.g., a first level of increasing DO2 trend).

Prior to time B, the practitioner can observe that DO2 1402 is still trending slightly downward. At time B, the practitioner can press the Increase DO2 trend button 1420 again, which continues to increase the arterial flow 1406 by 0.05 L/min every 15 sec, but also enables flow through the hemoconcentrator to reduce hemodilution and increase hemoglobin 1408 (e.g., a second level of increasing DO2 trend).

Prior to time C, the practitioner can observe that DO2 1402 is trending upward. The practitioner may want to further increase the trend 1402. Therefore, at time C, the practitioner can press the Increase DO2 trend button 1420 again, which continues to increase the arterial flow 1406 by 0.05 L/min every 15 sec, keeps flow enabled through the hemoconcentrator to reduce hemodilution and increase hemoglobin 1408, and also increase FiO2 1410 by 0.02 every 15 secs (e.g., a third level of increasing DO2 trend).

The practitioner can configure multiple levels of increasing the DO2 trend 1402, as described above. Moreover, at any time, the practitioner can enable manual control of arterial flow 1406, FiO2 1410, enabling the hemoconcentrator, and/or adjusting the hemoconcentrator clamp and/or vacuum. Any manual control can immediately end current in-process semi-automated control adjustments of DO2 1402.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A system for monitoring and controlling patient parameters of a patient during a medical procedure using a heart/lung machine system, the system comprising:

the heart/lung machine system comprising:

an extracorporeal blood circuit including: (i) a venous catheter for removing blood from the patient, (ii) an oxygenator for adding oxygen to the blood and removing carbon dioxide from the blood, and (iii) an aortic cannula for returning the blood to the patient; and one or more pumps for propelling the blood through the extracorporeal blood circuit and back to the patient during the medical procedure;

a data store for storing: (i) patient parameters that indicate an actual physiologic status of the patient and that are measured in real-time during the medical procedure, and (ii) semi-autonomous parameter trending response adjustments;

a user device comprising a display screen configured to output actual measurements of the patient parameters as the patient parameters are measured in real-time during the medical procedure, wherein the user device is also configured to output a first graphical user interface (GUI) display on the display screen of the user device before each performance of the medical procedure and to receive for a particular patient, via the first GUI display before each performance of the medical procedure, user input establishing parameter settings for the particular patient that include: (i) ranges for each of the patient parameters and (ii) the semi-autonomous parameter trending response adjustments for one or more of the patient parameters, wherein the semi-autonomous parameter trending response adjustments are executable during the medical procedure in response to a user selection of an option presented via the display screen of the user device, and wherein the option is determined and presented based on the real-time measurements of the patient parameters that are measured during the medical procedure; and a computer system for monitoring and controlling, in real-time during the medical procedure, the patient parameters, the computer system configured to:

receive, from the user device before each performance of the medical procedure, the user input establishing the parameter settings for the particular patient that include the ranges for each of the patient parameters and including the semi-autonomous parameter trending response adjustments for the one or more of the patient parameters;

automatically determine one or more suggested parameter adjustments that are automatically determined during the medical procedure based on: (i) the patient parameters that indicate the actual physiologic status of the particular patient and that are measured in real-time during the medical procedure and (ii) the user input of the semi-autonomous parameter trending response adjustments for the one or more of the patient parameters that was received before the medical procedure;

generate, based on the user input indicating the parameter settings, a second GUI display to be outputted by the display screen of the user device during the medical procedure, wherein the second GUI display provides a display of:

(i) the patient parameters that indicate the actual physiologic status of the particular patient and that are measured in real-time during the medical procedure, (ii) controls for a user to adjust one or more of the ranges for each of the displayed patient parameters, (iii) the one or more suggested parameter adjustments, and (iv) one or more user-selectable controls for the user to instruct the computer system to execute the one or more suggested parameter adjustments;

generate projected future trends of the patient parameters based on the real-time measurements of the patient parameters that are measured during the medical procedure;

update the second GUI display to display the projected future trends;

transmit the updated second GUI display to the user device to be outputted by the display screen of the user device;

receive, from the user device, user input indicating a selection by the user of the one or more user-selectable controls to instruct the computer system to execute one or more of the one or more suggested parameter adjustments; and execute, in response to the user input, the one or more suggested parameter adjustments that was selected by the user via the user input.

2. The system of claim 1, wherein the computer system is further configured to:

receive, (i) from at least one of the heart/lung machine system and the one or more sensors and (ii) after execution of the user-selected one or more suggested parameter adjustments, updated real-time patient parameters;

determine, based on the updated real-time patient parameters, updated trends for each of the updated real-time patient parameters;

update the second GUI display to further provide the updated real-time patient parameters and the updated trends for each of the updated real-time patient parameters;

transmit the updated second GUI display to the user device to be outputted by the display screen of the user device; and store, in the data store, (i) the executed one or more suggested parameter adjustments, (ii) the updated real-time patient parameters, and (iii) the updated trends for each of the updated real-time patient parameters.

3. The system of claim 1, wherein the one or more sensors include at least one of: a camera, an arterial shunt sensor, a venous shunt sensor, an air detector, a bubble sensor, an arterial optical fluorescent sensor, a venous optical fluorescent sensor, an arterial optical reflective sensor, a venous optical reflective sensor, a hematocrit level sensor, and a hemoglobin sensor.

4. The system of claim 1, wherein the one or more sensors are configured to monitor, in real-time before and during the medical procedure, at least one of a blood gas level, a blood flow, a venous reservoir blood level, a temperature, and a pressure of the particular patient.

5. The system of claim 1, wherein the one or more semi-autonomous parameter trending response adjustments include adjusting an arterial blood flow of the particular patient, adjusting a venous blood flow of the particular patient, adjusting a venous vacuum source, adjusting a hemoconcentrator circuit flow, monitoring an exhaust gas flow and concentration, monitoring an anesthetic gas inlet and outlet, adjusting a ventilation gas flow, adjusting a ventilation gas concentration, monitoring inlet gas ventilation, and monitoring exhaust gas ventilation.

6. The system of claim 1, wherein the second GUI display provides, in a single interface and for each of the displayed real-time patient parameters, (i) sensed changes in the real-time patient parameters, (ii) the user-selectable controls to perform the one or more suggested parameter adjustments to the displayed real-time patient parameters, (iii) user-selectable controls to perform one or more manual adjustments to the displayed real-time patient parameters, and (iv) the projected future trends for each of the displayed real-time patient parameters.

7. The system of claim 6, wherein the computer system is further configured to receive, from the user device and during the medical procedure, updated user input indicating (i) updated ranges for one or more of the displayed real-time patient parameters and (ii) updated semi-autonomous parameter trending response adjustments to one or more of the displayed real-time patient parameters.

8. The system of claim 1, wherein generating, by the computer system, the projected future trends for each of the real-time patient parameters comprises determining a slope for each of the real-time patient parameters over a predetermined period of time.

9. The system of claim 1, wherein the ranges for each of the particular patient parameters include upper and lower limits, and wherein the computer system is further configured to update the second GUI display to further provide the upper and lower limits concurrently with the projected future trends.

10. The system of claim 1, wherein the one or more semi-autonomous parameter trending response adjustments include (i) incrementally increasing, based on the parameter settings and the projected future trends, a slope of the one or more of the displayed real-time patient parameters until an upper limit is reached and (ii) incrementally decreasing, based on the parameter settings and the projected future trends, the slope of the one or more of the displayed real-time patient parameters until a lower limit is reached.

11. The system of claim 1, wherein executing, by the computer system, the user-selected one or more suggested parameter adjustments includes at least one of (i) semi-autonomously increasing a slope of one of the real-time patient parameters until the slope of the one of the real-time patient parameters is within a first threshold range defined by the parameter settings and (ii) semi-autonomously decreasing a slope of another of the real-time patient parameters until the slope of the another of the real-time patient parameters is within a second threshold range defined by the parameter settings.

12. The system of claim 1, wherein the computer system is further configured to update the second GUI display to further provide a graph depicting changes to a user-selected real-time patient parameter of the displayed real-time patient parameters, wherein trend lines depicted in the graph are adjusted, by the computer system in real-time, in response to (i) sensed changes in the user-selected real-time patient parameter, (ii) sensed changes in one or more other real-time patient parameters that are associated with the user-selected real-time patient parameter, and (iii) execution of one or more suggested parameter adjustments.

13. The system of claim 1, wherein the computer system is further configured to:

receive, from the one or more sensors and during the medical procedure, signals indicating a blood level in a venous reservoir;

automatically open a clamp of a hemoconcentrator in fluid communication with the venous reservoir based on the signals indicating that the blood level satisfies a predetermined threshold value, wherein the predetermined threshold value is defined by the parameter settings;

actuate, in response to opening the clamp of the hemoconcentrator and during the medical procedure, a vacuum of the hemoconcentrator by a predetermined amount, wherein the predetermined amount is defined by the parameter settings;

receive, from the one or more sensors and during the medical procedure, updated signals indicating the blood level in the venous reservoir; and close the clamp of the hemoconcentrator in response to determining that the signals are less than the predetermined threshold value.

* * * * *